(12) United States Patent
Turner et al.

(10) Patent No.: US 10,190,158 B2
(45) Date of Patent: Jan. 29, 2019

(54) SYSTEMS AND METHODS FOR SELECTIVELY ADDRESSING SPARSELY ARRANGED ELECTRONIC MEASUREMENT DEVICES

(71) Applicant: PACIFIC BIOSCIENCES OF CALIFORNIA, INC., Menlo Park, CA (US)

(72) Inventors: Stephen Turner, Seattle, WA (US); Jonas Korlach, Carmas, WA (US); Steven Warren, New York, NY (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 371 days.

(21) Appl. No.: 15/227,357

(22) Filed: Aug. 3, 2016

(65) Prior Publication Data
US 2017/0038333 A1    Feb. 9, 2017

Related U.S. Application Data

(60) Provisional application No. 62/239,176, filed on Oct. 8, 2015, provisional application No. 62/201,731, filed on Aug. 6, 2015.

(51) Int. Cl.
*G01N 27/414*    (2006.01)
*C12Q 1/68*    (2018.01)
(Continued)

(52) U.S. Cl.
CPC .......... *C12Q 1/6869* (2013.01); *B82Y 10/00* (2013.01); *B82Y 15/00* (2013.01);
(Continued)

(58) Field of Classification Search
CPC .......... G01N 27/4148; G01N 27/4146; G01N 27/4145; G11C 19/28; H01L 29/0669;
(Continued)

(56) References Cited

U.S. PATENT DOCUMENTS 5,143,854 A    9/1992 Pirrung et al.
5,424,186 A    6/1995 Fodor et al.
(Continued)

FOREIGN PATENT DOCUMENTS

WO    WO 2013/121224 A1    8/2013
WO    WO2014/060954    *    4/2014

OTHER PUBLICATIONS

Barsoukov, et al. "Impedance Spectroscopy: Theory, Experiment, and Applications", Wiley, 2005.
(Continued)

*Primary Examiner* — Gregory J Toatley, Jr.
*Assistant Examiner* — Lynda Dinh
(74) *Attorney, Agent, or Firm* — Morgan, Lewis & Bockius LLP

(57) ABSTRACT

A circuit comprising a substrate with sectors on the substrate is provided, each sector comprising clock and data lines, a controller in electrical communication with the clock and data lines, a counter bias line, an amplifier input line and nano-electronic measurement devices on the substrate. A source of each device is coupled to the counter bias line and a drain of each device is coupled to the amplifier input line to obtain an electrical signal on the drain, the identity of which is determined by electrical interaction between the device and a charge label. Each device drain is gated by a corresponding switch between an on state, in which the drain is connected to the amplifier input line, and an off state, in which the drain is isolated from the amplifier input line. The controller controls switch states responsive to clock signal line pulses and data input line data.

36 Claims, 26 Drawing Sheets

(51) Int. Cl.

| | |
|---|---|
| *C12Q 1/6869* | (2018.01) |
| *G11C 19/28* | (2006.01) |
| *H01L 29/06* | (2006.01) |
| *H01L 29/16* | (2006.01) |
| *B82Y 10/00* | (2011.01) |
| *B82Y 15/00* | (2011.01) |

(52) U.S. Cl.
CPC ..... *G01N 27/4145* (2013.01); *G01N 27/4146* (2013.01); *G01N 27/4148* (2013.01); *G11C 19/28* (2013.01); *H01L 29/0669* (2013.01); *H01L 29/1606* (2013.01); *H01L 29/0673* (2013.01)

(58) Field of Classification Search
CPC ............ H01L 29/1606; H01L 29/0673; C12Q 1/6869; C12Q 2533/101; C12Q 2565/607; B82Y 15/00
See application file for complete search history.

(56) References Cited

U.S. PATENT DOCUMENTS

| | | | |
|---|---|---|---|
| 5,624,711 | A | 4/1997 | Sundberg et al. |
| 5,723,584 | A | 3/1998 | Schatz |
| 5,874,239 | A | 2/1999 | Schatz |
| 5,919,523 | A | 7/1999 | Sundberg et al. |
| 5,932,433 | A | 8/1999 | Schatz |
| 6,255,083 | B1 | 7/2001 | Williams |
| 6,917,726 | B2 | 7/2005 | Levene et al. |
| 7,013,051 | B2 | 3/2006 | Sekiguchi et al. |
| 7,013,054 | B2 | 3/2006 | Levene et al. |
| 7,056,661 | B2 | 6/2006 | Korlach et al. |
| 7,170,050 | B2 | 1/2007 | Turner et al. |
| 7,315,019 | B2 | 1/2008 | Turner et al. |
| 7,626,704 | B2 | 12/2009 | Lundquist et al. |
| 7,745,116 | B2 | 6/2010 | Williams |
| 7,931,867 | B2 | 4/2011 | Korlach |
| 7,932,035 | B2 | 4/2011 | Korlach |
| 7,935,310 | B2 | 5/2011 | Korlach |
| 7,993,891 | B2 | 8/2011 | Roitman et al. |
| 7,995,202 | B2 | 8/2011 | Lundquist et al. |
| 8,133,672 | B2 | 3/2012 | Bjornson et al. |
| 8,137,942 | B2 | 3/2012 | Roitman et al. |
| 8,153,375 | B2 | 4/2012 | Travers et al. |
| 8,163,240 | B2 | 4/2012 | Ahn et al. |
| 8,182,993 | B2 | 5/2012 | Tomaney et al. |
| 8,193,123 | B2 | 6/2012 | Rank et al. |
| 8,207,509 | B2 | 6/2012 | Lundquist et al. |
| 8,274,040 | B2 | 9/2012 | Zhong et al. |
| 8,318,094 | B1 | 11/2012 | Bayandorian et al. |
| 8,323,939 | B2 | 12/2012 | Hanzel et al. |
| 8,324,914 | B2 | 12/2012 | Chen et al. |
| 8,367,813 | B2 | 2/2013 | Korlach |
| 8,370,079 | B2 | 2/2013 | Sorenson et al. |
| 8,461,854 | B2 * | 6/2013 | Chen .................... C12Q 1/6816 324/692 |
| 8,465,699 | B2 | 6/2013 | Fehr et al. |
| 8,465,922 | B2 | 6/2013 | Eid et al. |
| 8,467,061 | B2 | 6/2013 | McCaffrey et al. |
| 8,481,264 | B2 | 7/2013 | Bjornson et al. |
| 8,530,164 | B2 | 9/2013 | Patel et al. |
| 8,541,849 | B2 | 9/2013 | Chen |
| 8,625,091 | B2 | 1/2014 | Villeneuve |
| 8,652,779 | B2 | 2/2014 | Turner et al. |
| 8,658,364 | B2 | 2/2014 | Pham et al. |
| 8,845,880 | B2 | 9/2014 | Davis et al. |
| 8,906,831 | B2 | 12/2014 | Eid et al. |
| 8,962,242 | B2 | 2/2015 | Chen |
| 8,986,629 | B2 | 3/2015 | Deierling et al. |
| 8,986,930 | B2 | 3/2015 | Fedorov et al. |
| 8,999,676 | B2 | 4/2015 | Emig et al. |
| 9,041,420 | B2 | 5/2015 | Chen et al. |
| 9,062,091 | B2 | 6/2015 | Bjornson et al. |
| 9,116,118 | B2 | 8/2015 | Turner et al. |
| 9,121,059 | B2 | 9/2015 | Davis et al. |
| 9,121,826 | B2 | 9/2015 | Chen |
| 9,164,352 | B2 | 10/2015 | Villeneuve |
| 9,175,338 | B2 | 11/2015 | Flusbert et al. |
| 9,279,155 | B2 | 3/2016 | Bjornson et al. |
| 9,290,805 | B2 | 3/2016 | Deierling et al. |
| 9,372,308 | B1 | 6/2016 | Saxena et al. |
| 9,377,437 | B2 | 6/2016 | Chen et al. |
| 2009/0181381 | A1 | 7/2009 | Oldham et al. |
| 2010/0035254 | A1 * | 2/2010 | Williams .............. C12Q 1/6869 435/6.11 |
| 2010/0090293 | A1 * | 4/2010 | Zhang .................... B82Y 10/00 257/411 |
| 2010/0137143 | A1 | 6/2010 | Rothberg et al. |
| 2010/0169026 | A1 | 7/2010 | Sorenson et al. |
| 2010/0260465 | A1 | 10/2010 | Hanzel et al. |
| 2011/0183409 | A1 | 7/2011 | Newby et al. |
| 2011/0257040 | A1 | 10/2011 | Turner et al. |
| 2011/0257889 | A1 | 10/2011 | Klammer et al. |
| 2012/0015825 | A1 | 1/2012 | Zhong et al. |
| 2012/0021525 | A1 | 1/2012 | Fehr et al. |
| 2012/0052490 | A1 | 3/2012 | Eid et al. |
| 2013/0075703 | A1 * | 3/2013 | Gazit ..................... H01L 29/78 257/29 |
| 2013/0138358 | A1 | 5/2013 | Tang et al. |
| 2013/0285680 | A1 | 10/2013 | Sorgenfrei et al. |
| 2014/0034497 | A1 * | 2/2014 | Davis ............... G01N 27/44791 204/451 |
| 2014/0128288 | A1 | 5/2014 | Petrus |
| 2014/0235463 | A1 | 8/2014 | Rothberg et al. |
| 2014/0364324 | A1 | 12/2014 | Turner et al. |
| 2015/0011433 | A1 | 1/2015 | Miller et al. |
| 2015/0050659 | A1 | 2/2015 | Lubomir et al. |

OTHER PUBLICATIONS

Beier, M., et al., "Versatile Derivatisation of Solid Support Media for Covalent Bonding on DNA-Microchips", Nucleic Acids Res. vol. 27, No. 9, p. 1970-1-977 (1999).

Besteman K., et al., "Enzyme-Coated Carbon Nanotubes as Single-Molecule Biosensors", Nano Letters. 2003;3(6):727-30.

Bronson, J.E., et al., "Learning Rates and States from Biophysical Time Series: A Bayesian Approach to Model Selection and Single-Molecule FRET Data", Biophys J. 2009;97(12):3196-205.

Chan, et al. (2005) "Advances in Sequencing Technology" (Review) Mutation Research 573: 13-40.

Choi et al. "Single-Molecule Lysozyme Dynamics Monitored by an Electronic Circuit" Science 335, 319 (2012).

Eid et al., "Real-Time DNA Sequencing From Single Polymerase Molecules," Science (2009) 323:133-138.

Fei J., et al., "Allosteric collaboration between elongation factor G and the ribosomal L1 stalk directs tRNA movements during translation", Proceedings of the National Academy of Sciences. 2009;106(37):15702-7.

Goldsmith, B.R., et al., "Conductance-Controlled Point Functionalization of Single-Walled Carbon Nanotubes", Science. 2007;315(5808):77-81.

Goldsmith et al. "Monitoring Single-Molecule Reactivity on a Carbon Nanotube" Nano Letters. 2008;8(1):189-94.

Heller, I, et al., "Identifying the mechanism of biosensing with carbon nanotube transistors", Nano Letters. 2008;8(2): 591-5.

Hong et al., "Self-Assembly of a Dendron through Multiple Ionic Interction to Give Mesospacing between Reactive Amine Groups on the Surface", Langmuir, v. 19, No. 6, p. 2357-2365 (2003).

Huang, TcD, et al., "A 0.18-um CMOS Array Sensor for Integrated Time-Resolved Fluorescence Detection. Solid-State Circuits", IEEE Journal of. 2009;44(5):1644-54.

Johnston, M/L/, et al., "FBAR-CMOS Oscillator Array for Mass-Sensing Applications", Sensors Journal, IEEE. 2010;10(6):1042-7.

Kang, et al."High-performance electronics using dense, perfectly aligned arrays of single-walled carbon nanotubes" Nat Nano. 2007;2(4):230-6).

Kremer et al. "Broadband dielectric spectroscopy", Springer, Table of Contents, 2003.

(56) References Cited

OTHER PUBLICATIONS

Lafferty, et al. (2001) Proc. Intl. Conf. on Machine Learning 01, "Conditional Random Fields: Probabilistic Models for Segmenting and Labeling Sequence Data", pp. 282-289.
Lei, N., et al., "High-resolution extracellular stimulation of dispersed hippocampal culture with high-density CMOS multielectrode array based on non-Faradaic electrodes", Journal of neural engineering. 2011;8(4).
Levene et al., "Zero-mode Waveguides for Single-molecule Analysis at High Concentration" Science (2003) 299:682-686.
Levine, P.M., et al., "Active CMOS Sensor Array for Electrochemical Biomolecular Detection. Solid-State Circuits", IEEE Journal of. 2008;43(8):1859-71.
Levine, P.M., et al., "Real-time, multiplexed electrochemical DNA detection using an active complementary metal-oxide-semiconductor biosensor array with integrated sensor electronics", Biosensors and Bioelectronics. 2009;24(7):1995-2001.
Lu, H.P., et al., "Single-Molecule Enzymatic Dynamics", Science. 1998;282(5395):1877-82.
Mano, "Digital Logic and Computer Design", Prentice-Hall, Inc., Englewood Cliffs, N.J., 1979, Section 5-6, pp. 175-178.
Mano, "Digital Logic and Computer Design", Prentice-Hall, Inc., Englewood Cliffs, N.J., 1979, Section 6-2, pp. 204-210.
Mano, "Digital Logic and Computer Design", Prentice-Hall, Inc., Englewood Cliffs, N.J., 1979, Section 7-3, pp. 263-264.
Meric, et al. "Hybrid carbon nanotube-silicon complementary metal oxide semiconductor circuits" Journal of Vacuum Science & Technology B. 2007;25(6):2577-80.
Olsen, T.J. et al., "Electronic Measurements of Single-Molecule Processing by DNA Polymerase I (Klenow Fragment)", J Am Chem Soc. 135(21): 7855-7860 (2013).
Patounakis, et al., "Active CMOS array sensor for time-resolved fluorescence detection", IEEE Journal of Solid-State Circuits. 2006;41(11):2521-30.
Patolsky, et al., "Electrical Detection of Viruses," PNAS, 101(39), 14017, 2004.
Polk, B.J., et al., "Ag/AgCl microelectrodes with improved stability for microfluidics", Sensors and Actuators B: Chemical. 2006;114(1):239-47.
Rothberg, J.M., et al., "An integrated semiconductor device enabling non-optical genome sequencing", Nature. 2011;475(7356):348-52.
Rosenblatt, S., et al., "High performance electrolyte gated carbon nanotube transistors". Nano Letters. 2002;2(8):869-72.
Rosenstein, J.K., et al., "Integrated nanopore sensing platform with sub-microsecond temporal resolution", Nat Meth. 2012;9(5):487-92.
Schwartz D., et al., "Time-resolved Forster-resonance-energy-transfer DNA assay on an active CMOS microarray". Biosensors and Bioelectronics. 2008;24(3):383-90.
Sorgenfrei, et al. "Label-free single-molecule detection of DNA-hybridization kinetics with a carbon nanotube field-effect transistor" Nature Nanotechnology. 2011;6(2):125-31.
Sorgenfrei et al. "Debye Screening in Single-Molecule Carbon Nanotube Field-Effect Sensors" Nano Letters. 2011;11(9):3739-43.
Star, A., et al., "Label-free detection of DNA hybridization using carbon nanotube network field-effect transistors", Proc Natl Acad Sci U S A. 2006;103(4):921-6.
Van Oijen, A.M., et al., "Single-Molecule Kinetics of $\lambda$ Exonuclease Reveal Base Dependence and Dynamic Disorder", Science. 2003;301(5637):1235-8.
Wang L., Meric, et al., "One-Dimensional Electrical Contact to a Two-Dimensional Material", Science. 2013;342(6158):614-7.

\* cited by examiner

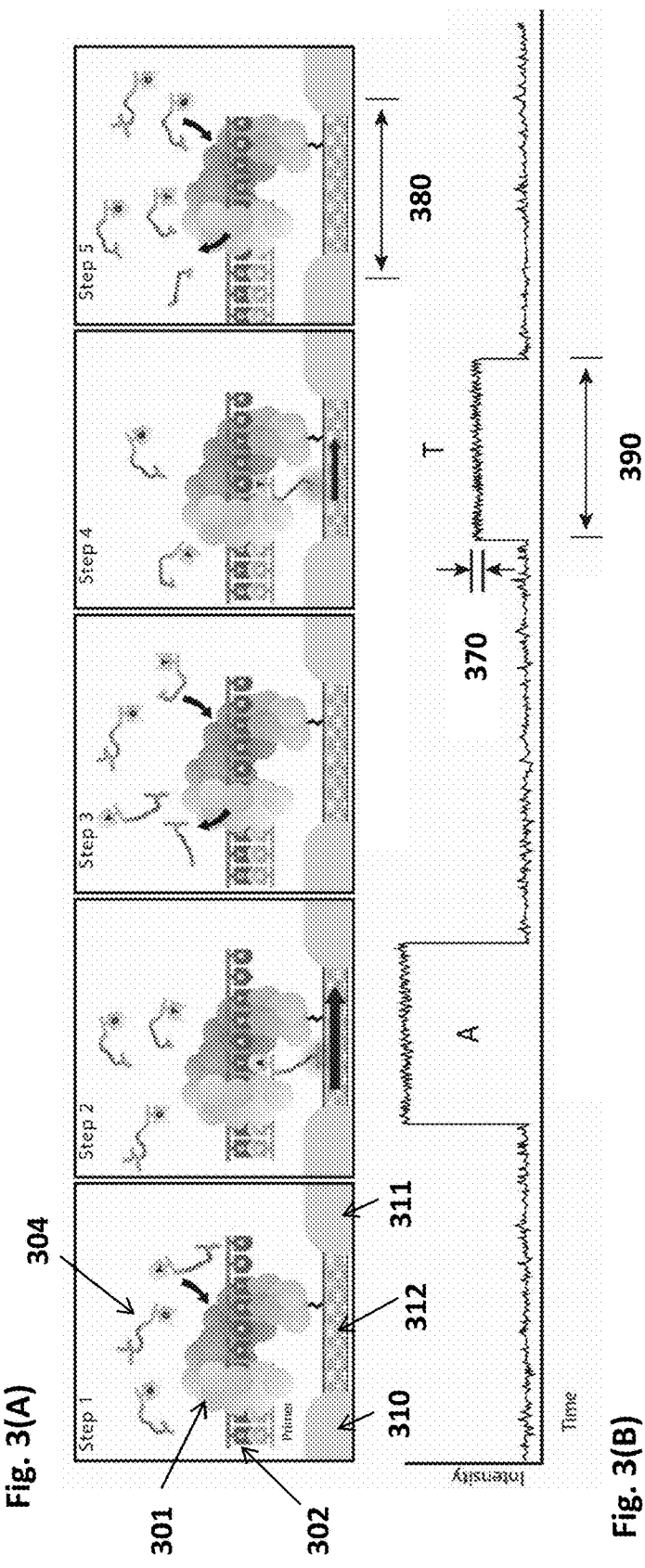

US 10,190,158 B2

SYSTEMS AND METHODS FOR SELECTIVELY ADDRESSING SPARSELY ARRANGED ELECTRONIC MEASUREMENT DEVICES

CROSS-REFERENCE TO RELATED APPLICATIONS

This application claims priority to Provisional Patent Application No. 62/201,731 entitled "Real-Time Electronic Sequencing," filed Aug. 6, 2015, and Provisional Patent Application No. 62/239,176 entitled "Single-Molecule Nanofet Sequencing Systems and Methods," filed Oct. 8, 2015, each of which is hereby incorporated herein by reference for all purposes.

STATEMENT REGARDING FEDERALLY SPONSORED RESEARCH

Not Applicable.

BACKGROUND OF THE INVENTION

Nucleic acid sequence data is valuable in myriad applications in biological research and molecular medicine, including determining the hereditary factors in disease, in developing new methods to detect disease and guide therapy (van de Vijver et al. (2002) "A gene-expression signature as a predictor of survival in breast cancer," New England Journal of Medicine 347: 1999-2009), and in providing a rational basis for personalized medicine. Obtaining and verifying sequence data for use in such analyses has made it necessary for sequencing technologies to undergo advancements to expand throughput, lower reagent and labor costs, and improve accuracy (See, e.g., Chan, et al. (2005) "Advances in Sequencing Technology" (Review) Mutation Research 573: 13-40 which is incorporated herein in its entireties for all purposes.

Various methods of sequencing are used and each has its strengths and weaknesses. Single molecule real time sequencing has advantages over other sequencing methodologies including the ability to provide longer read lengths. Many current methods of sequencing use optical labels. There is a need for improved sequencing instruments and methods that use non-optical readouts, and in particular real time single molecule sequencing methods with these characteristics.

Electronic detection of single molecules and single particles, including by capacitive, impedance, and conductive methods has been demonstrated. The current invention provides instruments, devices and methods for non-optical real-time single molecule sequencing.

BRIEF SUMMARY OF THE INVENTION

In some aspects, the invention provides cost effective systems and methods for addressing low yield nano-electronic measurement devices. A method for nucleic acid sequencing comprising: providing a substrate comprising an array of nano-electronic measurement devices (e.g., nanoscale field effect transistors (nanoFETs)) capable of measuring electrical changes due to molecular interactions, where a plurality of the devices have a single polymerase enzyme complex.

In some aspects, the invention provides methods for nucleic acid sequencing comprising: providing a substrate comprising an array of nano-electronic measurement devices (e.g., nanoFETs), each comprising a source, a drain, a gate, and a channel and wherein a plurality of the devices comprise a single polymerase enzyme complex comprising a polymerase enzyme and a template nucleic acid, the complex attached to gate of the device, and where the polymerase enzyme is attached to the channel in an orientation whereby the nucleotide exit region of the polymerase enzyme is toward the channel of the nanoFET; exposing the substrate to a plurality of types of nucleotide analogs, each comprising a different charge label attached to the phosphate portion of the nucleotide analog through a linker under conditions whereby polymerase mediated nucleic acid synthesis occurs, resulting in cleavage of the charge label and the growth of a nascent nucleic acid strand; applying a voltage between the source and drain, whereby when a nucleotide analog resides in the active site of the enzyme, the charge label on the nucleotide analog produces a measurable change in the electrical signal at the gate; monitoring an electrical signal at the gate over time, whereby the electrical signal indicates an incorporation event for a type of nucleotide analog having a specific charge label; and using the electrical signal to determine a sequence of the template nucleic acid.

In some embodiments the electrical signal used to determine the sequence of the template nucleic acids includes the duration of the signal indicating the residence time of a nucleotide analog in the active site of a polymerase. In some embodiments the channel of each device comprises a nanowire. In some embodiments the channel of each device comprises a carbon nanotube. In some embodiments the electrical signal is a resistance and/or conductance across the channel, a current through the channel, a voltage potential across the channel, or an AC impedance across the channel. In some embodiments an AC voltage is applied across the channel, between the source and the drain, and the frequency of the AC voltage is changed with time.

In some embodiments the substrate is exposed to four types of nucleotide analogs corresponding to A, G, C, T, or A, G, C, U, each of the four types of nucleotide analogs having a different charge label. In some embodiments the charge label comprises a protein. In some embodiments the protein has a molecular weight that is between $1/10$ and 3 times the molecular weight of the polymerase enzyme. In some embodiments the protein has a molecular weight that is between $1/10$ and 3 times the molecular weight of a phi29 polymerase.

In some embodiments the polymerase is attached to the nano-electronic measurement device through a linker at a single point on the polymerase that is within 50 angstroms of the nucleotide exit region of the enzyme. In some embodiments the polymerase is a phi29-type polymerase and the polymerase is attached through a linker to the nano-electronic measurement device at a single point on the polymerase that is within five amino acids from position 375 or position 512. In some embodiments the polymerase is modified phi29 polymerase.

In some embodiments the polymerase is attached through two linkers at two different positions on the polymerase to the nano-electronic measurement device, where at least one linker is attached to a position that is within 50 Angstroms of the nucleotide exit region of the enzyme. In some embodiments the polymerase is attached to the nano-electronic measurement device through two linkers at two different positions on the polymerase, where both linkers are attached to positions that are within 50 Angstroms of the nucleotide exit region of the enzyme. In some embodiments the polymerase is attached to the nano-electronic measurement device through an adaptor that attaches to the polymerase at two different positions that are within 50 Angstroms of the nucleotide exit region of the enzyme, and the adaptor is attached to a single point on the channel of the nano-electronic measurement device.

In some embodiments at least one of the charge labels comprises a polymer chain having multiple charges. In some embodiments there are four types of nucleotide analogs and each comprises a charge label comprising a polymer chain having multiple charges. In some embodiments there are four types of nucleotide analogs and each comprises a charge label having a different number of negative charges. In some embodiments there are four types of nucleotide analogs and each comprises a charge label having a different number of positive charges. In some embodiments there are four types of nucleotide analogs and each comprises a charge label having both negative and positive charges and each has a different net charge. In some embodiments there are four types of nucleotide analogs and two labels have a net negative charge, and two labels have a net positive charge.

In some embodiments there are four types of nucleotide analogs and two of the labels result in a first characteristic change in an electrical signal associated with the devices when their corresponding nucleotide analog is associated with the polymerase, and two of the labels result in a second characteristic change in an electrical signal associated with the device when their corresponding nucleotide analog is associated with the polymerase. As a non-limiting example, in some embodiments two of the labels result in a characteristic increase in voltage across the channels of the devices when their corresponding nucleotide analog is associated with the polymerase, and two of the labels result in a characteristic decrease in voltage across the channels of the devices when their corresponding nucleotide analog is associated with the polymerase.

In some aspects the invention provides a chip for sequencing a plurality of single nucleic acid template molecules comprising: a substrate comprising; a plurality of nano-electronic measurement devices (e.g., nanoFET devices), each comprising a source, a drain, a channel, and a gate and a single polymerase enzyme complex bound to the channel of the device, where the polymerase enzyme complex comprises a polymerase enzyme and a template nucleic acid, where the polymerase enzyme is attached to the channel in an orientation whereby the nucleotide exit region of the polymerase enzyme is toward the channel of the device; where the substrate is configured such that the device comes into contact with a sequencing reaction mixture comprising a plurality of types of nucleotide analogs each having different charge labels; and a plurality of electrical connection sites for bringing current and voltage to the devices, and for receiving electrical signals from the devices.

In some embodiments the channel of each device comprises a nanowire. In some embodiments, the channel of each device comprises a carbon nanotube. In some embodiments the substrate comprises greater than 1,000 devices. In some embodiments the substrate comprises greater than 10,000 devices. In some embodiments the substrate comprises about 1,000 devices to about 10 million devices. In some embodiments, the substrate comprises about 10,000 devices to about 1 million devices.

In some embodiments the substrate comprises electronic elements for one or more of: providing electrical signals to the devices, measuring the electrical signals at the devices, analog to digital conversion, signal processing, and data storage. In some embodiments the electrical elements are CMOS elements. In some embodiments the charge label is attached through a linker at a single point on the polymerase that is within 50 angstroms of the nucleotide exit region of the enzyme. In some embodiments the polymerase is a phi29-type polymerase and the charge label is attached through a linker at a single point on the polymerase that is within 5 amino acids from position 375 or position 512. In some embodiments the polymerase is modified phi29 polymerase.

In some embodiments the charge label is attached through two linkers at two different positions on the polymerase, where at least one is attached to a position that is within 50 angstroms of the nucleotide exit region of the enzyme. In some embodiments the charge label (e.g., a charge label that is a protein) is attached through two linkers at two different positions on the polymerase, where both linkers are attached to positions that are within 50 angstroms of the nucleotide exit region of the enzyme.

In some embodiments the charge label is attached through an adaptor that attaches to the polymerase at two different positions that are within 50 angstroms of the nucleotide exit region of the enzyme, and the adaptor is attached to a single point on the channel of the measurement device.

In some aspects, the invention provides a system for sequencing template nucleic acids comprising: a housing having housing electrical connection sites; a chip that reversibly mates with the housing comprising a substrate comprising: chip electrical connection sites that reversibly connect to the housing electrical connection sites, a plurality of nano-electronic measurement devices (e.g., nanoFETs), each measurement device comprising a source, a drain, a channel, and a gate, and a single polymerase enzyme complex bound to the channel, where the polymerase enzyme complex comprises a polymerase enzyme and a template nucleic acid, where the polymerase enzyme is attached to the channel in an orientation whereby the nucleotide exit region of the polymerase enzyme is toward the channel of the measurement device; a fluid reservoir for contacting a sequencing reaction mixture with the measurement devices, the sequencing reaction mixture comprising a plurality of types of nucleotide analogs, each having a different charge label, where the charge labels are sensed by the measurement device while an analog is associated with the polymerase enzyme complex; an electronic control system electrically connected to the measurement devices through the electrical connections to apply desired electrical signals to the measurement devices and for receiving electrical signals from the measurement devices; and a computer that receives information on the electrical signals at the measurement device over time and uses such information to identify a sequence of the template nucleic acid.

In some embodiments the channel of each measurement device comprises a nanowire. In some embodiments the channel of each measurement devices comprises doped silicon. In some embodiments the substrate comprises greater than 1,000 measurement devices. In some embodiments the substrate comprises greater than 10,000 measurement devices. In some embodiments the substrate comprises about 1,000 measurement devices to about 10 million measurement devices. In some embodiments the substrate comprises about 10,000 measurement devices to about 1 million measurement devices.

In another some embodiments the substrate comprises electronic elements for one or more of: providing electrical signals to the measurement devices, measuring the electrical signals at the measurement devices, analog to digital conversion, signal processing, and data storage. In some embodiments the electrical elements are CMOS elements.

Another aspect of the present disclosure provides a circuit comprising a substrate with sectors on the substrate. Each sector comprises clock and data lines, a programmable switch controller in electrical communication with the clock and data lines, a counter bias line, an amplifier input line and nano-electronic measurement devices on the substrate. A source of each device is coupled to the counter bias line and a drain of each device is coupled to the amplifier input line to obtain an electrical signal on the drain, the identity of which is determined by electrical interaction (e.g., electrostatic interaction) between the device and a charge label. Each device drain is gated by a corresponding switch between an on state, in which the drain is connected to the amplifier input line, and an off state, in which the drain is isolated from the amplifier input line. The controller controls switch states responsive to clock signal line pulses and data input line data.

Still another aspect provides an integrated circuit comprising a substrate and a plurality of sectors arranged on the substrate. Each sector in the plurality of sectors comprises a programmable switch controller, a counter bias line, an amplifier input line, and a plurality of nano-electronic measurement devices spatially arranged on the substrate. Each respective nano-electronic measurement device in the plurality of nano-electronic measurement devices includes a source that is coupled to the counter bias line and a drain that is coupled to the amplifier input line thereby obtaining an electrical signal on the drain of the respective nano-electronic measurement device. This electrical signal is any one of a discrete set of electrical signals, an identity of the electrical signal in the discrete set of electrical signals is determined by an electrical interaction between the corresponding nano-electronic measurement device and a particular charge label in a plurality of charge labels. Each sector in the plurality of sectors further comprises a plurality of switches. Each switch in the plurality of switches gates the electrical signal between the drain of a corresponding nano-electronic measurement device in the plurality of nano-electronic measurement devices and the amplifier input line between (i) an on state, in which the electrical signal at the drain of the corresponding nano-electronic measurement device is delivered to the amplifier input line, and (ii) an off state, in which the electrical signal at the drain of the corresponding nano-electronic measurement device is not delivered to the amplifier input line. Each respective switch in the plurality of switches is independently wired to the programmable switch controller thereby causing the respective switch to be in one of the on state and the off state responsive to the programmable switch controller.

Some embodiments of the integrated circuit provide scan chain addressing. In such embodiments, each sector in the plurality of sectors further comprises a first clock signal line and a data input line. In such embodiments, the programmable switch controller of a sector in the plurality of sectors comprises a first shift register comprising a first plurality of flip-flops in electrical communication with the first clock signal line. The first plurality of flip-flops comprises an initial flip-flop and a terminal flip-flop. Each flip-flop includes a clock pulse input, a serial input and a serial output, where the serial output of each flip-flop in the first plurality of flip-flops, other than the terminal flip-flop, is uniquely electrically connected to the serial input of another flip-flop in the first plurality of flip-flops, thereby electrically coupling the first plurality of flip-flops in series. The serial input of the initial flip-flop is electrically connected to the data input line, where the first shift register is configured to receive a device scan chain sequence, from the data input line, that is propagated through the first plurality of flip-flops by electrical pulses in the first clock signal line that is connected to clock pulse input of each flip-flop in the plurality of first flip-flops, thereby independently biasing each flip-flop in the first plurality of flip-flops to one of a first state and a second state. Each respective switch in the plurality of switches is independently wired to the programmable switch controller through a corresponding flip-flop in the first plurality of flip-flops thereby causing the respective switch to be in the off state when the corresponding flip-flop is biased to the first state and causing the respective switch to be in the on state when the corresponding flip-flop is biased to the second state.

Some embodiments of the integrated circuit provide shunt scan addressing. In such embodiments, a sector in the plurality of sectors further comprises a shunt scan chain input line, a shunt clock signal line, and a first plurality of AND gates. The programmable switch controller further comprises a second shift register comprising a second plurality of flip-flops in electrical communication with the shunt clock signal line. The second plurality of flip-flops comprises an initial flip-flop and a terminal flip flop. Each flip-flop in the second plurality of flip-flops includes a serial input and a serial output, where the serial output of each flip-flop in the second plurality of flip-flops, other than the terminal flip-flop, is uniquely electrically connected to the serial input of another flip-flop in the second plurality of flip-flops, thereby electrically coupling the second plurality of flip-flops in series. The serial input of the initial flip-flop in the second plurality of flip-flops is electrically connected to the shunt scan chain input line, where the second shift register is configured to receive a shunt scan chain sequence that is propagated through the second plurality of flip-flops by electrical pulses in the shunt clock signal line, thereby independently biasing each flip-flop in the second plurality of flip-flops to one of a third state and a forth state. The programmable switch controller further comprises a plurality of multiplexers, where each multiplexer in the plurality of multiplexers includes a first input line, a second input line, a select line, and an output line. The first input line of each respective multiplexer in the plurality of multiplexers is in electrical communication with the serial output of a first corresponding flip-flop in the first plurality of flip-flops. The second input line of each respective multiplexer in the plurality of multiplexers is in electrical communication with the serial input of the first corresponding flip-flop in the first plurality of flip-flops. The select line of each respective multiplexer in the plurality of multiplexers is in electrical communication with the serial output of a first corresponding flip-flop in the second plurality of flip-flops. The output line of each respective multiplexer in the plurality of multiplexers is in electrical communication with the serial input of a second corresponding flip-flop in the first plurality of flip-flops. Moreover, each AND gate in the first plurality of AND gates comprises an output, a first input and a second input. The first input of each respective AND gate in the first plurality of AND gates is in electrical communication with the first clock signal line. The second input of each respective AND gate in the first plurality of AND gates is in electrical communication with the serial output of the first corresponding flip-flop in the second plurality of flip-flops. Each respective flip-flop in the first plurality of flip-flops is in electrical communication with the first clock signal line through the output of a corresponding AND gate in the first plurality of AND gates. When a respective flip-flop in the second plurality of flip-flops, that is in electrical communication with the second input of the respective AND gate, is in the third state, the first clock signal line is not applied to the respective flip-flop in the first plurality of flip-flops and the select line of the multiplexer in the plurality of multiplexers that is in electrical communication with the output of the respective flip-flop in the second plurality of flip-flops is biased to the second input line of the respective multiplexer. When the flip-flop in the second plurality of flip-flops, that is in electrical communication with the second input of the respective AND gate, is in the fourth state, the first clock signal line is applied to the respective flip-flop in the first plurality of flip-flops and the select line of the multiplexer in the plurality of multiplexers that is in electrical communication with the output of the respective flip-flop in the second plurality of flip-flops is biased to the first input line of the respective multiplexer. In some such embodiments, the output line of each respective multiplexer in the plurality of multiplexers is in electrical communication with the serial input of a second corresponding flip-flop in the first plurality of flip-flops through a corresponding buffer gate in plurality of buffer gates.

Some embodiments of the integrated circuit provide shunt scan chain addressing with a shunt signal. In such embodiments, each flip-flop in the first plurality of flip-flops further comprises a first reset. Each flip-flop in the second plurality of flip-flops further comprises a second reset. Further, the sector further comprises a shunt signal line. The programmable switch controller further comprises a second plurality of AND gates, where each AND gate in the second plurality of AND gates has an output, a first input and a second input. The first input of each respective AND gate in the second plurality of AND gates is in electrical communication with the serial output of a first flip-flop in the first plurality of flip-flops. The second input of each respective AND gate in the second plurality of AND gates is in electrical communication with the shunt signal line. The output of each respective AND gate in the second plurality of AND gates is in electrical communication with the first reset of the corresponding flip-flop in the first plurality of flip-flops and the second reset of a corresponding flip-flop in the second plurality of flip-flops, thereby causing the first corresponding flip-flop to reset to the first state and the second corresponding flip-flop to reset to the third state when the shunt signal line is asserted at the same time that the data input line drives the corresponding flip-flop in the first plurality of flip-flop to the second state.

Some embodiments of the integrated circuit provide row/column addressing. In some such embodiments, the switch controller of a sector in the plurality of sectors comprises a memory controller, a memory in electrical communication with the memory controller, a column decoder in electrical communication with the memory, and a row decoder in electrical communication with the memory. Further, the sector further comprises a plurality of AND gates, where each AND gate in the plurality of AND gates comprises an output, a first input and a second input. The first input of each respective AND gate in the plurality of AND gates is in electrical communication with the column decoder. The second input of each respective AND gate in the plurality of AND gates is in electrical communication with the row decoder. Each respective switch in the plurality of switches is independently wired to the switch controller thereby causing the respective switch to be in the on state when the row decoder and the column decoder both signal a first state to the respective switch and otherwise causing the respective switch to be in the off state.

In another aspect of the present disclosure each the sector further comprises a first clock line, a data input line, a second clock line, and a restart scan chain line. Further, in such embodiments, the programmable switch controller of a sector in the plurality of sectors comprises a row shift register comprising a first plurality of flip-flops. An initial flip-flop in the first plurality of flip-flops is in electrical communication with the data input line and the first clock signal line. The a row shift register further comprises a plurality of AND gates. Each AND gate in the plurality of AND gates comprises a first input, a second input and an output. Each sector further comprises a plurality of column shift registers. Each column shift register comprises a second plurality of flip-flops. The first input of each AND gate in the plurality of AND gates is in electrical communication with an output of a corresponding flip-flop in the first plurality of flip-flops of the row shift register. The second input of each AND gate in the plurality of AND gates is in electrical communication with the second clock line. The respective second plurality of flip-flops of each respective column shift register in the plurality of column shift registers comprises an initial flip-flop and a terminal flip-flop. Each flip-flop in the respective second plurality of flip-flops includes a serial data input, a clock pulse input, and a serial data output. The serial data output of each respective flip-flop in the second plurality of flip-flops, other than the terminal flip-flop, is uniquely electrically connected to the serial data input of another flip-flop in the second plurality of flip-flops, thereby electrically coupling the second plurality of flip-flops in series. The clock pulse input of each flip-flop in the second plurality of flip-flops is electrically connected to the output of an AND gate in the first plurality of AND gates. Each respective column shift register in the plurality of column shift registers is configured to receive a logical "1" or "0" from the restart scan chain line that is propagated from the initial flip-flop in the second plurality of flip-flops through the second plurality of flip-flops by electrical pulses received at the clock pulse input of each respective flip-flop in the second plurality of flip-flops thereby independently biasing each flip-flop in the second plurality of flip-flops to one of the first state and the second state. Each respective switch in the plurality of switches is independently wired to the programmable switch controller through the output of a corresponding flip-flop in the second plurality of flip-flops of a corresponding column shift register, thereby causing the respective switch to: be in the off state when the corresponding flip-flop in the second plurality of flip-flops of the corresponding column shift register is biased to a first state, and be in the on state when the corresponding flip-flop in the second plurality of flip-flops of the corresponding column shift register is biased to the second state.

In another aspect of the present disclosure, each the sector further comprises a first clock line, a data input line, a second clock line, a load buffer line, and a restart scan chain line. In such embodiments, the programmable switch controller of a sector in the plurality of sectors comprises a row shift register comprising a first plurality of flip-flops, where an initial flip-flop in the first plurality of flip-flops is in electrical communication with the data input line and the first clock signal line. A plurality of AND gates, each AND gate in the plurality of AND gates comprising a first input, a second input, and an output. Each sector in the plurality of sectors further comprises a plurality of column shift registers. Each column shift register comprises a second plurality of flip-flops and a third plurality of flip-flops. The first input of each AND gate in the first plurality of AND gates is in electrical communication with an output of a corresponding flip-flop in the first plurality of flip-flops of the row shift register. The second input of each AND gate in the first plurality of AND gates is in electrical communication with the second clock line. The respective second plurality of flip-flops of each respective column shift register in the plurality of column shift registers comprises an initial flip-flop and a terminal flip-flop. Each flip-flop in the respective second plurality of flip-flops includes a serial data input, a clock pulse input, and a serial data output. The serial data output of each respective flip-flop in the second plurality of flip-flops, other than the terminal flip-flop, is uniquely electrically connected to the serial data input of another flip-flop in the second plurality of flip-flops, thereby electrically coupling the second plurality of flip-flops in series. The clock pulse input of each flip-flop in the second plurality of flip-flops is electrically connected to the output of an AND gate in the first plurality of AND gates. Each respective column shift register in the plurality of column shift registers is configured to receive a logical "1" or "0" from the restart scan chain line that is propagated from the initial flip-flop in the second plurality of flip-flops through the second plurality of flip-flops by electrical pulses received at the clock pulse input of each respective flip-flop in the second plurality of flip-flops thereby independently biasing each flip-flop in the second plurality of flip-flops to one of the first state and the second state. Each respective flip-flop in the third plurality of flip-flops comprises a data input, a data output and a clock pulse input. The clock pulse input of each respective flip-flop in the third plurality of flip-flops is electrically connected to the load buffer line, the data input of each respective flip-flop gate in the third plurality of flip-flops is wired to the output of a corresponding flip-flop in the second plurality of flip-flops, thereby causing the state of the corresponding flip-flop in the third plurality of flip-flops to be biased to the first state when the corresponding flip-flip in the second plurality of flip-flops is biased to the first state and the load buffer line is asserted, and the state of the corresponding flip-flop in the third plurality of flip-flops to be biased to the second state when the corresponding flip-flip in the second plurality of flip-flops is biased to the second state and the load buffer line is asserted. Each respective switch in the plurality of switches is independently wired to the programmable switch controller through the output of a corresponding flip-flop in the third plurality of flip-flops of a corresponding column shift register, thereby causing the respective switch to be in the off state when the corresponding flip-flop in the third plurality of flip-flops of the corresponding column shift register is biased to the first state, and be in the on state when the corresponding flip-flop in the third plurality of flip-flops of the corresponding column shift register is biased to the second state.

In some embodiments a nano-electronic measurement device in the plurality of nano-electronic measurement devices is a nanoFET that comprises the source, the drain, a gate, and a channel and where the input from the counter bias line is applied from the source to the drain across the channel. In some such embodiments, the channel is a nanowire, a carbon nanotube, or a graphene nanoribbon. In some such embodiments, the channel is a nanopore.

In some embodiments the counter bias line carries a DC voltage and the application of the counter bias line to the nano-electronic measurement device results in a DC current in the channel of the nano-electronic measurement device.

In some embodiments the counter bias line carries an AC voltage and a frequency of the AC voltage is changed with time during application of the counter bias line to the nano-electronic measurement device.

In some embodiments each charge label in the plurality of charge labels represents a different type of nucleotide analog in a plurality of nucleotide analogs. In some embodiments a polymerase enzyme is attached to the corresponding nano-electronic measurement device and the particular charge label that forms an electrical interaction with the corresponding nano-electronic measurement device is freed from a corresponding nucleotide analog in the plurality of nucleotide analogs by the polymerase enzyme as part of a polymerase mediated nucleic acid synthesis reaction with a template nucleic acid. In some such embodiments a charge label in the plurality of charge labels comprises a protein. In some embodiments the protein has a molecular weight that is between $1/10$ and 3 times the molecular weight of the polymerase enzyme. In some such embodiments the protein has a molecular weight that is between $1/10$ and 3 times the molecular weight of a phi29 polymerase.

In some embodiments at least one of the charge labels in the plurality of charge labels comprises a polymer chain characterized by multiple charges.

In some embodiments each charge label in the plurality of charge labels comprises a polymer chain characterized by a unique net positive or negative charge. In some embodiments a first charge label in the plurality of charge labels comprises a first polymer chain having a unique net positive charge, and a second charge label in the plurality of charge labels comprises a second polymer chain having a unique net negative charge. In some embodiments the plurality of nano-electronic measurement devices of a sector in the plurality of sectors are arranged as a row or a column on the substrate. In some embodiments the plurality of nano-electronic measurement devices of a sector in the plurality of sectors are arranged as a plurality of rows or a plurality of columns on the substrate.

In some embodiments the circuit further comprises plurality of amplifiers, where each amplifier in the plurality of amplifiers is in electrical communication with the amplifier input line of a corresponding sector in the plurality of sectors. In some such embodiments, an amplifier in the plurality of amplifiers is a current-to-voltage amplifier.

In some embodiments, the plurality of nano-electronic measurement devices comprises 1,000 nano-electronic measurement devices. In some embodiments, the plurality of nano-electronic measurement devices comprises 10,000 nano-electronic measurement devices. In some embodiments, the plurality of nano-electronic measurement devices consists of between 1,000 nano-electronic measurement devices and 10 million nano-electronic measurement devices. In some embodiments, the plurality of measurement devices consists of between 10,000 nano-electronic measurement devices and 1 million nano-electronic measurement devices.

Another aspect of the present disclosure provides a measurement device comprising one or more processors, a memory, a measurement array stored in the memory, an integrated circuit comprising a plurality of individually addressable nano-electronic measurement devices in electronic communication with a counter bias line, where an operational state of the integrated circuit is controlled by the clock signal line; and one or more programs. The one or more programs are stored in the memory and are configured to be executed by the one or more processors, the one or more programs including instructions for driving the measurement array into the integrated circuit. The measurement array determines which nano-electronic measurement devices in the plurality of individually addressable nano-electronic measurement devices are responsive to the counter bias line. The one or more programs including instructions for driving the counter bias line to an operational state. The one or more programs including instructions for, responsive to respective clock signals on the clock signal line, individually obtaining a read from each nano-electronic measurement device in the plurality of nano-electronic measurement devices that is deemed responsive to the counter bias line by the measurement array. The one or more programs including instructions for storing each obtained read in the memory.

In some embodiments, the integrated circuit comprises a first shift register comprising a first plurality of flip-flops. Each flip-flop in the plurality of flip-flops is in electrical communication with a corresponding nano-electronic measurement device in the plurality of individually addressable nano-electronic measurement devices.

In some such embodiments, the driving the measurement array into the integrated circuit comprises loading individual elements of the measurement array into individual flip-flops in the plurality of flip-flops by electrical pulses in the clock signal line thereby determining which flip-flops in the first plurality of flip-flops are biased to a first state and which flip-flops in the first plurality of flip-flops are biased to a second state. A respective nano-electronic measurement device is deemed responsive to the counter bias line when the corresponding flip-flop in electrical communication with the respective nano-electronic measurement device is in the on state, and a respective nano-electronic measurement device is deemed non-responsive to the counter bias line when the corresponding flip-flop in electrical communication with the respective nano-electronic measurement device is in the off state.

In some such embodiments, the integrated circuit comprises a memory controller, an integrated circuit memory in electrical communication with the memory controller, a column decoder in electrical communication with the integrated circuit memory, and a row decoder in electrical communication with the integrated circuit memory. Further, the driving the measurement array into the integrated circuit comprises loading the measurement array into the integrated circuit memory, and each respective nano-electronic measurement device in the plurality of nano-electronic measurement devices is independently wired to the column decoder and the row decoder through a corresponding AND gate in a plurality of AND gates thereby causing the respective nano-electronic measurement device to be deemed responsive to the counter bias line when the row decoder and the column decoder both signal a first state to the corresponding AND and otherwise cause the respective nano-electronic measurement device to be deemed non-responsive to the counter bias line.

In some such embodiments, a nano-electronic measurement device in the plurality of nano-electronic measurement devices is a nanoFET that comprises a source, a drain, a gate, and a channel and where the input from the counter bias line is applied from the source to the drain across the channel. In some embodiments, the channel is a nanowire, a carbon nanotube, or a graphene nanoribbon. In some embodiments, the channel is a nanopore. In some embodiments, the counter bias line carries a DC voltage. In some embodiments, the counter bias line carries an AC voltage and a frequency of the AC voltage is changed with time.

In some embodiments, the read from a nano-electronic measurement device in the plurality nano-electronic measurement devices is an electrical signal that is any one of a discrete set of electrical signals, where an identity of the electrical signal in the discrete set of electrical signals is determined by an electrical interaction between the corresponding nano-electronic measurement device and a particular charge label in a plurality of charge labels. In some such embodiments, each charge label in the plurality of charge labels represents a different type of nucleotide analog in a plurality of nucleotide analogs. In some such embodiments, a polymerase enzyme is attached to the corresponding nano-electronic measurement device and the particular charge label that forms an electrical interaction with the corresponding nano-electronic measurement device is freed from a corresponding nucleotide analog in the plurality of nucleotide analogs by the polymerase enzyme as part of a polymerase mediated nucleic acid synthesis reaction with a template nucleic acid. In some embodiments, a charge label in the plurality of charge labels comprises a protein. In some such embodiments, the protein has a molecular weight that is between $\frac{1}{10}$ and 3 times the molecular weight of the polymerase enzyme. In some such embodiments, the protein has a molecular weight that is between $\frac{1}{10}$ and 3 times the molecular weight of a phi29 polymerase.

In some embodiments, at least one of the charge labels in the plurality of charge labels comprises a polymer chain characterized by multiple charges. In some such embodiments, each charge label in the plurality of charge labels comprises a polymer chain characterized by a unique net positive or negative charge.

In some embodiments, a first charge label in the plurality of charge labels comprises a first polymer chain having a unique net positive charge, and a second charge label in the plurality of charge labels comprises a second polymer chain having a unique net negative charge.

In some embodiments, the plurality of nano-electronic measurement devices comprises 1,000 nano-electronic measurement devices, comprises 10,000 nano-electronic measurement devices, consists of between 1,000 nano-electronic measurement devices and 10 million nano-electronic measurement devices, or consists of between 10,000 nano-electronic measurement devices and 1 million nano-electronic measurement devices.

Another aspect of the present disclosure comprises an integrated circuit that, in turn, comprises a substrate and a plurality of sectors arranged on the substrate. Each sector in the plurality of sectors comprises a programmable switch controller, a sector input line, a sector output line, and a plurality of measurement devices spatially arranged on the substrate. Each respective measurement device in the plurality of measurement devices is electrically coupled to the sector input line and to the sector output line. Each sector further comprises a plurality of switches. Each respective switch in the plurality of switches gates a corresponding measurement device in the plurality of measurement devices between (i) an on state, in which an electrical measurement signal of the corresponding measurement device is delivered to the sector output line, and (ii) an off state, in which the electrical measurement signal of the corresponding measurement device is not delivered to the sector output line. Each respective switch in the plurality of switches is independently wired to the programmable switch controller thereby causing the respective switch to be in one of the on state and the off state responsive to the programmable switch controller and wherein the plurality of switches is configured to cause a subset of the measurement devices in the plurality of measurement devices to be in the on state at any given time. In some embodiments, the subset of the measurement devices is a single measurement device. In some embodiments, the subset of the measurement devices is two measurement devices, three measurements or any number of measurement devices less than the plurality of measurement devices.

In some embodiments, each respective measurement device in the plurality of measurement devices comprises a source, a drain, and a gate and the respective sector further comprises a gate line. In such some such embodiments, the sector input line is connected to the source of each respective measurement device in the plurality of measurement devices. Further, the sector output line is connected to the drain of each respective measurement device in the plurality of measurement devices, and each respective switch in the plurality of switches gates the gate line to the gate of the corresponding measurement device in the plurality of measurement devices.

In some alternative embodiments, each respective measurement device in the plurality of measurement devices comprises a source and a drain, and the sector input line is connected to the source of each respective measurement device in the plurality of measurement devices. Further, the sector output line is connected to the drain of each respective measurement device in the plurality of measurement devices, and each respective switch in the plurality of switches gates the sector input line to the source of the corresponding measurement device in the plurality of measurement devices.

In some alternative embodiments, each respective measurement device in the plurality of measurement devices comprises a source and a drain, and the sector input line is connected to the source of each respective measurement device in the plurality of measurement devices. In such embodiments, the sector output line is connected to the drain of each respective measurement device in the plurality of measurement devices, and each respective switch in the plurality of switches gates the sector output line to the drain of the corresponding measurement device in the plurality of measurement devices.

BRIEF DESCRIPTION OF THE DRAWINGS

FIG. 1A, FIG. 1B, and FIG. 1C show various stages of the sequencing reaction.

FIG. 3 provides another illustration of the nano-electronic measurement device sequencing method. FIG. 3(A) illustrates the reaction at the polymerase enzyme, and FIG. 3(B) illustrates the measurement of electrical signal versus time during the sequencing reaction.

FIG. 4 illustrates methods of orienting a polymerase for increased sensitivity in nano-electronic measurement device sequencing.

DETAILED DESCRIPTION OF THE INVENTION

Figure 1:
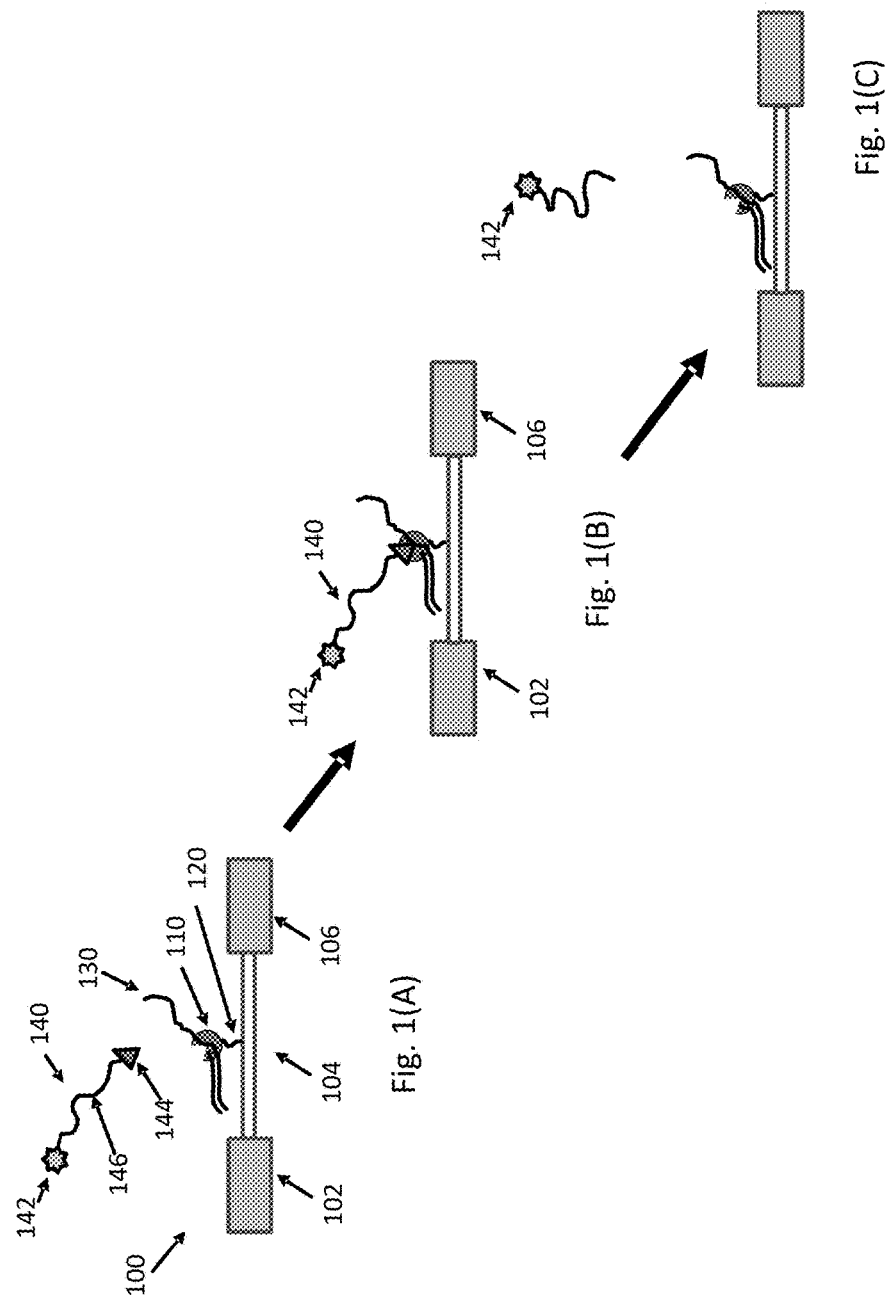
FIG. 1 illustrates a method of the invention for sequencing using a nano-electronic measurement device.

In some aspects, the invention provides methods, devices, systems, and compositions of matter directed to single-molecule real-time electronic sequencing. The electronic detection can performed using with a nano-electronic measurement device (e.g, a nanoscale field effect transistor herein termed a nanoFETs), where the nano-electronic measurement devices are sensitive to molecular interactions in the vicinity of the channel of the devices. In some aspects a single polymerase-template complex is immobilized on or proximate to the channel of a nano-electronic measurement device, and the electrical signal from the nano-electronic measurement device is used for determining a nucleic acid sequence. The nano-electronic measurement devices of the invention typically have a nanoscale channel that comprises a nanowire such a carbon nanotube.

Typically four nucleotide analogs, each having a different distinguishable charge label, are present. The term charge label is used to designate a label that will produce a change in the electrical signal at a nano-electronic measurement device. In some cases, this change in electrical signal is due to a change in the voltage across the channel of the nano-electronic measurement device or a change in the current through the channel of the nano-electronic measurement device, but the change in electrical signal can include other aspects as described in more detail below. The charge label is typically connected to the nucleotide analog through the phosphate portion of the nucleotide analog such that when the nucleotide analog is incorporated by the polymerase enzyme into a growing nascent nucleic acid strand, the label is released. The charge label is typically connected to the nucleotide portion of the analog through a linker. When the nucleotide analog is held in the polymerase enzyme active site during the incorporation reaction, the charge label produces a change in an electrical parameter of the nano-electronic measurement device. The change in electrical signal, such as voltage across the channel, current through the channel, or impedance of the channel (in the case of an AC voltage to the measurement device), can be used to determine the presence and the identity of the nucleotide analog that is in the active site of the polymerase enzyme. The electrical characteristics of the nano-electronic measurement device while a particular nucleotide type is in the active site will be different than the case when other nucleotide type is are in the active site. Because the nucleotide of a particular nucleotide type is held close to the channel of the nano-electronic measurement device during the incorporation process by the enzyme, it is held in place long enough for a characteristic electrical parameter value associated with the interaction of the nucleotide type with the nano-electronic measurement device to be determined in order to detect the presence of the nucleotide and also to identify which type of nucleotide is being incorporated.

Suitable arrays for the instant invention are described in U.S. Patent Application entitled "SINGLE-MOLECULE NANOFET SEQUENCING SYSTEMS AND METHODS" filed on Aug. 3, 2016, which is incorporated herein by reference for all purposes. In particular, suitable arrays in which the location of the nucleotide exit region of a polymerase are controlled, polymerase bound through fusion protein or particle is described, techniques for assisted loading of carbon nanotubes onto a chip are described, increased Debye screening length of channels of measurement devices are described, surface treatment of nanoFET gates are described, the use of a reference nanowire are described, alternative sequencing modes are described, NanoFETs within recessed regions are described, capacitive filters for improving signal to noise are described, the use of an Allosteric Signal for sequence reads is described, lowered background noise using tangential fields, nucleic acid binding agents and/or nucleases are described, and intentional lowering of Debye screening are described in U.S. Patent Application entitled "SINGLE-MOLECULE NANOFET SEQUENCING SYSTEMS AND METHODS" filed on Aug. 3, 2016, which is incorporated herein by reference for all purposes.

In some this characteristic electrical parameter is a voltage across the channel of the nano-electronic measurement device responsive to application of an AC voltage across the channel. In some this characteristic electrical parameter is an impedance of the channel of the nano-electronic measurement device responsive to application of an AC voltage across the channel. The frequency of the AC voltage applied to the nano-electronic measurement device can be varied over time in a manner that allows for the identification of the nucleotide analog in the active site, for example having gate electrical signal versus frequency characteristics. Base calling software is then employed to call bases by correlating the characteristic electrical parameter of the nano-electronic measurement device over time at the relevant biasing voltage with the expected characteristics of the labels. The called bases can be used to identify the sequence of the template nucleic acid whose sequence is complementary to that of the added bases. The methods of the invention utilize the characteristic that a nucleotide analog which is incorporated into a growing nucleic acid chain spends more time in the active site of the enzyme and therefore spends more time proximate to the channel of the nano-electronic measurement device than do non-cognate nucleotides that are not incorporated or freely diffusing nucleotides passing near the channel. Thus, the residence time of the labeled nucleotide in the active site of the enzyme can be used as a characteristic to distinguish incorporated nucleotides from freely diffusing nucleotides in solution.

Chips having arrays of nanoscale electronic elements having nano-electronic measurement devices are described. Each nano-electronic measurement device performs a sequencing reaction in real time, allowing for hundreds, thousands, millions, tens of millions or more sequencing reactions to be monitored simultaneously. The nanoscale elements used in devices, such as the source, gate, channel and drain, are typically constructed to have a small size, and therefore to have low levels of capacitance noise. This allows for rapid transfer of current for electronic measurements of events which typically occur on the microsecond to millisecond timescale. The chips can be prepared using known semiconductor processing techniques, for example on a silicon substrate. The nano-electronic measurement devices in the array have a polymerase enzyme-template complex attached to the channels of the nano-electronic measurement devices, proximate to the gates.

Systems for carrying out sequencing are described. The nano-electronic measurement device sequencing chips of the invention mate with a socket that holds the chip in place and provides electrical connections to interconnects on the chips for transferring electrical signals to and from the nano-electronic measurement devices. A current/voltage source provides the current and voltage to bring the nano-electronic measurement devices to the potential and in some cases the desired AC frequencies. A nano-electronic measurement device is used to determine the electrical signal changes associated with the presence of the charge labels.

The system includes a fluid reservoir for holding the sequencing reagents in contact with the nano-electronic measurement device on the chip. The fluid reservoir can be, for example, a microfluidic chamber or a well. The system can also have either a counter electrode, a reference electrode or both in contact with the fluid. The counter electrode and or the reference electrode can be incorporated into the chip or can be separate from the chip, and in contact with the liquid sample. In the fluid reservoir is a sequencing reaction mixture that allows a single polymerase enzyme proximate to the nano-electronic measurement devices to perform nucleic acid synthesis. The sequencing reaction mixture has nucleotide analogs with charge labels that are cleaved when the nucleotide is incorporated into the growing nucleic acid strand. The enzyme is proximate to the channels such that when a nucleotide analog is associated with the polymerase enzyme on its way to incorporation into the growing chain, the charge label on the nucleotide analog changes the electrical characteristics such as conductivity of the channel, voltage across the channel, or impedance of the channel. A voltage/current source can be used to vary an AC signal at the nano-electronic measurement device over time. A current meter, voltage meter, or impedance meter can be used to measure the level of current flow of the channel, the voltage across the channel, and/or other characteristics such as impedance. The measurement of a change in electrical characteristics at the nano-electronic measurement device indicates the presence of a charge label on the nucleotide analog held within the enzyme. A computer detects and records changes in signal at the nano-electronic measurement device, and uses this information to determine the sequence of nucleotide incorporation. In some embodiments, a current at the nano-electronic measurement device is measured using a current-to-voltage amplifier, known as a transimpedance amplifier. The conductivity signal indicates that the nucleotide corresponding to that label is being incorporated into the growing strand. By measuring a time sequence of incorporation, the sequence of the growing strand, and thereby the sequence of the corresponding template nucleic acid, is ascertained.

One aspect of the invention provides for real-time sequencing in which the incorporation of nucleotides into the growing strand is detected using a nano-electronic measurement device that is a field effect transistor, e.g., FET devices, nanoscale field effect transistors (nanoFETs), nanowire FET devices, carbon nanotubes/nanowires, single-walled carbon nanotube (SWNT) FETs, and other conductive nanowires, e.g., conductive silicon nanowires. As such, although certain specific embodiments herein describe features of the invention with reference to nanowires or nanotubes, it will be understood that the invention is not limited to the use of nanowires or nanotubes and can employ other FET devices, such as those listed above. It will be understood in this context that the terms "nanowire" and "nanotube" is meant to encompass all of the concepts involving FET devices and in particular carbon nanotubes, as well as any other FET device with a spatially restricted channel. The incorporation can be detected, for example, by changes in the conductivity of the channel of the nanoFET. Thus, where the application refers to the channel of a FET devices it is to be understood that the channel can be a nanowire or carbon nanotube. In some cases, the FET channel (also termed a "sensor") comprises a nanowire, and incorporation is detected by detecting changes in current across the nanowire. Although various embodiments described herein comprise polymerase enzymes performing nucleobase incorporation, the invention is not limited to only those embodiments and can also or alternatively comprise other types of nucleic acid processing enzymes, e.g., helicases, ligases, topoisomerases, nucleases, and the like, where interaction of the nucleic acid processing enzyme with a nucleic acid results in a detectable change in conductance, whether or not nucleobase incorporation is occurring. These changes are detected as signals that measure some aspect of the interaction between the enzyme and the nucleic acid, e.g., informing about the components or progress of a biochemical reaction between them.

In certain embodiments, a polymerase enzyme complex including a polymerase enzyme and a template nucleic acid is immobilized onto the nanowire or proximal to the nanowire. The polymerase enzyme complex is exposed to a reaction mixture that supports nucleic acid synthesis. The reaction mixture includes nucleotides or nucleotide analogs in which at least one of the types of nucleotide analog has a label that will be referred to herein as a conductance label (which can also be referred to as a charge label or as a conductance-modulating label). In some cases the conductance or charge label is a charge label. In certain embodiments, the label is connected to the polyphosphate portion of the nucleotide analog such that when the nucleotide analog is incorporated, the label is released as the polyphosphate chain is cleaved. In other embodiments, the label is a characteristic of the nucleotide analog that is absent from a canonical nucleotide, e.g., a base modification or extended polyphosphate tail that does not prevent incorporation into a nascent strand by a polymerase enzyme. In other embodiments, the label is a chemical moiety that has been attached to the nucleobase or the sugar ring. In alternative embodiments, the conductance label is a natural part of a nucleotide, e.g., the naturally occurring triphosphate of a nucleotide could produce the electric field detected by the a nano-electronic measurement device. In some embodiments, all the nucleotides in a reaction mixture are natural and the identity of the bases is derived from differences in the electrical signal that result from base-dependent position changes of the nucleobase, the sugar ring, and/or the phosphate groups. In other embodiments, a subset of the nucleotides would be natural and the rest would be analogs containing different number of phosphates or terminal phosphate labels as described above.

Where the charge label is linked to a phosphate group other than the alpha phosphate or when the charge label comprises the beta phosphate the incorporation of the nucleotide analog results in the release of the conductance label, restoring the conductivity of the nanowire to a value that is not impacted by the presence of the label, e.g., a baseline value. It is contemplated in the present invention that the baseline value may be impacted by the primary structure of the nucleic acid template and/or different conformational states of the enzyme, and baseline correction for sequence content is an aspect of the invention. While each of the four types of nucleotides may sample the active site, the nucleotide or nucleotide analog that is incorporated (a cognate nucleotide) will spend a longer time in the active site than a nucleotide or nucleotide analog that is not incorporated. Thus, the conductivity of the nanowire detects when a labeled nucleotide analog is present in the active site of the polymerase enzyme.

The invention provides for real time sequencing in which the incorporation of nucleotides into the growing strand is detected using a nano-electronic measurement device such as a nanoscale field effect transistor (nanoFET). The incorporation can be detected, for example, by changes in the conductivity of the gate of the nanoFET that is measured as changes in voltage using, for example, a transimpedance amplifier. The characteristics of the conductance change in the nanowire can be different for different conductance labels. Thus, in addition to detecting the presence of an incorporated nucleotide, the methods of the invention allow for discriminating between two or more nucleotide analogs in the reaction mixture. Typically four types of nucleotide analogs are used, corresponding to A, G, T, and C for DNA and to A, G, U, and C for RNA, each having a different conductance label. By observing the incorporation of nucleotides over time, the sequence of the template nucleic acid in the polymerase enzyme complex can be determined. The polymerase specifically adds a nucleotide to the growing strand that is complementary to the nucleotide in the template strand, e.g. A<->T, and G<->C. By determining which nucleotides have been added to the growing strand, the sequence of the template strand can be determined.

A nanowire can be used as the channel in the nano-electronic measurement device, with electrodes attached to either side of the nanowire acting as the source and the drain. The nanowire can be, for example, a carbon nanotube or a semiconductor such as doped silicon. There are many materials that can make up the nanowire or channel, examples of which are described in more detail below.

In some cases the channel of the nano-electronic measurement device is used to perform nucleic acid sequencing by measuring the presence of the labeled nucleotide analog within the enzyme complex as the enzyme adds nucleotides to a growing strand in real time. FIG. 1 provides a schematic representation of a method for real time nucleic acid sequencing with two nanoscale electrodes acting as source and drain with a nanowire channel connecting them. A polymerase-template complex bound proximate to the nanowire or channel. In FIG. 1 the polymerase enzyme is attached directly to the nanowire. In some cases, rather than being directly attached, the polymerase enzyme is attached to the substrate proximate to the nanowire at a distance such that the presence of a charge label attached to a nucleotide analog that is associated with the enzyme is detected by a change in conductance of the nanowire. A substrate 100 has a region on its surface with two electrodes 102 and 106 separated on the order of nanometers. For example, the separation can be from 1 nm to 400 nm, or from 2 nm to 100 nm. A nanowire 104 extends across the gap, connecting electrodes 102 and 106 (the source and drain of the FET). In some cases, the source and drain are covered with an insulating material such that the source and drain are not in direct contact with the solution. Onto the nanowire or channel 104 is attached a polymerase enzyme complex comprising a polymerase enzyme 110 and a nucleic acid template 130. While a linear template is shown in FIG. 1, other template conformations can be used, e.g., hairpin or circular templates such as those described in U.S. Pat. No. 8,153,375, incorporated herein by reference in its entirety. The complex is attached to the nanowire or channel 104 by an attachment moiety 120. As shown in FIG. 1, the polymerase enzyme is attached to the nanowire. In some cases, the template nucleic acid can be attached to the nanowire, either directly, or, for example, through hybridization with a primer attached to the nanowire. In some cases, the nano-electronic measurement device is disposed horizontally on a substrate surface. In some cases, the electrodes and nanowire are disposed vertically, e.g. as a stack of layers.

The substrate comprising the nano-electronic measurement devices is contacted with a fluid comprising a sequencing reaction mixture. The sequencing reaction mixture has the reagents required for carrying out polymerase mediated nucleic acid synthesis. The sequencing reaction mixture will generally include divalent catalytic cations such as Mn++ or Mg++ salts for activating the enzyme, as well as other salts such as Na+ or K+ for providing the appropriate ionic strength. Desirable ionic strengths range from 0.01 mM for minimal functioning upwards. Typically, ionic strengths from 50 mM to 500 mM, more preferably from 100 to 400 mM, and even more preferably between 200 and 300 mM can provide for desired levels functioning of the enzyme. In some cases, even concentrations as high as 3 M might be desired to study the behavior of these enzymes at high salt concentration. These salts can also be used to adjust the background capacitance at the electrodes. The ions in the solution are attracted to any charge that might be brought close to the nanowire FET, and these charges, having the opposite charge as the approaching charge, will have the effect of screening or blocking the penetration of the electric field into the solution. The blocking effect by these so-called counter ions can have a characteristic length scale which is very short—just 1 nm at ~150 mM of salt. Because the typical sequencing enzyme might have a dimension of between 5 and 15 nm in diameter, there can be portions of the enzyme that are outside the detection zone of the nanowire detector, thus reducing the power and sensitivity of these methods. As such, various strategies described herein improve the sensitivity of sequencing detection at ionic strengths that might screen the charges that are associated with the presence of a nucleotide, as further described below.

The sequencing reaction mixture also contains charge labeled nucleotide analogs such as labeled nucleotide analog 140. In FIG. 1, nucleotide analog 140 is a cognate nucleotide having a base that is complementary to the next position in the template nucleic acid 130. The nucleotide analog 140 has a nucleotide portion 144 comprising a nucleobase, a sugar, and a polyphosphate portion. The nucleotide analog 140 has a charge label 142 that is attached to the polyphosphate portion of the nucleotide portion 144 through linker 146.

In FIG. 1(B) the nucleotide analog 140 is held in the active site of the polymerase enzyme 110. Because it is a cognate nucleotide, nucleotide analog 140 is recognized by the enzyme as such, and will be held in the enzyme longer than will a non-cognate nucleotide. At the time that the nucleotide analog 140 is associated, its presence will be detected by a change in conductivity of the nanowire or channel 104, resulting in a change in current in the channel that is measured, in some embodiments, as a change in voltage by putting the drain in electrical communication with an amplifier, such as a transimpedance amplifier. Electrodes 102 and 106 are addressed with either direct or alternating current voltage. In some cases, the electrodes are cycled through a series of frequencies, either continuously or in steps. The charge label 142 causes the characteristics of conductivity, impedance, or voltage as measured across the electrodes or through the drain to change, allowing both its presence and its identity to be determined.

When the nucleotide portion of analog 140 is incorporated into the growing strand as shown in FIG. 1(C), the polymerase enzyme cleaves the polyphosphate portion of the nucleotide analog. This cleavage occurs between the alpha and beta phosphates in the polyphosphate portion which releases the portion of the nucleotide analog comprising the charge label 142, which diffuses away from the substrate. This cleavage and diffusion away of the label ends the period in which the electrical characteristic of the nanowire or channel, such as conductance, is affected by the presence of the charge label. The change in the electrical characteristic, then, provides a measure of the residence time of the nucleotide analog in the active site prior to incorporation, which can be used to determine that incorporation of a nucleotide has occurred.

The paragraphs above and FIG. 1 describe the detection of a nucleotide analog. The approach described can also be applied to the measurement of the incorporation of more than one type of analog, for example 2, 3, 4, 5 or more types of analogs. For example, typically four different types nucleotide analogs corresponding to either A, G, C, T, for DNA or A, G, C, U for RNA are used for sequencing. Each of the four types of nucleotide analogs has different and distinguishable electrical characteristics (e.g. conductance characteristics, voltage characteristics) for instance, from four different charge labels. The different types of nucleotide analogs can have different magnitudes of electrical characteristic change, different electrical characteristic versus time attributes, or can have other distinguishable electrical characteristics such as different current oscillation color or can have any combination of the above characteristics.

Figure 2:
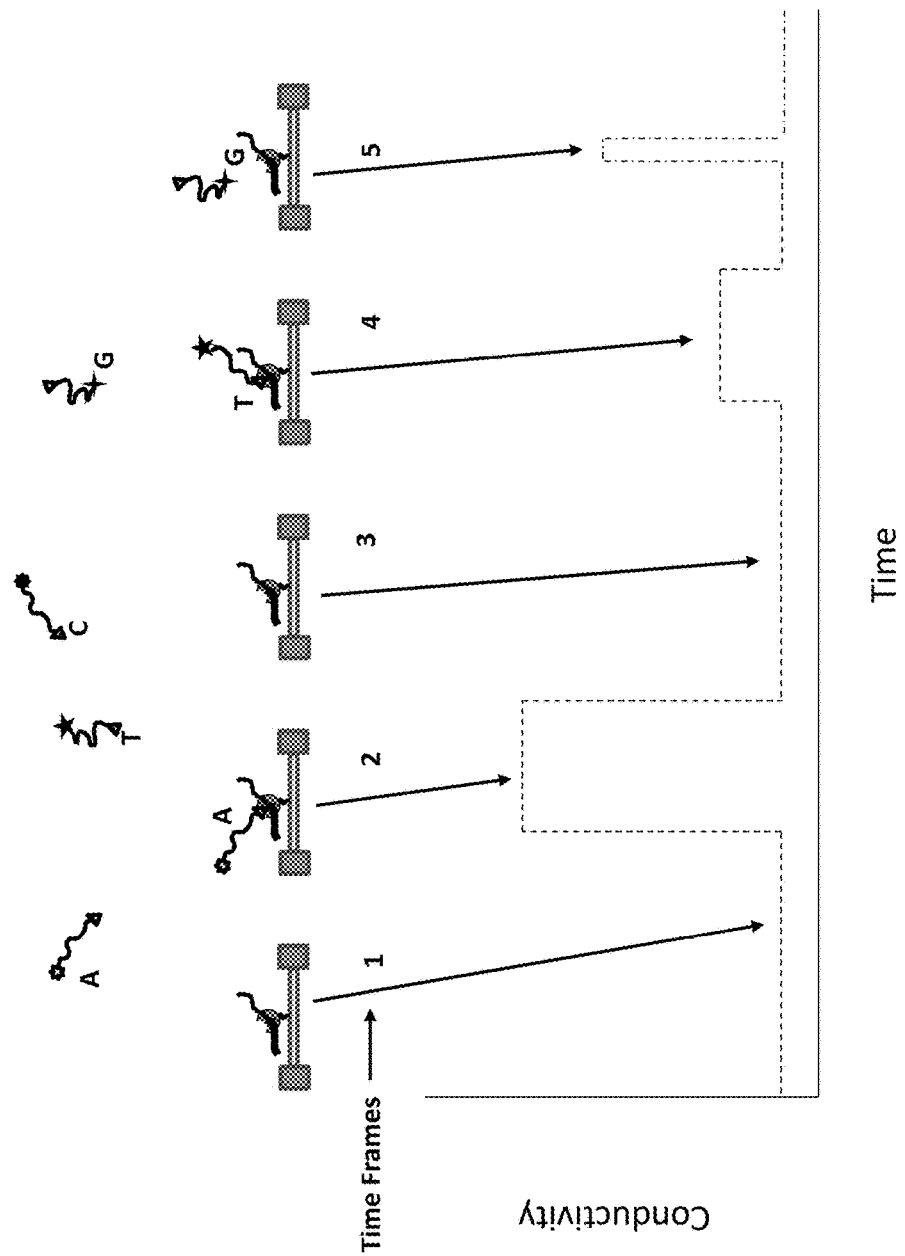
FIG. 2 shows how electrical signal at the gate of the nano-electronic measurement device can be used to sequence a template nucleic acid.

FIG. 2 shows how the nanowire or channels of the invention can be used to call a series of bases for sequencing. A graph is shown indicating the conductivity signal through the nanowire or gate that is detected. There are four types of nucleotide analogs, each having a different charge label, for example, each with a different magnitude of current change in the nanowire or channel when in the vicinity of the nanowire or channel. For example, the voltage across the two electrodes, the source and the drain can be kept constant throughout the experiment, and the current that passes through the nanowire or gate is monitored over time and this current can be measured as a voltage, for instance, using a transimpedance amplifier.

The method is described in FIG. 2 by referring to five different time frames. During time frame 1, none of the four nucleotide analogs is associated with the polymerase enzyme. In time frame 2, a nucleotide analog corresponding to nucleobase A is in the active site for a time that is characteristic of incorporation (e.g. about 10 msec to about 500 msec). During the time it is in the active site, the measured conductivity (e.g., measured as a voltage using a transimpedance amplifier) rises to a level characteristic of the label on that nucleotide analog. This level of conductivity for a residence time corresponding to incorporation indicates the incorporation of A. When the nucleotide is incorporated, the charge label is cleaved and the conductivity signal returns to baseline. In time frame 3, as in time frame 1, no nucleotide analog is in the active site of the polymerase and the conductivity is at a baseline level. During time frame 4, a nucleotide analog corresponding to T is incorporated into the growing strand. The nucleotide analog corresponding to T is held within the active site for a period of time characteristic of incorporation. During the time it is held within the enzyme, a conductivity characteristic of the label on the T nucleotide analog is seen. When the analog is incorporated, the label is cleaved, and diffuses away and the conductivity again returns to baseline. In time frame 5 for a short time, an increase in conductivity (to a level consistent with the label corresponding G) is detected. The time of the increased conductivity is too short to be associated with an incorporation event. This type of feature can be seen, for example, where a non-cognate nucleotide such as G is sampling the active site, after which it diffuses from the enzyme, where the non-cognate nucleotide diffuses near enough to the nanowire to change its conductance, or where the G nucleotide binds non-specifically for a short period of time. During the time of the portion of the experiment shown in FIG. 2, the data indicate that an A and a T were incorporated, which thus indicates that there is a T followed by an A in the template nucleic acid. While this description relates to the incorporation of two nucleotides, this method can be used to sequence long stretches of nucleic acids from hundreds to tens of thousands of bases or more.

The example of FIG. 2 is carried out with four nucleotides, each having a charge label that exhibits a different magnitude in an electrical characteristic of the nanowire or channel, such as voltage, current or impedance. It will be understood that the same approach described in FIG. 2 can be applied to cases in which electrical characteristic versus time (dielectric spectrum) or current oscillation color (also referred to as noise color, which can be influenced by the type of length and stiffness of the linker attached to the label, the type of conductance label, and the diffusion rate of the label) or any combination of the three is used to identify the incorporated bases.

Thus, the invention, in some aspects provides a method for nucleic acid sequencing that includes providing a substrate comprising an array of nano-electronic measurement devices (e.g., nanoFETs). Each nano-electronic measurement device has a source, a drain, a gate and a channel. The source and drain are typically nanoelectrodes, and the channel is typically a nanowire or other nanostructure connecting the source and drain. The gate is used to bias the channel of the nano-electronic measurement device to an operating conductivity which is then altered by electrical interaction with charge labels. The channel can be a doped semiconductor such as doped silicon. The channel can be a carbon nanotube, either single walled or multi-walled. The carbon nanotube gate can be modified or doped. A subset of the nanoFETs will have a single polymerase enzyme complex attached to channel of the nanoFET or attached to the substrate proximate to the channel of the nanoFET. Methods are known in the art for creating an attachment site on a nanowire detector such as the ones used by Sorgenfrei, et al. (2011) Nature Nanotechnology 6: 126-132 or by Olsen et al. (2013) J Am Chem Soc. 135(21): 7855-7860, both of which are incorporated herein by reference in their entireties.

Processes for forming nano-electronic measurement device arrays on CMOS sensors are known in the art. Such sensors can be formed, for example by transferring nanotubes onto a CMOS integrated circuit (see Meric et al. "Hybrid carbon nanotube-silicon complementary metal oxide semiconductor circuits" Journal of Vacuum Science & Technology B. 2007; 25(6):2577-80. doi: 10.1116/1.2800322 which is incorporated herein by reference in its entirety. Techniques such as this help to circumvent the mismatch between nanotube growth temperatures and the maximum temperature tolerated by a CMOS device. In some cases, devices of the invention can made by employing a transfer of arrays of grown parallel tubes to arbitrary substrates (See, for example Kang et al. "High-performance electronics using dense, perfectly aligned arrays of single-walled carbon nanotubes" Nat Nano. 2007; 2(4):230-6) which is incorporated herein by reference in its entirety.

One way of having a single complex attached to the channel or to a region of the substrate proximate to the channel is to attach to the channel or to the region a binding reagent that binds with the polymerase enzyme complex, and to expose the substrate to a solution of polymerase enzyme complex at a concentration whereby a fraction of the nanoFETs have a polymerase enzyme complex becomes bound to channels or to nearby regions at a single molecule level. By selecting the right dilution level, Poisson statistics allows for up to 36% of the gates with a single complex attached, the rest having either no complex or multiple complex. Other methods including using steric interactions and providing highly specific bonding regions on the channel can provide greater levels of single complex than predicted by Poisson statistics.

The substrate is then exposed to a reaction mixture comprising a plurality of types of nucleotide analogs, each comprising a different charge label attached to the phosphate portion of the nucleotide analog. The attachment of the label to a phosphate portion allows for cleavage of the label by the polymerase as it breaks the polyphosphate strand when incorporating the nucleotide portion of the nucleotide analog into the growing strand. The charge label can be connected to the polyphosphate strand through a linker.

A voltage is applied between the source and drain of the nano-electronic measurement device using the gate, such that, when a nucleotide analog resides in the active site of the enzyme, the charge label on the nucleotide analog produces a measurable change in the conductivity of the channel. That is, the nanowire, carbon nanotube graphene nanoribbon, or other component is considered the channel of the nano-electronic measurement device. The gate is separated from the channel and is used to electrostatically control the nano-electronic measurement device operating point in a similar fashion to how a metal or poly gate in a MOSFET is used to electrostatically control the silicon channel underneath the gate. The voltage applied to the channel can be DC, pseudo DC (where the measurement is essentially performed with a DC measurement, but the polarity is alternated to prevent corrosion), or AC. In some cases the frequency across the source and drain can be varied over time to assist in distinguishing the identities of different charge labels. The charge label is typically a charged species whose interaction with the channel results in a change in the conductivity of the channel. In some cases, the charge label comes into direct contact, e.g. repeated direct contact, with the channel, and in other cases the charge label may affect the conductivity of the channel by its proximity to the channel. Both the channel and the charge label can be made in a manner to improve the change in conductivity of the channel by the charge label. For example, as described in detail below the channel can be doped at different levels, either p doped or n doped, in order to tune its response. Charge labels can be charged species that are water soluble. The charge labels can have multiple charges, e.g. from about 2 to about 2,000 charges. The charge labels can comprise dendrimers or nanoparticles. Multiple charge labels can be employed, each having a different level of charge, in some cases, with some charge labels positively charged and some labels negatively charged.

During the polymerase enzyme reaction, and while the voltage is applied, an electrical signal of the nano-electronic measurement device over time (e.g., current of the channel, voltage across the channel, impedance of the channel), is monitored. The electrical signal can indicate that an incorporation event for a specific type of nucleotide analog has occurred. One indication of an incorporation event is the duration of the signal, since, depending on the kinetics of the polymerase enzyme used, an incorporation event will occur in a range of times that is different than a diffusion event, a non-cognate sampling event, or sticking of labels to the substrate. Various characteristics of the electrical signal can be used to determine that a particular nucleotide analog is in the active site and being incorporated. One characteristic is the amplitude of the conductivity. For example, four charged labels, each with different levels of the same type of charge can give four different levels of conductivity. The conductivity level can be designed to increase or to decrease in the presence of a given charge label at a given operating point of the nano-electronic measurement device, e.g. using positively charged and negatively charged labels. In addition to the numbers of charges, the density of the charges on the label can also affect the signal and the density of charge of the charge label can be controlled in order to control the electrical signal at the nanoFET. The electric signal characteristics can also be controlled by controlling the structure of the nucleotide analog to change its current oscillation color characteristics.

The electrical signal can thereby provide the information required for determining the sequence of the template nucleic acid in the polymerase enzyme complex. Algorithms such as those described in U.S. Pat. Nos. 8,370,079 and 8,703,422, which are incorporated by reference herein in their entirety for all purposes.

Typically, the methods of the invention are carried out with four types of nucleotide analogs corresponding the natural nucleotides A, G, C, T, or A, G, C, U, each of the four types of nucleotide analogs having a different charge label. The nucleobase on the nucleotide analog will typically be the natural nucleobase, but modified nucleobases can be utilized as long at the polymerase enzyme that is used can effectively incorporate them into the growing strand.

In some aspects the invention provides a chip for sequencing a plurality of single nucleic acid template molecules. The chip has a substrate having a plurality of nanoFET devices, typically on its top surface. Each of the nanoFET devices has a source, a drain, a gate, and a channel. Onto the channel of some of the nanoFETs on the substrate is a single polymerase enzyme complex bound to the channel or bound to the substrate proximate to the channel of the nanoFET. The polymerase enzyme complex includes a polymerase enzyme and a template nucleic acid. The template nucleic acid is typically primed, and ready to act as a template for nucleic acid synthesis. The substrate is configured such that the nano-electronic measurement device come into contact with a sequencing reaction mixture. The substrate will typically have a well into which the reaction mixture is dispensed, or will have fluidic conduits or fluidic chambers providing the reaction mixture into contact with the nano-electronic measurement devices on the surface. The reaction mixture has the reagents required for carrying out nucleic acid synthesis including a plurality of types of nucleotide analogs. Two or more of the nucleotide analogs have different charge labels. The charge labels interact with the channel to modify its conductivity as described herein. The chip also has electrical connection sites for bringing current and voltage to the nano-electronic measurement devices, and for receiving electrical signals from the nano-electronic measurement devices.

In some embodiments, the nano-electronic measurement device on the chip can be any type of nanoFET, including the types of nanoFETs described herein, for example comprising a nanowire and/or comprising doped silicon.

The chip will typically have multiple nano-electronic measurement device, for example, greater than 1,000 nano-electronic measurement devices, or greater than 10,000 nano-electronic measurement devices. The chip can have, for example, about 1,000 nano-electronic measurement devices to about 10 million nano-electronic measurement devices or about 10,000 nano-electronic measurement devices to about 1 million nanoFET nano-electronic measurement devices.

The chip is typically made using semiconductor processing techniques, allowing for the inclusion of other functionality on the chip including electronic elements for one or more of: providing electrical signals to the nano-electronic measurement devices, measuring the electrical signals at the nano-electronic measurement device, analog to digital conversion, signal processing, and data storage. The electrical elements can be, for example, CMOS elements.

FIG. 3 provides another illustration of how single molecule nano-electronic measurement device sequencing is accomplished. FIG. 3(A) shows a polymerase enzyme complex comprising a polymerase enzyme 301 and a primed template nucleic acid 302 bound through the polymerase enzyme (illustrated here as a covalent attachment) to the channel 312 (e.g. carbon nanotube) of a nanoFET. Although not shown in FIG. 3(A) the nano-electronic measurement device is biased by a gate. The gate can take the form of a metal layer buried underneath the device (e.g., underneath channel 312), or a reference electrode+solution electrolyte which can both be used to set the operating point of the device. The nano-electronic measurement device has the channel 312 spanning the source and drain 310 and 311. In the time period represented by step 1, differentially labeled nucleotide analogs 304 are diffusing in solution near the nanoFET. FIG. 3(B) shows the signal at the nano-electronic measurement device. In step 1, the nano-electronic measurement device signal is at baseline. In step 2, a nucleotide analog corresponding to the base A is in the process of being incorporated into the nascent strand complementary to the template. During this time, the charge label comes into contact (or close enough proximity) to increase the conductivity of the channel (represented by the arrow). FIG. 3(B) shows that in step 2 there is an increase in intensity (e.g. an increase in current between the source and the drain). When the nucleotide analog corresponding to A is incorporated, the label is released, and the signal intensity returns to the baseline (step 3). In step 4, a nucleotide analog corresponding to T is being incorporated. This nucleotide analog has a different charge label, the nucleotide analog corresponding to A, which produces a smaller increase in intensity. This is illustrated by the peak in FIG. 3(B) step 4. The distance 370 represents a measure of the noise at the top of the peak. In the illustrated example, the signal to noise is on the order of 20 to 1. The distance 390 is the width of the peak corresponding to the incorporation of the nucleotide analog T, and represents the residence time of the nucleotide analog from when it binds to the polymerase to when the label is cleaved and is released into solution. In step 5, the charge label is cleaved and released, and the signal returns to baseline as seen in FIG. 3(B). The arrow 380 represents the area of a sequencing reaction and is provided to illustrate that the area of the sequencing reaction can be relatively small compared to the area required in a corresponding optical detection method. For example, the area per sequencing reaction can be on the order of 1.5 microns squared.

Controlling the Location of the Nucleotide Exit Region of the Polymerase

Figure 4A:
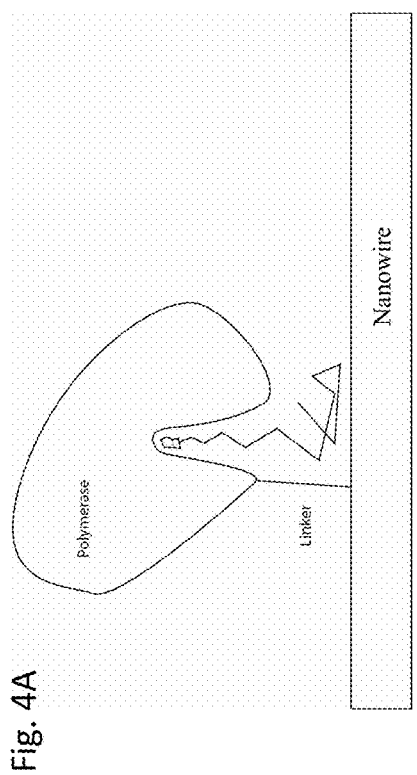
FIG. 4A show a single point of attachment near the nucleotide exit region to a nanowire.

As noted above, the instant system has an issue that is not typically encountered in sequencing methods, and this is the issue that at ionic strengths that are typically used for carrying out nucleic acid synthesis, charges in solution tend to be screened if they are farther than, for example, a few nanometers from the nanowire. One approach that we have developed for improved signal in the sequencing methods of the invention is to control the orientation of the polymerase with respect to the nanowire or nanotube. In particular, the polymerase is attached to the channel of the nano-electronic measurement device such that the nucleotide exit region of the polymerase is oriented toward the nano-electronic measurement device. The nucleotide exit region is the region of the polymerase where the phosphate portion of the nucleotide or nucleotide analog extends out of the polymerase. This is, of course, near the active site of the polymerase, but is a region specifically from which the nucleotide or nucleotide analog extends from or exits the polymerase. For example, a polymerase is immobilized on the nanowire in an orientation that ensures the detectable label is close to the nanowire detector when the nucleotide is in the active site of the polymerase, e.g., as shown in the exemplary schematic shown in FIG. 4A in which there is a single attachment through a portion of the polymerase near the nucleotide exit region. Certain DNA polymerases and other nucleic acid processing enzymes bind nucleotide triphosphates such that the terminal phosphate has a clear path to the bulk solution outside the enzyme. The nucleotide analog is held within the enzyme in a nucleotide analog binding portion of the active site of the polymerase. A terminal phosphate label that is attached to a nucleotide residing in the active site of an enzyme will extend out from that binding site and will emerge from the enzyme at this location. An aspect of the invention is attaching the enzyme to the nanotube such that the enzyme is immobilized in an orientation that ensures or promotes the configuration in which the portion of the nucleotide analog extending way from the polymerase is in close proximity to the nanowire sensor. In certain embodiments, "close proximity" means a distance which is either less than the Debye screening length, less than the radius of gyration of the terminal phosphate label, or less than some combination of the Debye length and the radius of gyration of the label. It is an aspect of the invention that proximity that is greater than the Debye length but not much greater will still provide useful benefit.

In some cases the polymerase is bound through a residue on the polymerase enzyme that is on the same side of the enzyme as the nucleotide exit region of the enzyme. In some cases, the residue is closer to the nucleotide exit region than a distance equal to one quarter of the longest distance from the nucleotide exit region back to the nucleotide exit region across the surface of the polymerase. In some cases the residue is less than 20%, less than 15%, or less than 10% of such distance relevant to the nucleotide exit region. Having the polymerase bound such that the nucleotide exit region is oriented toward the substrate is not typically desirable. For example, U.S. Pat. No. 8,936,926 teaches that it is desirable to have the polymerase active site attached through a domain that is distal to the active site.

Methods are known in the art for linking a binding group to a desired position on the surface of a protein, e.g. a polymerase. Substitutions are made for amino acids at positions on the surface of the protein that do not unduly affect the activity of the enzyme, for example, with one or more attachment moieties for connection to the nanowire detector. For example, cysteine residues can be targeted specifically for attachment, e.g., in proteins that have a low cysteine density either overall or on the surface. The protein may be naturally low in cysteine, or may be engineered to have a reduced cysteine density. A cysteine residue can be added at a desired position and subsequently bound to an attachment moiety, e.g., at a residue near the exit tunnel of the polymerase. Alternatively, naturally occurring cysteine residues in the protein can be used at attachment point. Further, even where a cysteine residue is engineered into a protein to serve as an attachment site, if a small portion of the proteins instead bind via a native cysteine, this is unlikely to alter the signal enough to be problematic, so engineering to reduce native cysteines may not be required. In other embodiments specific residues in a protein can be replaced with non-natural amino acids by creating a $21^{st}$ amino acid codon. In this case the $21^{st}$ amino acid can be a residue that bears an attachment site. For example, in Phi29 DNA polymerase position 375 is near the nucleotide exit region where the phosphate portion of the nucleotide extends out of the polymerase. In one preferred example, an attachment residue is substituted at or near position 375 so as to provide that the attachment is near the nucleotide exit region and thus the nucleotide exit region will be in close proximity to the detection zone of the nanowire. In some cases, the attachment residue is within 5 amino acids of position 375. Position 512 is also close to this region, and in another preferred example, an attachment site is positioned at or near position 512. In some cases, the attachment residue is within 5 amino acids of position 512.

Figure 4C:
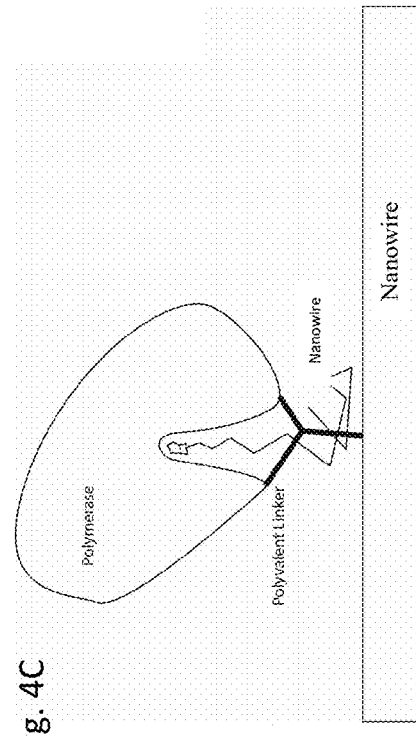
FIG. 4C shows an adaptor that multiply attaches to the polymerase and makes a single attachment to the nanowire.
Figure 4B:
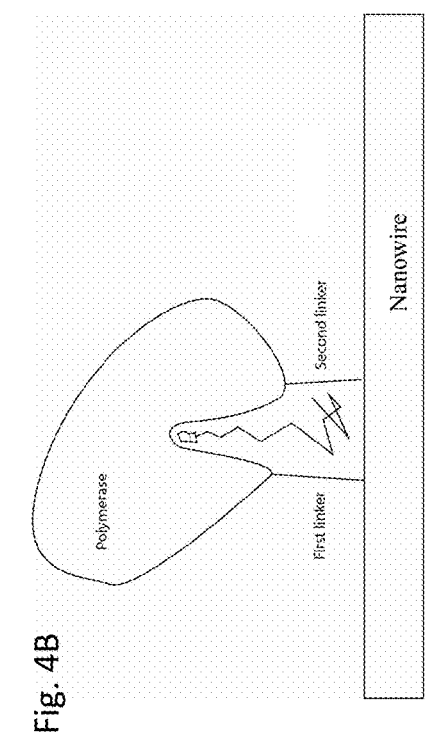
FIG. 4B shows multiple attachments from the polymerase to a nanowire.

The position of the nucleotide exit region with respect to the nanowire can also be controlled using multiple attachments to the polymerase enzyme. In addition to controlling distance, these approaches also constrain the rotation of the enzyme and ensure the portion of the nucleotide exit region where the nucleotide extends from the polymerase is positioned to ensure the conductance label is in close proximity to a nanowire detector. FIG. 4B shows an embodiment having two attachments linking a polymerase to a nanowire. In a preferred embodiment, attachment residues are positioned at or near both positions 375 and 512, for example one attachment residue is within 5 amino acids from position 375, and one attachment residue is within 5 amino acids from position 512. In some embodiments both of the attachment residues are closer to the nucleotide exit region or nucleotide exit region than a distance equal to one quarter the longest distance from the nucleotide exit region back to the nucleotide exit region (or nucleotide exit region to nucleotide exit region) across the surface of the polymerase. In some cases both residues are at a distance less than 20%, less than 15%, or less than 10% of such distance relevant to the nucleotide exit region or nucleotide exit region. Linking to a polymerase at multiple points, and in particular linking across the nucleotide exit region of a polymerase is described, for example in U.S. Pat. No. 7,745,116 which is incorporated by reference herein.

In other embodiments, more than two attachment sites are used, methods for creating attachment sites on a nanotube or nanowire are described further below.

In some cases, an "adaptor molecule" can be used that will bind to multiple binding sites on the enzyme, while providing a single binding site that will attach to the nanowire detector. FIG. 4C provides an illustrative example of a polymerase linked to an adaptor molecule at two positions, where the adaptor molecule ("polyvalent linker") is attached at only one position on a nanowire. Specific examples of such adaptor molecules can be found in U.S. Patent Publication No. 2015/0011433, which describes polyvalent biotin binding capability for ensuring oriented binding to an avidin or streptavidin molecule and is incorporated herein by reference in its entirety. In alternative embodiments, if multiple positions on the polymerase are to be linked to the nanowire, then multiple binding sites are engineered into the nanowire detector. These binding sites are arranged at desired distances to each other either using random chance or by using a templating molecule such as a DNA strand or polypeptide that can provide binding sites at defined positions relative to each other. These binding sites can be located, for example, on either side of the active site. See, for example in U.S. Pat. No. 7,745,116 which is incorporated by reference herein.

Thus, in one aspect the invention provides single molecule nano-electronic measurement device sequencing devices, methods, and systems in which the nucleotide exit region of the polymerase is oriented toward the channel of the nano-electronic measurement device used for sequencing. In some cases, this involves having the polymerase attached to the nano-electronic measurement device through a linker attached near the nucleotide exit region of the polymerase. In this context, near means, for example, on the same side of the polymerase. In some cases the polymerase is attached through a linker to a site that is less than 50 Angstroms, less than 40 Angstroms, less than 30 Angstroms, less than 20 Angstroms, or less than 10 Angstroms from the nucleotide exit region. In some cases the polymerase has two different attachment points to the nano-electronic measurement device channel in which at least one of the attachment points is near the nucleotide exit region of the polymerase. In some cases, one or both of the attachment points are less than 50 Angstroms, less than 40 Angstroms, less than 30 Angstroms, less than 20 Angstroms, or less than 10 Angstroms from the nucleotide exit region.

Figure 5:
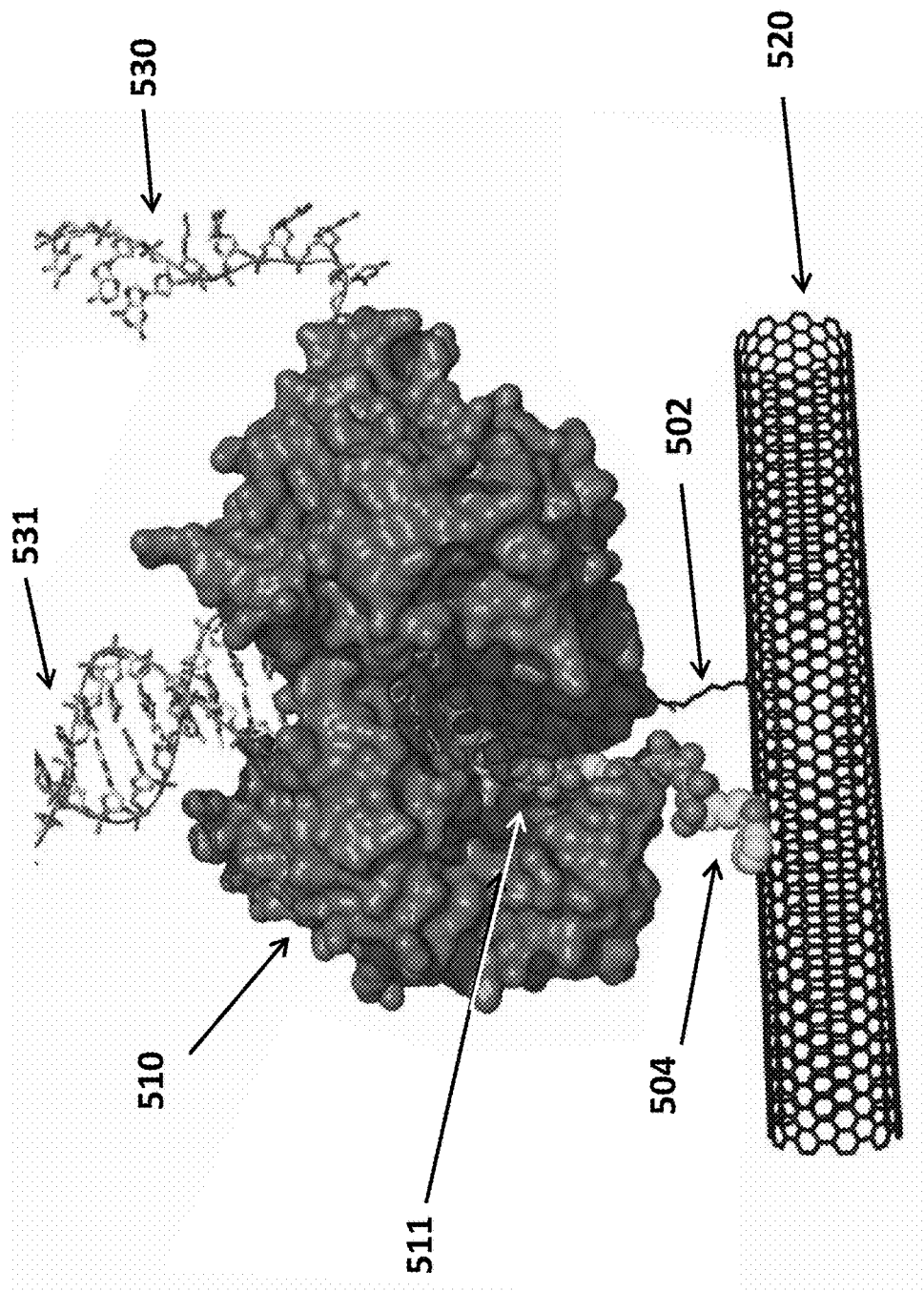
FIG. 5 illustrates carrying out single molecule nano-electronic measurement device sequencing with a polymerase having its nucleotide exit region oriented toward a carbon nanotube gate of a nano-electronic measurement device.

FIG. 5 shows an example of a polymerase enzyme bound to the channel of a nano-electronic measurement device where the polymerase is oriented such that the nucleotide exit region of the polymerase is oriented toward the channel. In this embodiment, there is a single attachment point to the polymerase through linker 502 to the carbon nanotube channel 520. In this embodiment the link to the nanotube is covalent, and the length of the linker 502 is relatively short. For example, in some cases the linker is between about 1 nm and about 10 nm in length, or about 1 nm to about 5 nm in length. While the polymerase has some freedom of motion, the link maintains the polymerase such that the nucleotide exit portion of the polymerase 511 is oriented toward the nanotube 520. This allows for the charge label 504 on the nucleotide analog in the active site of the enzyme to extend, and in some cases, as the embodiment shown, come into contact with the nanotube while the enzyme is in the process of incorporating the nucleotide. As can also be seen in this illustration, orienting the polymerase in this manner can also have the added benefit keeping the template nucleic acid away from the nanotube where it might produce background noise. It can be seen here that both the entering template 530 and the exiting template 531 are oriented generally away from the carbon nanotube.

Another aspect of the invention is the use of non-covalent transient binding moieties that partition to a nanotube in order to bias the orientation of the nucleotide exit region towards the detection zone of the device. For example, in certain embodiments comprising multiple attachment sites, one of the attachment sites is modified with a covalent attachment (or a non-covalent tight binding target such as streptavidin-biotin) and a second binding site is functionalized with a hydrophobic moiety that is designed to partition heavily into a bound state with the nanowire detector. A wide range of binding affinities can be used, so long as the aggregate kinetics of binding and unbinding are fast compared with the residence time of a typical terminal phosphate label on a nucleotide analog that is participating in a binding event. For example, a significant benefit can come from a binding moiety that has a 10% or 20% or 50% duty cycle of binding to the nanotube as long as the off-rate is faster than about 100 per second, or more preferably faster than 1000 per second. In another mode, moieties that provide a duty cycle of greater than 95% could be used even with slower off rates by simply tolerating the sequencing errors that result from incorporation events that take place while the enzyme is in the wrong orientation.

Figure 6:
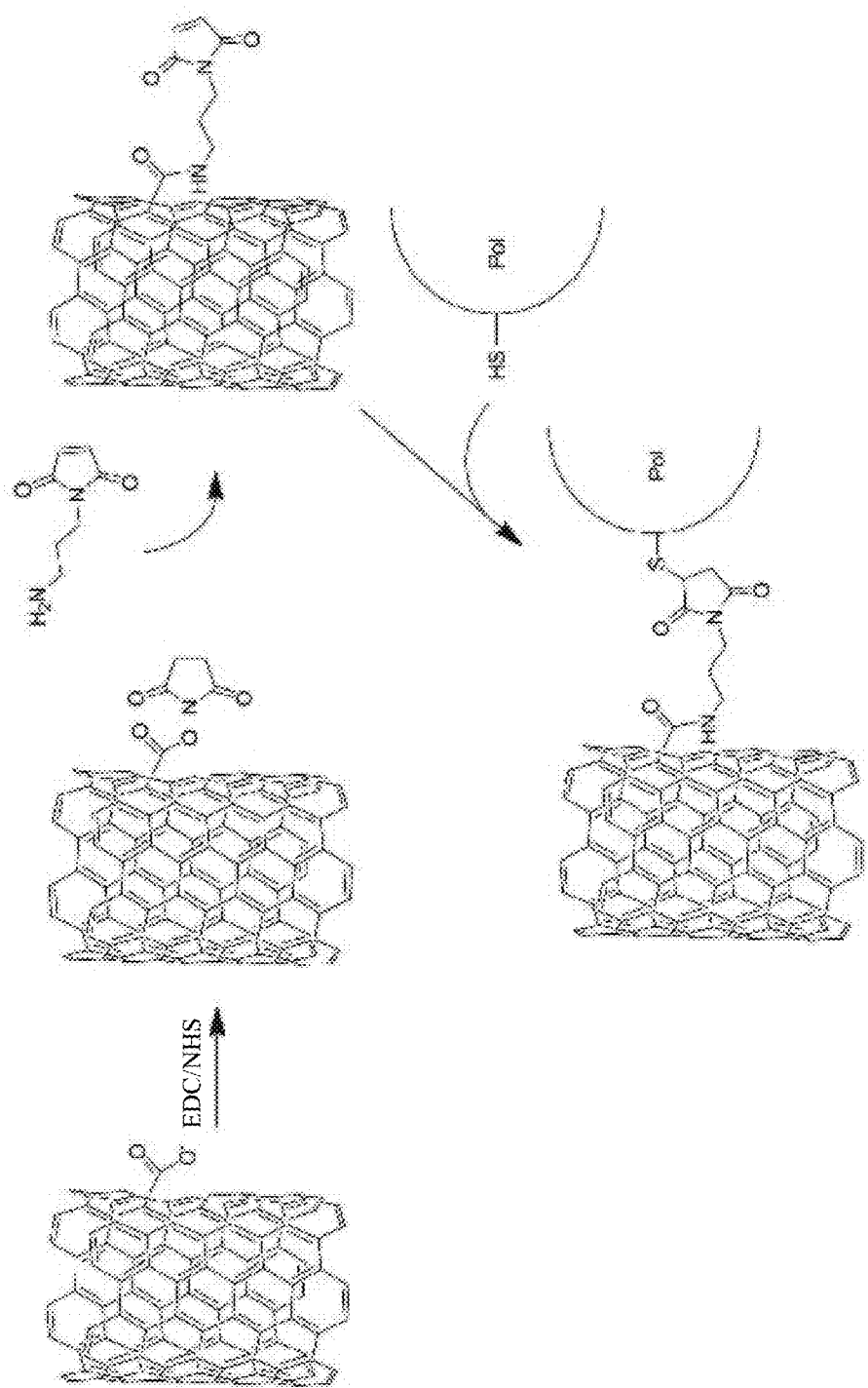
FIG. 6 shows representative chemistry for covalent attachment of a polymerase enzyme to a carbon nanotube.

In some embodiments, it is desirable for there to be a covalent connection between the polymerase enzyme and the channel. FIG. 6 shows one approach for such a covalent attachment. First a carboxylic acid is introduced onto the nanotube via oxidation. The carboxylic acid is derivitized to an N-hydroxy succinimidyl (NHS) ester. The ester is then extended using a small molecule having an amine end and a maleimide end. The maleimide group on the nanotube will react with a thiol group of a cysteine residue on the polymerase to provide a covalent attachment. By modifying the polymerase using well known methods, specific cysteine residues can be introduced (e.g. near the nucleotide exit region), and undesired cysteine residues can be removed. Such covalent attachment to nanotubes is described, for example in Sorgenfrei, et al. "Label-free single-molecule detection of DNA-hybridization kinetics with a carbon nanotube field-effect transistor" Nature Nanotechnology. 2011; 6(2):125-31. doi: 10.1038/nnano.2010.275; Goldsmith et al. "Monitoring Single-Molecule Reactivity on a Carbon Nanotube" Nano Letters. 2008; 8(1):189-94. doi: 10.1021/nl0724079; and Sorgenfrei et al. "Debye Screening in Single-Molecule Carbon Nanotube Field-Effect Sensors" Nano Letters. 2011; 11(9):3739-43. doi: 10.1021/nl201781q, the disclosures of which are incorporated herein by reference in their entirety for all purposes.

Polymerase Bound Through Fusion Protein or Particle

In some aspects of the invention, the sensitivity of the nano-electronic measurement device array is enhanced by attaching the biomolecule, e.g. polymerase enzyme, to the channel of the nano-electronic measurement device through a fusion protein that allows the electric field lines to penetrate it, allowing the channel to be more sensitive to the presence of a charge label such as a charge label in or near the active site.

As described above, the presence of ions including counterions in the solution have the effect of screening or blocking the penetration of the electric field into the solution. In certain aspects, the sensitivity of the nano-electronic measurement device with respect to a labeled nucleotide is enhanced by displacing solution-phase counterions using a molecular crowding species, e.g. a dielectric nanoparticle (e.g., polystyrene spheres, optionally 5 nm in diameter), a zwitterionic polymer, or other dielectric material that is placed between the charge of interest and the detection zone of the nanowire sensor. In some embodiments, this material comprises the enzyme peptide chain itself and/or an additional polypeptide that is either fused or separate from the enzyme or a dielectric particle such as polystyrene or silica.

Figure 7:
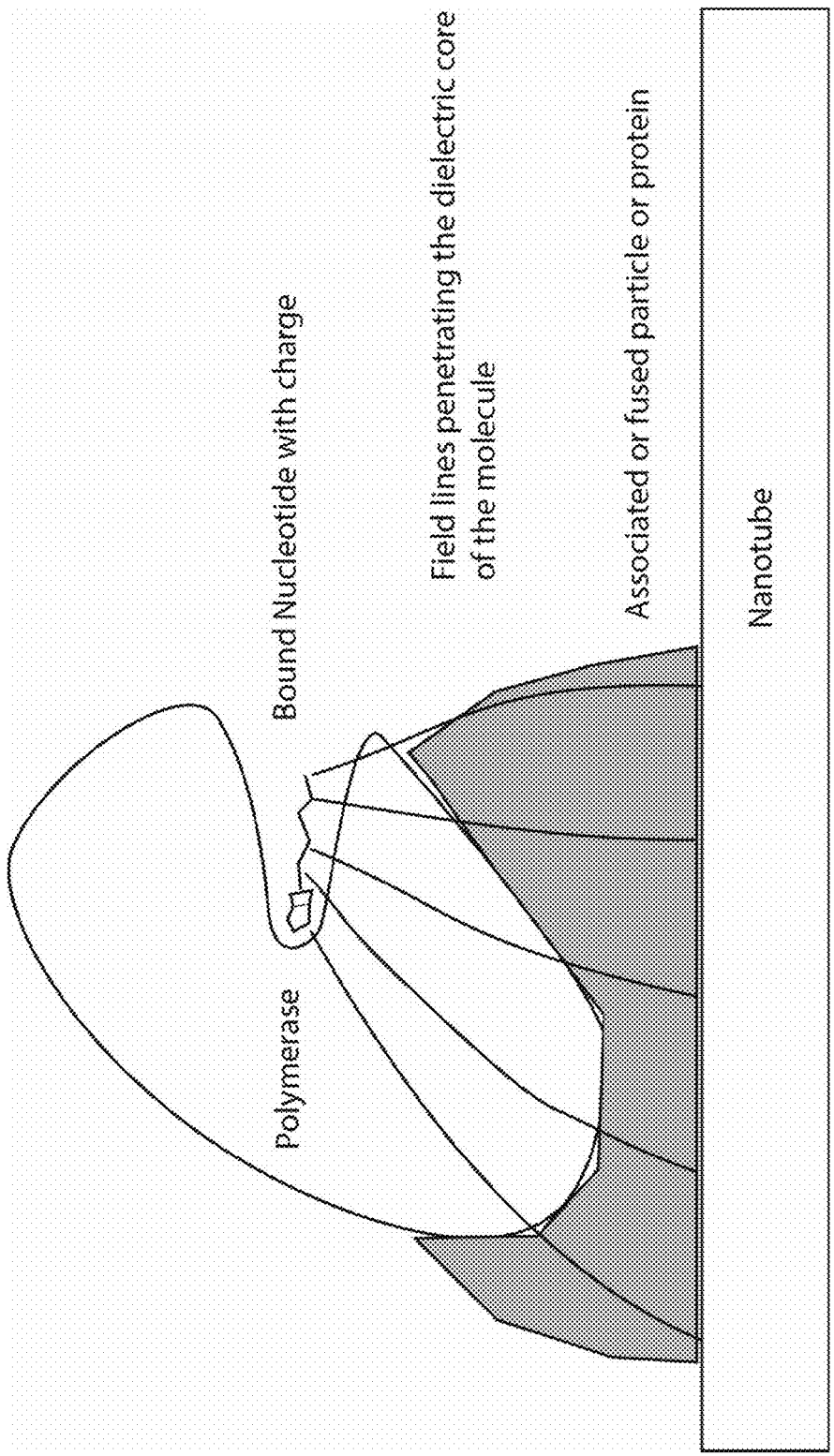
FIG. 7 illustrates how a fused particle or protein bound between the nano-electronic measurement device channel and the polymerase can result in improved detection of charged species at or near the active site of the polymerase.

The space that is occupied by a dielectric medium is not available to host screening counter-ion charges and thus the detection range of the nanowire can be extended specifically with formed dielectric spaces to include the active site. For example, in some embodiments, the nucleic acid processing enzyme is fused with a polypeptide whose folding characteristics are engineering to envelop the nanowire and displace counterions from residing between the nanowire and the protein. In this mode, electric field lines originating from the charge of interest will penetrate through the dielectric portions of one or both of the enzyme or the associated or fused envelope peptide such that they are able to reach the detection zone of the nano-electronic measurement device, for example, as shown in FIG. 7.

Examples of fusion proteins comprising a polypeptide, e.g. a Phi29 polymerase, and another, optionally non-functioning, protein with a hydrophobic core have been previously described, e.g., in U.S. Pat. No. 8,323,939 and U.S. Patent Publication No. 2010/0260465, both of which are incorporated herein by reference in their entireties. This fusion protein creates a zone of further penetration into the surrounding space and will thus increase sensitivity. In yet further embodiments, the nanoparticle or other dielectric material is linked to a nanowire near or on which the enzyme is positioned to block screening counterion charges and improve detection.

Enhanced Sensitivity with Zwitterionic Salts

In alternative embodiments, the concentration of monovalent and divalent (and polyvalent) ions is reduced and the systems ionic strength is supplemented with zwitterionic salts whose overall charge is zero or near zero. These salts can assist with the solubility of key components of the system without participating in the charge screening. In some cases, a zwitterionic salt could permit a reduction in monovalent salt concentration of 10%, 20%, 30%, 50%, 80%, or more. The resulting increase in the Debye screening length would directly result in increased sensitivity of the nano-electronic measurement device to charges that are not directly contacting the nano-electronic measurement device channel. In some embodiments, zwitterionic salts make up more than 30%, more than 40%, more than 50%, more than 60%, more than 70%, more than 80%, or more than 90% of the ions in the sequencing reaction mixture.

Conductive Polymers on the Nano-Electronic Measurement Device Channel to Extend Region of Sensitivity Other aspects of the invention that increase the sensitivity of a nano-electronic measurement device include decorating the surface of the nano-electronic measurement device with conductive polymers that extend the zone of sensitivity to the charge of interest. This allows for detecting a charge that is further away from the channel of the nano-electronic measurement device without having the conductive polymer present. Materials that are useful include polymers with high densities of double and single bonds in resonance. For example, polyacetylene or polythiophene. Polymer chains of redox moieties such as ferrocene can also serve as molecular conductors. When the nanowire is decorated with such current-carrying molecules, the polarization caused by the charge of interest will be communicated though the conductor to the nanowire channel of the nano-electronic measurement device.

In some embodiments of this method, the conductive polymers are not covalently attached, but rather allowed to associate non-covalently via hydrophobic interactions with the channel of the nano-electronic measurement device, e.g. nanowire or nanotube. In some cases the conductive polymer has side groups that promote the water solubility of the chain. In some cases the conductive polymer molecules have a dual character, containing regions that are non-soluble and regions that are soluble, for example, block copolymers. The non-soluble portions will tend to associate with a hydrophobic nanowire surface while the soluble portions will explore the space around the charge of interest. Although described as an alternative to bringing the charged molecule closer to a nanowire sensor, this strategy can also be used in combination with a strategy that increases the proximity of the charged molecule to further increase the sensitivity.

Reference Nanowire

Another aspect of the invention provides for positioning a reference nanowire immediately adjacent to the nanowire bound to the polymerase. Some noise processes will be correlated between the two nanowires. Thus, a higher signal-to-noise ratio can be obtained by using the difference signal or cross-correlation signal between these two wires than can be obtained with a single nanowire or nanotube. For example, fluctuations caused by the gyration of a long strand of DNA being sequenced can be expected to have some common mode between two adjacent electrodes, and can thus be mitigated by the presence of the reference. For example, if a long strand of DNA experiences large fluctuations in position during a sequencing run, the proximity of large quantities within 100 nm or even 1000 nm can lead to a temporary increase in the rate of diffusive contacts between the DNA strand and the nanowire. These increases will read out at long timescales as an upward fluctuation in the current. If two nanowires are very close together, they would share this increase—it would happen concurrently for both wires. Thus where two very closely spaced wires are used and the polymerase is attached to one but not the other, the difference in current between the two wires will have less noise due to DNA template movements as compared the corresponding measurement using just one electrode. In some cases the measurement nanowire and the reference nanowire are between 4 nm to 30 nm apart. In some cases the measurement nanowire and the reference nanowire are between 5 nm to 20 nm apart.

Alternative Sequencing Modes

Figure 8A:
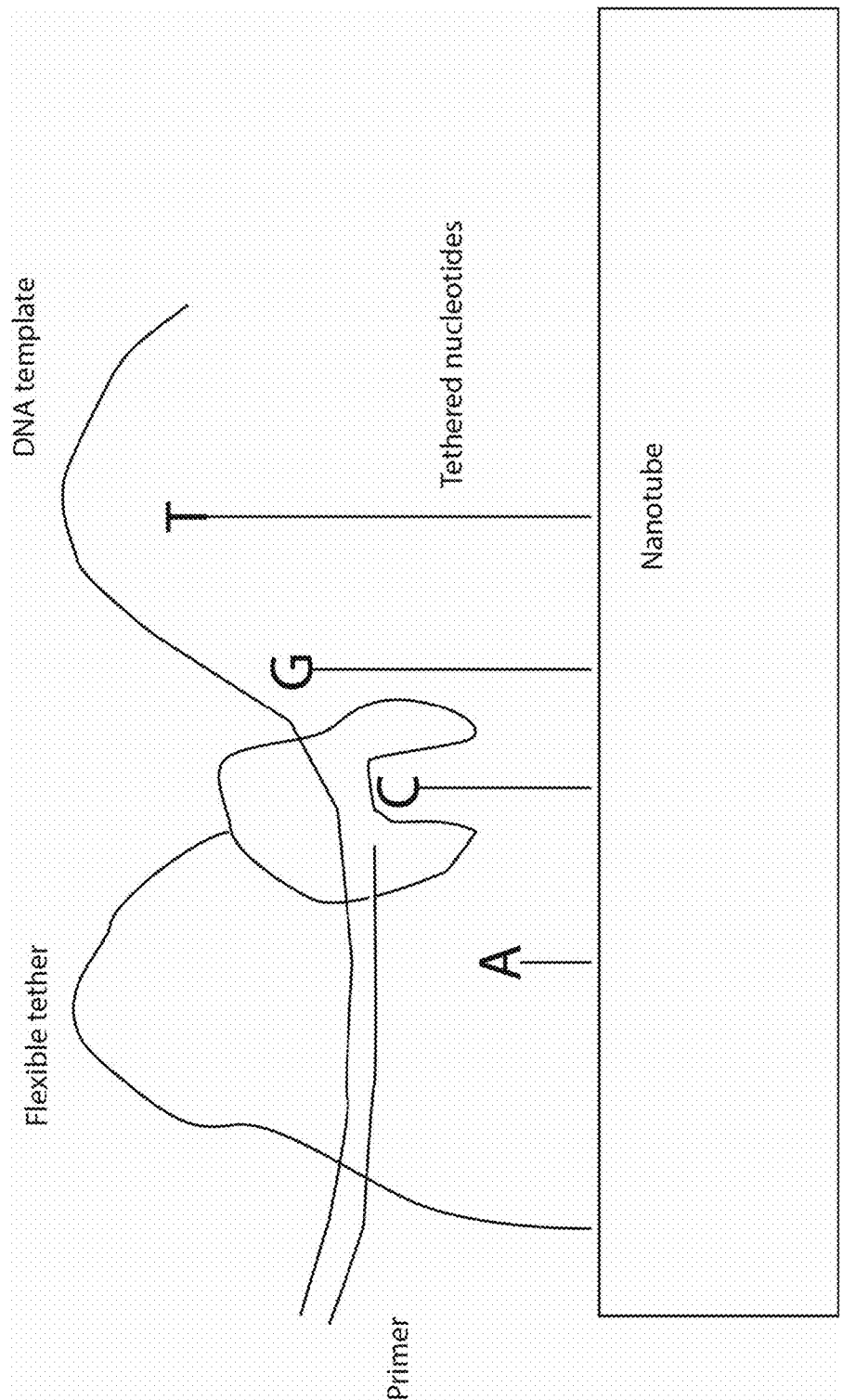
FIG. 8A shows an alternative method for nano-electronic measurement device sequencing using bound unincorporatable nucleotides.

In alternative sequencing modes of the invention, unincorporatable (e.g. nonhydrolizable) nucleotides are bound to the surface of the nanowire with different length linkers for each base. A schematic representation of such an embodiment is provided in FIG. 8A. A low concentration of free native nucleotide is provided in solution that allows the system to slowly move forward. While the polymerase is waiting for each next incorporatable base, it will repeatedly and unproductively sample against the tethered nucleotides producing a signal comprising one or more sampling events. Since the voltage or current will be affected by the length of the tether used for each base, the signal will be different for each nonhydrolizable nucleotide during the sampling events. Typically, multiple sampling events are averaged to calculate a signal that indicates which nonhydrolizable nucleotide is being sampled. Other methods for sequencing using polymerase sampling are also described in U.S. Pat. No. 8,530,164, which is incorporated herein by reference in its entirety.

Figure 8B:
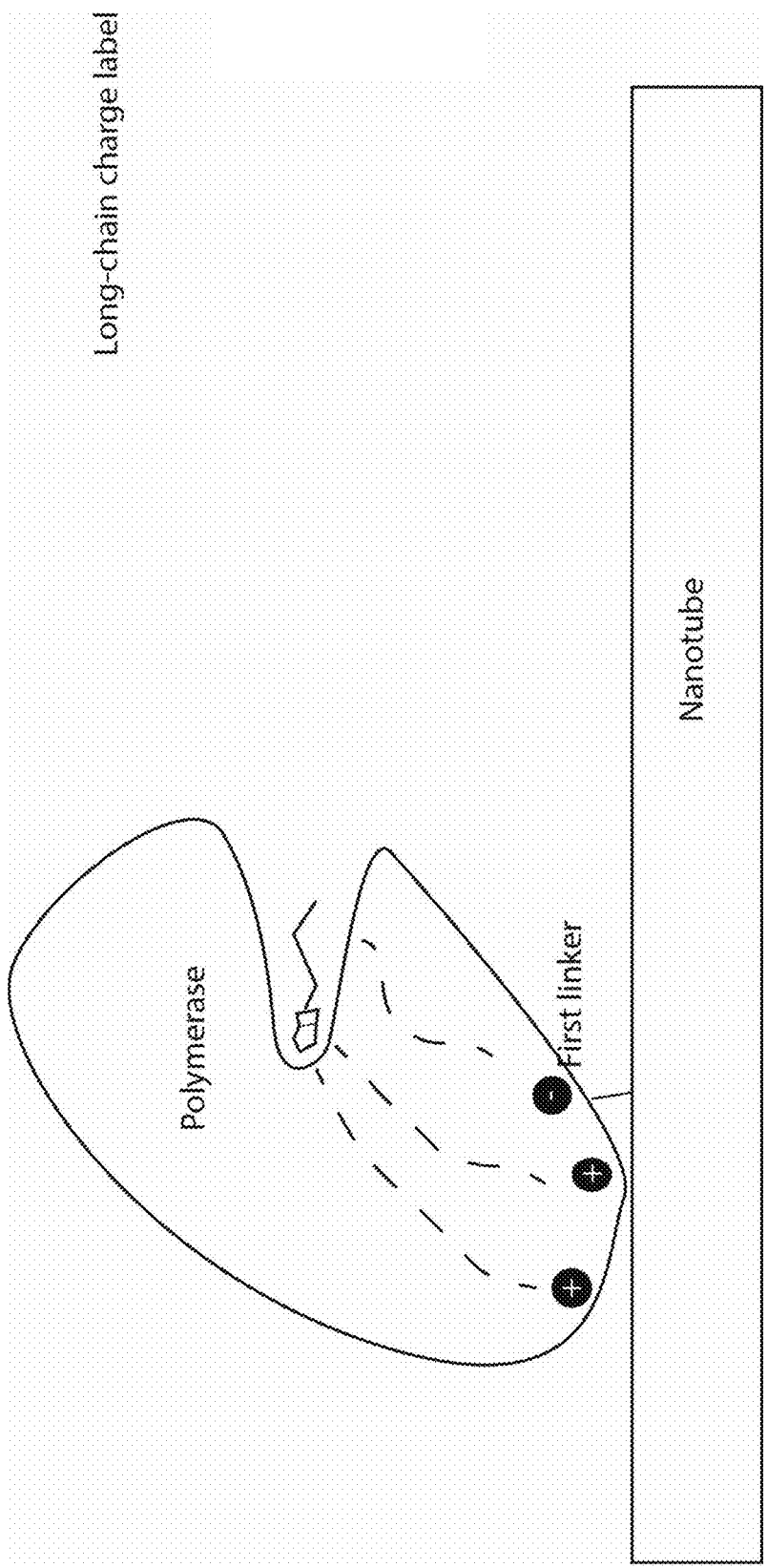
FIG. 8B shows how allosteric effects can be used to transmit the presence of a labeled nucleotide to the channel of the nano-electronic measurement device.

In other alternative sequencing modes, a polymerase is attached to a nanowire so that allosteric effects are communicated to the nanowire surface by binding in the active site, as shown in FIG. 8B. Different analogs that produce varying degrees of base-specific allosteric shifts in the structure of the polymerase are chosen and used as sequencing substrates the enzyme will use to synthesize a nascent strand.

Nano-Electronic Measurement Devices within Recessed Regions

Some aspects of the invention provide arrays of nano-electronic measurement devices in which each of the nano-electronic measurement devices is within a well or a recessed region on the substrate. In some cases the nano-electronic measurement devices are in regions recessed between about 5 nm and about 300 nm into the substrate. In some cases the nano-electronic measurement devices are in regions recessed between 10 nm and about 50 nm into the substrate. In some cases, the nano-electronic measurement devices are recessed about 10 nm, 20 nm, 30 nm, 40 nm, 50 nm, 80 nm or 100 nm into the substrate. In some cases the recessed regions can be wells that extend down into the substrate. The wells can alternatively extend into the substrate from the side (e.g. into a vertical wall of the substrate) or can extend into the substrate at any suitable angle. In some cases the recesses or wells are wider than they are deep, for example with a ratio of depth to width of about 1:2 to about 1:10, where depth is the direction of the recess. In some cases the recesses or wells are deeper than they are wide, for example with a ratio of depth to width from about 1.5:1 to about 5:1.

Nano-electronic measurement device such as carbon nanotube FET sensors are extraordinarily sensitive detectors, opening up the possibility of an electrical implementation of single molecule real time sequencing. However, in some cases, noise from the highly charged template molecule and displacement products present during the sequencing reaction can swamp the signal due to nucleotide binding due to their large size and close proximity. For this reason, in some cases it is useful to hold these long molecules away from the polymerase complex to minimize noise. In some cases, electric fields are used to electrophoretically hang or pull the charged molecules away from the detection zone. These fields can be applied either vertically (perpendicular to the substrate surface) or laterally (parallel to the substrate surface), or at a suitable angle between these.

Another approach to providing distance between these molecules and the region of the sequencing reaction is to use structural features, thus structurally biasing these molecules away from the surface. Long chain molecules experience reduced entropy when confined in a small space, and when such a molecule traverses a boundary between a confined and non-confined space the difference in entropy can lead to a free-energy gradient that produces a measurable tension in the molecule. Therefore, placing the sensing region in a recess small enough to reduce entropy of the DNA chain will not only physically displace most of the DNA molecule away just by a barrier effect, the presence of the small recess will also pull those parts of the molecule that are geometrically constrained to still reside inside constrained region and bias them away from the active sensing region of the CN-FET which is much smaller than the recessed zone.

Capacitive Filters for Improving Signal to Noise

In one aspect, the invention provides for improving the signal to noise of a circuit comprising an array of nano-electronic measurement devices but providing capacitive filters. The capacitive filters are provided as structures in solution above each nano-electronic measurement device. For example, the capacitive filter can be a layer of conductive material that is above the nano-electronic measurement device, and is typically electrically and physically connected to the substrate on which the nano-electronic measurement device is disposed. The conductive material can be, for example a planar electrode that is typically above the nano-electronic measurement device with its planar surface parallel to the substrate. The dimensions of the planar electrode can be relatively large compared to the FET. The area of the electrode can be, for example, between 4 nm squared to 500 nm squared, or from about 10 nm squared to about 100 nm squared.

In large CMOS arrays only a small fraction of the total time of one sampling cycle can be addressed to each individual device. This is the case even when there is a separate amplifier for each row, since a thousand or more devices may be served by just one amplifier and ADC. This means that the duty cycle of each device may be 0.001 or lower. In current or voltage sampling applications such as are used with addressing nano-electronic measurement devices, the noise is generally inversely related the square root of the total sampling time. So, if the duration of a sample is increased 4-fold, the noise level will be cut in half. Therefore the noise levels at a duty cycle of 0.001 could be 30 times higher than if the amplifier were In optical sensing applications, this issue can be managed by creating a floating diffusion that acts as a reservoir to store charge from incoming photons while the device waits for readout, thus escaping this scaling rule. Ironically, in devices with a very high intrinsic signal level, it is difficult to use this approach because the amount of charge produced during one cycle is very large—too large for the same kind of architecture used in light-sensing applications.

One aspect of the present disclosure provides a solution to this issue. That is to use an RC electronic filter which acts as a charge reservoir and "stores" charges between sampling events. This can shift the noise scaling curve, but requires a relatively large capacitor to create longer RC time constants. There is limited real-estate within the chip itself for constructing this capacitor structure due to the large demands of the active electronics. The invention provides for introducing these capacitive structures towards the bulk solution above the chip rather than in the substrate of the chip itself. This solution is enhanced by the fact that there is a large reservoir of conductive solution that can be used like an alternate ground-plane. Thus, the present disclosure provides relatively large-area structures placed vertically above the nano-electronic measurement devices. With appropriate selection of materials, the electrical double layer can be made non-conductive, and a relatively large capacitor area can be created with either patterned or rough side-walls. For this invention, the fluid is in-effect a self-patterning counter electrode to the nano-electronic measurement device array and provides a uniform, large area capacitor layer. These structures provide for nano-electronic measurement device arrays having higher signal to noise than devices without the capacitive structures.

Sparse Amplifier Array

One aspect of the invention is an array of nano-electronic measurement devices on a chip where the array is produced such that in operation only a small percentage of nano-electronic measurement devices is addressed, and the remainder are not used. In some cases, the percentage of nano-electronic measurement devices addressed is less than 5%, less than 2%, less than 1%, less than 0.5%, or less than 0.2% of the total number of nano-electronic measurement devices produced in the array. This aspect of the invention can be accomplished by the structure of the chip, the methods of addressing the chip, the methods of analyzing the chip, and combinations of any of these. In some cases, active switching of dedicated amplifiers is used to selectively address productive nano-electronic measurement devices having a single nanotube and single biomolecule (e.g. polymerase complex). In some preferred aspects, nano-electronic measurement devices of the invention are produced using carbon nanotubes in combination with CMOS electronics.

For example, in some aspects the invention provides a method of addressing and analyzing a nano-electronic measurement device chip where, after the nano-electronic measurement devices array is produced, and after the biological molecule of interest such as the polymerase enzyme complex is attached, the chip is probed electrically to determine which of the nano-electronic measurement devices have a single nanotube and a single biomolecule such as a polymerase. Then, during the measurement phase, for example, nucleic acid sequencing, only the nano-electronic measurement devices having both a single nanotube and a single biomolecule (the productive nanoFETs) are addressed and analyzed. In a preferred method, the signals to the chip are re-configured such that the non-productive nano-electronic measurement devices are completely bypassed. Moreover, in some embodiments, the nano-electronic measurement devices are analyzed on a recurring basis to ascertain which of the nano-electronic measurement devices have both a single nanotube and a single biomolecule (the productive nanoFETs). While it may seem counterintuitive to produce an array where only a small fraction of devices are used, we have found that unlike other uses of transistor arrays, the requirement of a single nanotube with a single polymerase, or other channel/polymerase format disclosed herein, will typically result in only a small number of the nano-electronic measurement devices having both a single nanotube and a single biomolecule (the productive nanoFETs) being used. With the devices and methods of the invention, we have developed ways of producing effective devices by actively using only the devices that are productive. In some cases, a chip is produced having 100 million or more nano-electronic measurement devices, and when in use, for example nucleic acid sequencing, 2 million or fewer nano-electronic measurement devices are addressed and measured. This approach saves electronic and memory resources, and can provide higher quality information than for a chip where all or a majority of the nano-electronic measurement devices are addressed and measured. Moreover, this approach speeds up chip read out time as available amplifiers are dedicated to always reading out from productive nano-electronic measurement devices. Moreover, in some embodiments, this approach reduces stray or unwanted capacitance on the chip as a majority of the nano-electronic measurement devices on the chip are electrically not read and thus do not contribute to unwanted stray capacitance.

For example say there are 1.7M nano-electronic measurement devices in an array on a chip. This means 1.7 M pairs of electrodes that could be bridged by zero, one, two or more nanotubes. We can typically only use those nano-electronic measurement devices that have a single tube bridging. Even if we model the system that 100% of the tubes we transfer are potentially active (not multi-walled, not too big, etc.) we can only get 37% of the electrode pairs to be useful if we use single entity loading based on Poisson statistics. If there is contamination of non-useful, for example, short-circuit producing nanotubes, this fraction will get directly multiplied by the efficiency above, so if there are 50% quality nanotubes we will get 18% active device fraction, and if there are 10% quality nanotubes we will get 3.7% active device fraction. In addition, where these nanotubes are subsequently derivitized, e.g. with a carboxylate moiety, if the derivitization is controlled by Poisson statistics, only 37% of these will be useful.

At this stage we would attach the biomolecule to the derivitized nanotubes (or other form of channel disclosed herein), for example, the attachment of the polymerase sequencing complex. This reaction will have a yield, which will be affected, for example, by the fraction of polymerase enzyme that is active. It is expected that this step can also result in a significant loss of yield of productive nano-electronic measurement devices. Thus, even for a relatively well developed protocol, the yield of productive nano-electronic measurement devices having a single nanotube and single polymerase will be relatively small in the range, for example of between 2% to 0.2%.

A solution provided as part of this invention is to make a chip with a vast over-supply of nano-electronic measurement devices, but use an amplifier architecture that can handle only small fraction of that output. For example, we put 200,000,000 pixels (addressed nano-electronic measurement devices) onto a single die (chip), then with 0.5% useful fraction this is yields 1,000,000 active useful nano-electronic measurement devices. The output amplifiers are arranged such that even if a larger fraction of the nano-electronic measurement devices were useful, they would never have the bandwidth to read them all out.

Figure 14A:
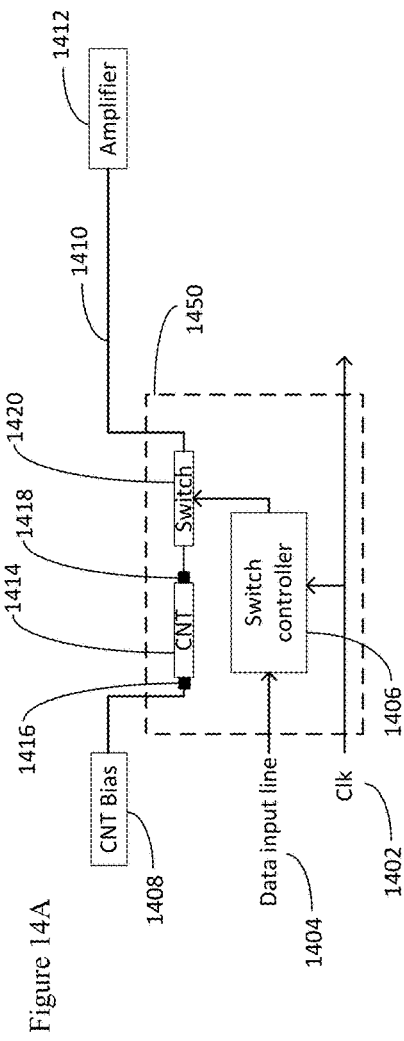
FIG. 14A illustrates a sparse amplifier array with a switch controller for nucleic acid sequencing in accordance with an embodiment of the present disclosure.

One aspect of the present disclosure provides a sparse amplifier array in the form of an integrated circuit. The integrated circuit comprises a substrate and a plurality of sectors arranged on the substrate. FIG. 14A illustrates one such sector of the sparse amplifier array. In some embodiments a sparse amplifier array comprises one hundred or more such sectors, one thousand or more such sectors, one hundred thousand or more such sectors, or a million or more such sectors on a single chip. In FIG. 14A, each sector in the plurality of sectors comprises a first clock signal line 1402, a data input line 1404, and a switch controller that is in electrical communication with the first clock signal line 1402 and the data input line 1404. The sector further comprises a counter bias line 1408 and an amplifier input line 1410, also referred to as a common measurement bus line. The amplifier input line 1410 is in electrical communication with an amplifier 1412. In some embodiments, the amplifier 1412 is not on the chip. In some embodiments, the amplifier 1412 is on the chip. The sector further comprises a plurality of nano-electronic measurement devices spatially arranged on the substrate of which one such nano-electronic measurement device 1414 is depicted in FIG. 14A. Each respective nano-electronic measurement device 1414 in the plurality of nano-electronic measurement devices includes a source 1416 that is coupled to the counter bias line 1408 and a drain 1418 that is coupled to the amplifier input line 1410 thereby obtaining an electrical signal on the drain 1418 of the respective nano-electronic measurement device. As disclosed herein, the electrical signal is any one of a discrete set of electrical signals and an identity of the electrical signal in the discrete set of electrical signals is determined by an electrical interaction between the corresponding nano-electronic measurement device 1414 and a particular charge label in a plurality of charge labels. The sector further comprises a plurality of switches of which one is illustrated in FIG. 14A. Each switch 1420 in the plurality of switches gates the electrical signal between the drain 1418 of a corresponding nano-electronic measurement device 1414 in the plurality of nano-electronic measurement devices and the amplifier input line 1410 between (i) an on state, in which the electrical signal at the drain 1418 of the corresponding nano-electronic measurement device 1414 is delivered to the amplifier input line 1410, and (ii) an off state, in which the electrical signal at the drain 1418 of the corresponding nano-electronic measurement device 1414 is not delivered to the amplifier input line 1410. Each respective switch 1420 in the plurality of switches is independently wired to the switch controller 1406 thereby causing the respective switch 1420 to be in one of the on state and the off state responsive to the switch controller 1406 as a function of a clock pulse on the first clock signal line 1402 and a data input 1404 on the data input line.

Figure 14B:
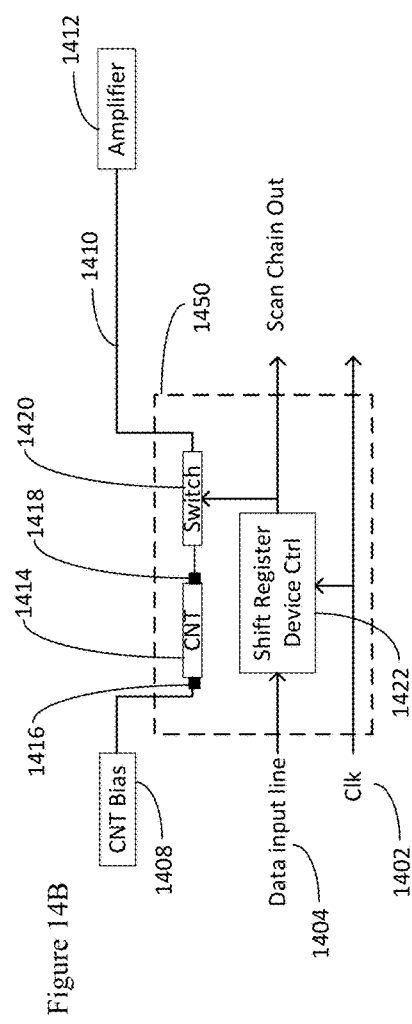
FIG. 14B illustrates a sparse amplifier array in accordance with FIG. 14A in which the switch controller comprises a shift register in accordance with an embodiment of the present disclosure.
Figure 15:
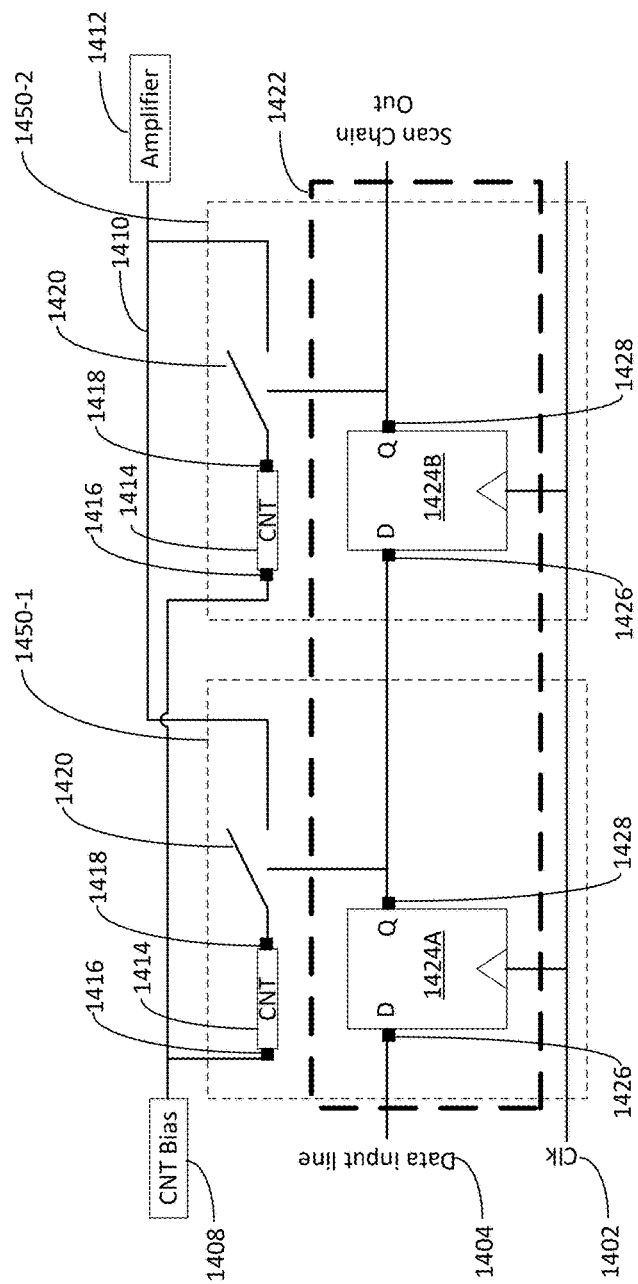
FIG. 15 illustrates a sparse amplifier array in accordance with FIG. 14B in greater detail in accordance with an embodiment of the present disclosure.

FIG. 14B illustrates a particular embodiment of the sparse amplifier array of FIG. 14A in which the switch controller 1406 of a sector in the plurality of sectors comprises a first shift register 1422. The shift register is capable of shifting its binary information either to the right or to the left. In the illustration of FIG. 14B, the shift is to the right, however, in alternative configurations not shown, the shift is to the right. The logical configuration of a shift register 1422 consists of a chain of flip-flops connected in cascade, with the output of one flip-flop connected to the input of the next flip-flop. All flip-flops receive the common clock pulse from the first clock signal line 1402 which causes the shift from one stage to the next. The simplest possible shift register is one that uses only flip-flops, as illustrated in FIG. 15, however more complex shift registers are encompassed by the teachings of the present disclosure and any known shift register may be used as shift register 1422. See Mano, *Digital Logic and Computer Design*, Prentice-Hall, Inc., Englewood Cliffs, N.J., 1979, Section 7-3, pp. 263-264, which is hereby incorporated by reference.

Turning to FIG. 15, an example first shift register 1422 in accordance with an embodiment of the present disclosure is illustrated in greater detail. The first shift register comprises a first plurality of flip-flops in electrical communication with the first clock signal line 1402. The first plurality of flip-flops comprises an initial flip-flop 1424A and a terminal flip-flop 1424B and any number of intermediate flip-flops 1424 (not shown) in serial communication with each other between the initial flip-flop 1424A and the terminal flip-flop 1424B. Each flip-flop 1424 includes a serial input 1426 and a serial output 1428. A flip-flop circuit can maintain a binary state indefinitely (as long as power is delivered to the circuit) until directed by an input signal to switch states. One difference among various flip-flops are in the number of inputs they possess and in the manner in which the inputs affect the binary state. See Mano, *Digital Logic and Computer Design*, Prentice-Hall, Inc., Englewood Cliffs, N.J., 1979, Section 6-2, pp. 204-210, which is hereby incorporated by reference. In FIG. 15, the serial output 1428 of each flip-flop 1424 in the first plurality of flip-flops, other than the terminal flip-flop 1424B, is uniquely electrically connected to the serial input 1426 of another flip-flop 1424 in the first plurality of flip-flops, thereby electrically coupling the first plurality of flip-flops in series. In other words, referring to FIG. 15, the Q output of a given flip-flop is connected to the D input of the flip-flip to its right. Each clock pulse on clock 1402 shifts the contents of the register 1422 one bit position (one flip-flop) to the right. The serial input on the data input line 1404 determines what goes into the input D of the leftmost flip-flop 1424A during this shift. Thus, the serial input 1426 (D) of the initial flip-flop 1424A is electrically connected to the data input line 1404. In this way, the first shift register 1422 is configured to receive a device scan chain sequence, from the data input line 1404, that is propagated through the first plurality of flip-flops by electrical pulses in the first clock signal line 1420 thereby independently biasing each flip-flop 1424 in the first plurality of flip-flops to one of a first state and a second state. Each respective switch 1420 in the plurality of switches is independently wired to the switch controller 1422 through the output 1428 of a corresponding flip-flop 1424 in the first plurality of flip-flops thereby causing the respective switch 1420 to be in the off state when the corresponding flip-flop 1424 is biased to the first state and causing the respective switch 1420 to be in the on state when the corresponding flip-flop 1424 is biased to the second state.

Thus the sparse amplifier array illustrated in FIG. 15 is logically arranged into pixels 1450, where every pixel includes a nano-electronic measurement device 1414 associated with a flip-flop 1424 and a switch 1420 capable of routing the output of pixel to a common amplifier 1412. When a switch 1420 is turned on, the path between the pixel 1450 and the amplifier 1412 is completed and the nano-electronic measurement device 1414 within the pixel 1450 can be measured by the amplifier 1412. Measurement is typically performed by a transimpedance amplifier, which converts a nano-electronic measurement device 1414 current (across the channels of the device) into an output voltage. When a switch 1420 is turned off, the pixel 1450 is disconnected from the amplifier 1412. As illustrated in FIG. 15, switches 1420 are controlled by serially loading data into the scan chain. Only one nano-electronic measurement device 1414 will be measured at a time (per amplifier), corresponding to the pixel that contains a logic high (1) within its flip-flop 1424. To measure the next device 1414, the clock signal is asserted on the first clock signal line 1420, which shifts the logic high measurement value over by one flip-flop 1424. If the next measurement device 1414 to be measured is not adjacent to the current measurement device, the clock signal is cycled multiple times until the logic high value is placed into the next appropriate flip-flop 1424. The pixels 1450 may be arranged in a linear fashion, or they may serpentine across the chip, covering multiple rows and columns. In the sparse amplifier array illustrated in FIG. 14, it is necessary to push the data regarding which devices 1414 to measure using a scan chain fed into the shift register on the data input line 1404 by a varying number of clock pulses to jump between functional devices 1414. Further, in the sparse amplifier array illustrated in FIG. 14, each pixel 1450 has an independent memory element (the associated flip-flop 1414).

Figure 16:
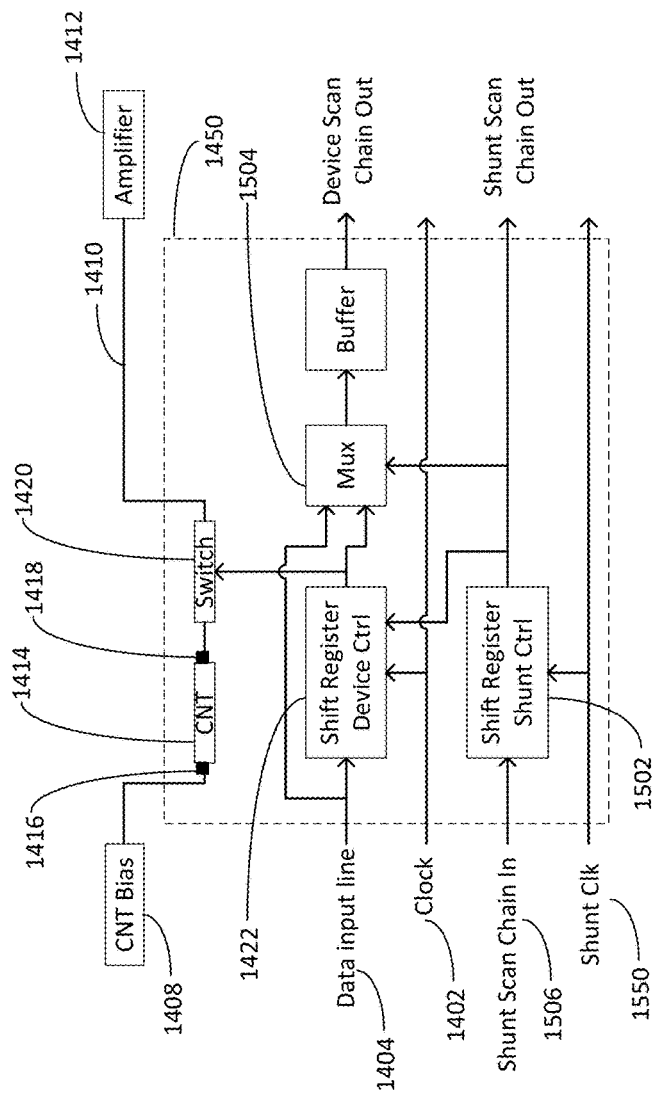
FIG. 16 illustrates a sparse amplifier array for nucleic acid sequencing that includes first and second shift registers in accordance with an embodiment of the present disclosure.

FIG. 16 illustrates a particular embodiment of the sparse amplifier array in accordance with another aspect of the present disclosure. This architecture builds upon the scan chain architecture described above in conjunction with FIGS. 14 and 15 above. The sparse amplifier array includes a second flip flop in each pixel 1450 as part of a shunt shift register 1502. This second flip-flop can control whether a pixel 1450 should be shunted under the circumstance where the nano-electronic measurement device 1414 within the pixel 1450 should not be measured (or if there is no device at all). The shunt is achieved by controlling a multiplexer (MUX) 1504 that can route the device scan chain in signal around a flip-flop. To program this architecture, data is first serially loaded into as a shunt scan chain onto the shunt scan chain in line 1506. This will define which flip flops should be shunted and which should not. Once the shunt scan chain is completely loaded, a single measurement logic high value will be sent through as a device scan chain on the data input line 1404. At each pulse of the first clock signal line 1402, the next non-shunted device will receive the measurement logic high value, routing that pixel's the nano-electronic measurement device to the amplifier 1412. The sparse amplifier array of FIG. 16 requires increased silicon real estate relative to the sparse amplifier array of FIG. 15 for the additional flip flop and associated logic circuitry.

Figure 17:
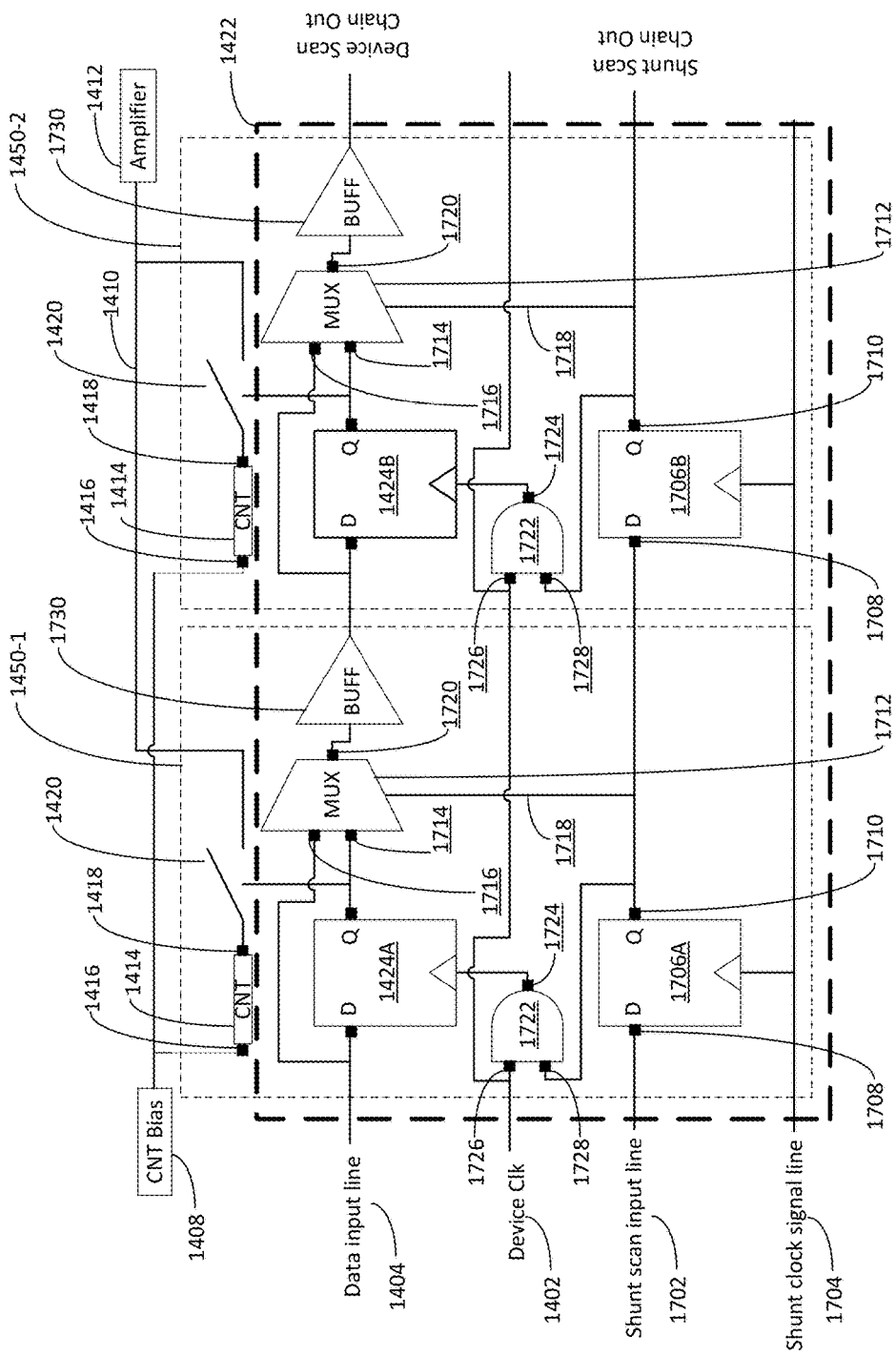
FIG. 17 illustrates a sparse amplifier array in accordance with FIG. 16 in greater detail in accordance with an embodiment of the present disclosure.

FIG. 17 illustrates the sparse amplifier array of FIG. 16 in greater detail, in which a sector in the plurality of sectors further comprises a shunt scan chain input line 1702 and a shunt clock signal line 1704. The switch controller 1422 further comprises a second shift register comprising a second plurality of flip-flops in electrical communication with the shunt clock signal line 1704. The second plurality of flip-flops comprises an initial flip-flop 1706A and a terminal flip flop 1706B. Each flip-flop in the second plurality of flip-flops includes a serial input 1708 and a serial output 1710. The serial output 1710 of each flip-flop 1706 in the second plurality of flip-flops, other than the terminal flip-flop 1706B, is uniquely electrically connected to the serial input 1708 of another flip-flop in the second plurality of flip-flops, thereby electrically coupling the second plurality of flip-flops in series. The serial input 1708 of the initial flip-flop 1706 in the second plurality of flip-flops is electrically connected to the shunt scan chain input line 1702. In this way, the second shift register is configured to receive a shunt scan chain sequence that is propagated through the second plurality of flip-flops by electrical pulses in the shunt clock signal line 1704, thereby independently biasing each flip-flop 1706 in the second plurality of flip-flops to one of a third state (e.g., a logical "1" state) and a forth state (e.g., a logical "0" state). The switch controller of the sparse amplifier array depicted in FIG. 17 further comprises a plurality of multiplexers. A multiplexer is a combinational circuit that selects binary information from one of many input lines and directs it to a single output line. The selection of a particular input line is controlled by one or more input lines. See Mano, *Digital Logic and Computer Design*, Prentice-Hall, Inc., Englewood Cliffs, N.J., 1979, Section 5-6, pp. 175-178, which is hereby incorporated by reference, for more information on multiplexers. As such, a broad range of multiplexers may be used in the present disclosure. What is described here are the minimum requirements for the sparse amplifier array of FIGS. 16 and 17. As such, each multiplexer 1712 in the plurality of multiplexers comprises at least a first input line 1714, a second input line 1716, a select line 1718, and an output line 1720. The first input line 1714 of each respective multiplexer 1712 in the plurality of multiplexers is in electrical communication with the serial output Q of a first corresponding flip-flop 1414A in the first plurality of flip-flops. The second input line 1716 of each respective multiplexer 1712 in the plurality of multiplexers is in electrical communication with the serial input D of the first corresponding flip-flop 1424 in the first plurality of flip-flops. The select line 1718 of each respective multiplexer 1712 in the plurality of multiplexers is in electrical communication with the serial output Q 1710 of a first corresponding flip-flop 1706 in the second plurality of flip-flops. The output line 1720 of each respective multiplexer 1712 in the plurality of multiplexers is in electrical communication with the serial input D of a second corresponding flip-flop 1424 in the first plurality of flip-flops.

The switch controller 1422 of the sparse amplifier array depicted in FIG. 17 further comprises a plurality of AND gates. Each AND gate 1722 in the first plurality of AND gates comprises an output 1724, a first input 1726 and a second input 1728. The first input 1726 of each respective AND gate 1722 in the first plurality of AND gates is in electrical communication with the first clock signal line 1402. The second input 1728 of each respective AND gate 1722 in the first plurality of AND gates is in electrical communication with the serial output 1710 of the first corresponding flip-flop 1706 in the second plurality of flip-flops. Each respective flip-flop 1424 in the first plurality of flip-flops is in electrical communication with the first clock signal line 1402 through the output 1714 of a corresponding AND gate 1722 in the first plurality of AND gates. Thus, when a respective flip-flop 1706 in the second plurality of flip-flops, that is in electrical communication with the second input 1728 of the respective AND gate, is in the third state, the first clock signal line 1402 is not applied to the respective flip-flop 1424 in the first plurality of flip-flops and the select line 1718 of the multiplexer in the plurality of multiplexers that is in electrical communication with the output 1710 of the respective flip-flop 1706 in the second plurality of flip-flops is biased to the second input line 1716 of the respective multiplexer. Conversely, when the flip-flop 1706 in the second plurality of flip-flops, that is in electrical communication with the second input 1728 of the respective AND gate, is in the fourth state, the first clock signal line 1402 is applied to the respective flip-flop 1424 in the first plurality of flip-flops and the select line 1718 of the multiplexer 1712 in the plurality of multiplexers that is in electrical communication with the output 1710 of the respective flip-flop 1706 in the second plurality of flip-flops is biased to the first input line 1714 of the respective multiplexer.

In some embodiments, the output line 1720 of each respective multiplexer 1712 in the plurality of multiplexers is in electrical communication with the serial input D of a second corresponding flip-flop 1424 in the first plurality of flip-flops through a corresponding buffer gate 1730 in a plurality of buffer gates as illustrated in FIG. 17. In some embodiments each respective multiplexer 1712 in the plurality of multiplexers is in electrical communication with the serial input D of a second corresponding flip-flop 1424 in the first plurality of flip-flops directly without making use of such a buffer gate.

Figure 18:
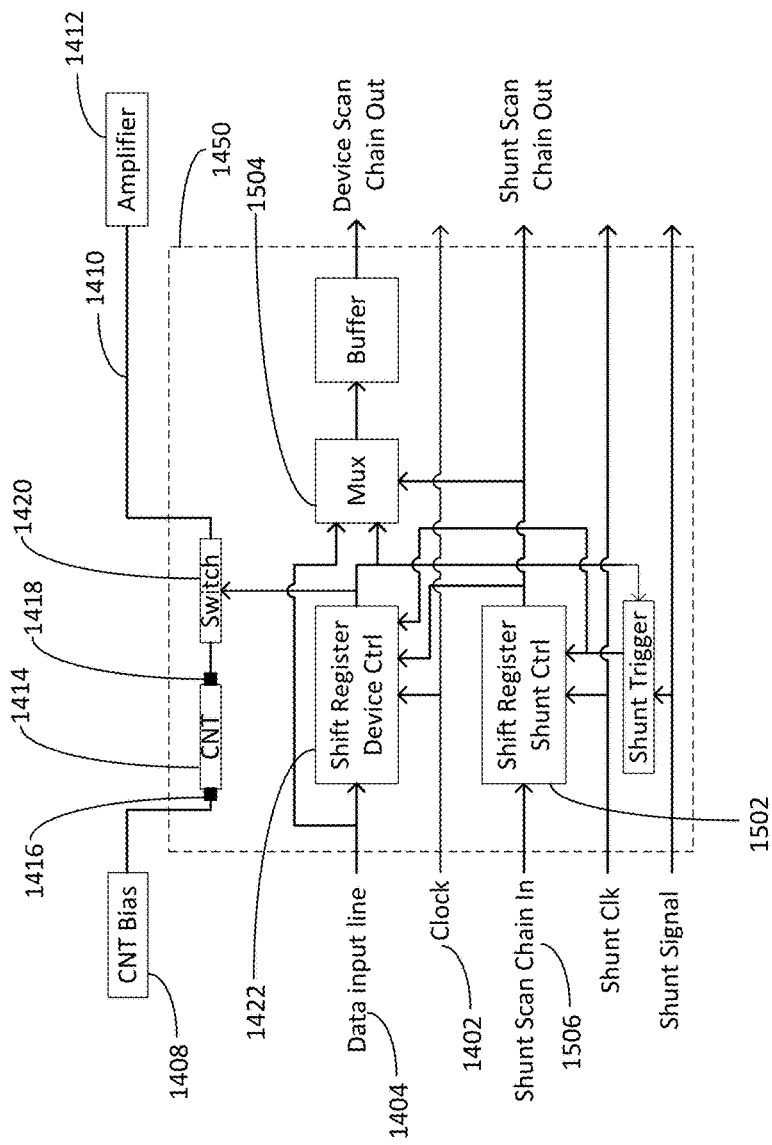
FIG. 18 illustrates a sparse amplifier array for nucleic acid sequencing that includes first and second shift registers and includes a shunt signal and asynchronous reset inputs to the flip flops of the shift registers in accordance with an embodiment of the present disclosure.

FIG. 18 illustrates a particular embodiment of the sparse amplifier array in accordance with another aspect of the present disclosure. This architecture builds upon the scan chain architecture described above in conjunction with FIGS. 16 and 17 above. The sparse amplifier array further includes a shunt signal and asynchronous reset inputs to the flip flops. The shunt signal allows a pixel 1450 to be set to 'shunt' by asserting the asynchronous reset signal at the same time that a pixel is being measured. This feature allows pixels to be removed from the scan chain without having to reload the entire shunt scan chain.

Figure 19:
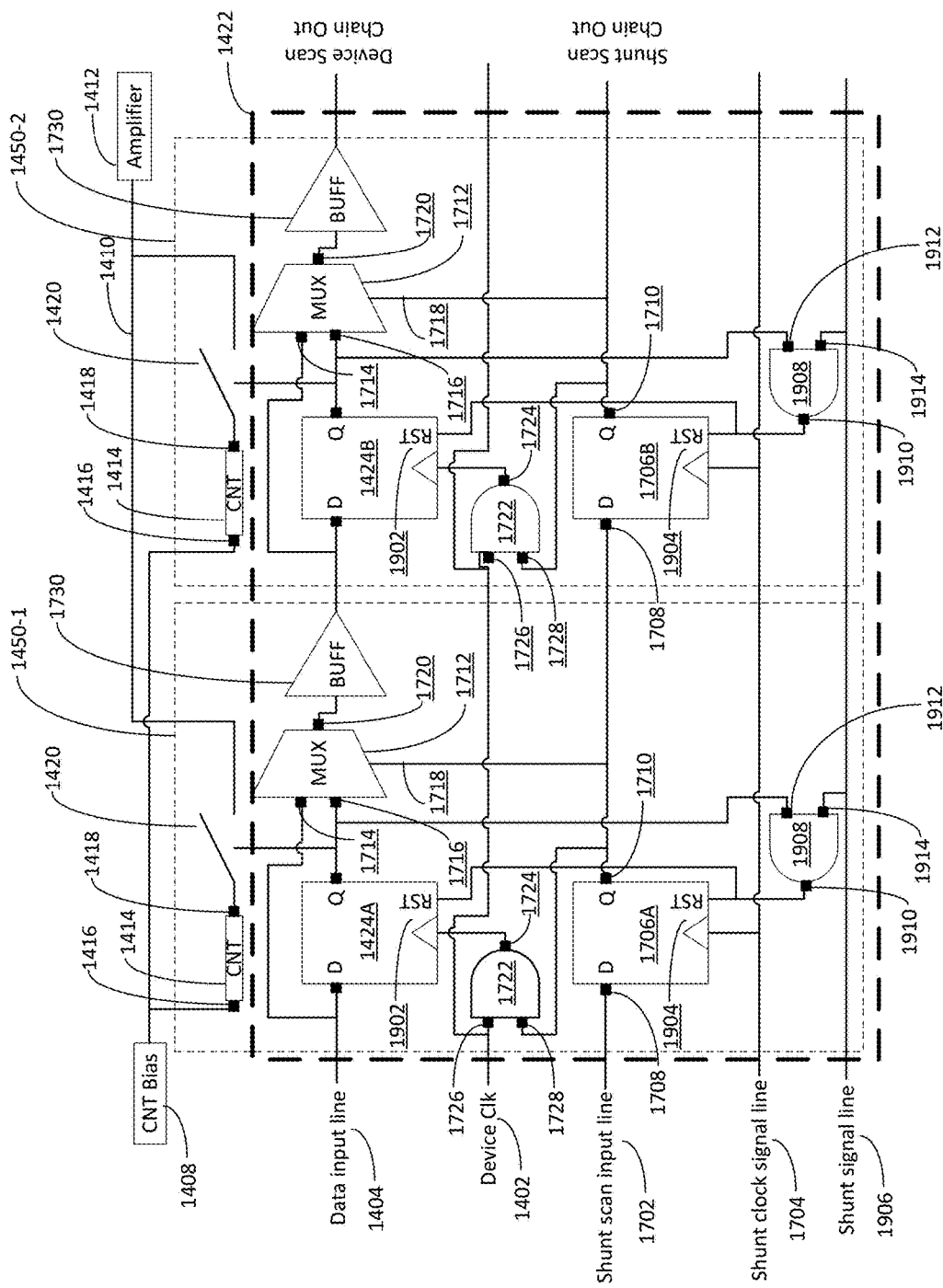
FIG. 19 illustrates a sparse amplifier array in accordance with FIG. 18 in greater detail in accordance with an embodiment of the present disclosure.

FIG. 19 illustrates the sparse amplifier array of FIG. 18 in greater detail. Each flip-flop 1424 in the first plurality of flip-flops further comprises a first reset 1902. Each flip-flop 1706 in the second plurality of flip-flops further comprises a second reset 1904. Each sector of the sparse amplifier array further comprises a shunt signal line 1906. The switch controller 1422 further comprises a second plurality of AND gates. Each AND gate 1908 in the second plurality of AND gates has an output 1910, a first input 1912 and a second input 1914. The first input 1912 of each respective AND gate 1908 in the second plurality of AND gates is in electrical communication with the serial output Q of a first flip-flop 1424 in the first plurality of flip-flops. The second input 1914 of each respective AND gate 1908 in the second plurality of AND gates is in electrical communication with the shunt signal line 1906. The output 1910 of each respective AND gate 1908 in the second plurality of AND gates is in electrical communication with the first reset 1716 of the corresponding flip-flop 1424 in the first plurality of flip-flops and the second reset 1904 of a corresponding flip-flop 1706 in the second plurality of flip-flops, thereby causing the first corresponding flip-flop 1424 to reset to the first state and the second corresponding flip-flop 1706 to reset to the third state when the shunt signal line 1906 is asserted at the same time that the nano-electronic device 1414 in electrical communication with the first corresponding flip-flop 1424 is driven 1408 by the data input line 1404 to the second state. Thus, in a given pixel 1450, when the flip-flop 1424 is in the second state, meaning that the corresponding switch 1420 is closed (in the on state) and the nano-electronic measurement device 1414 is being measured by the amplifier 1412, a signal on the shunt signal line 1906 will pass through the AND gate 1908 and reset the flip-flop 1424 to the first state, thereby opening the switch 1420 (setting the switch to the off states) and resetting the flip-flop 1706 to the third state thereby causing the scan chain on the data input line 1404 to permanently bypass the pixel 1450.

Figure 20:
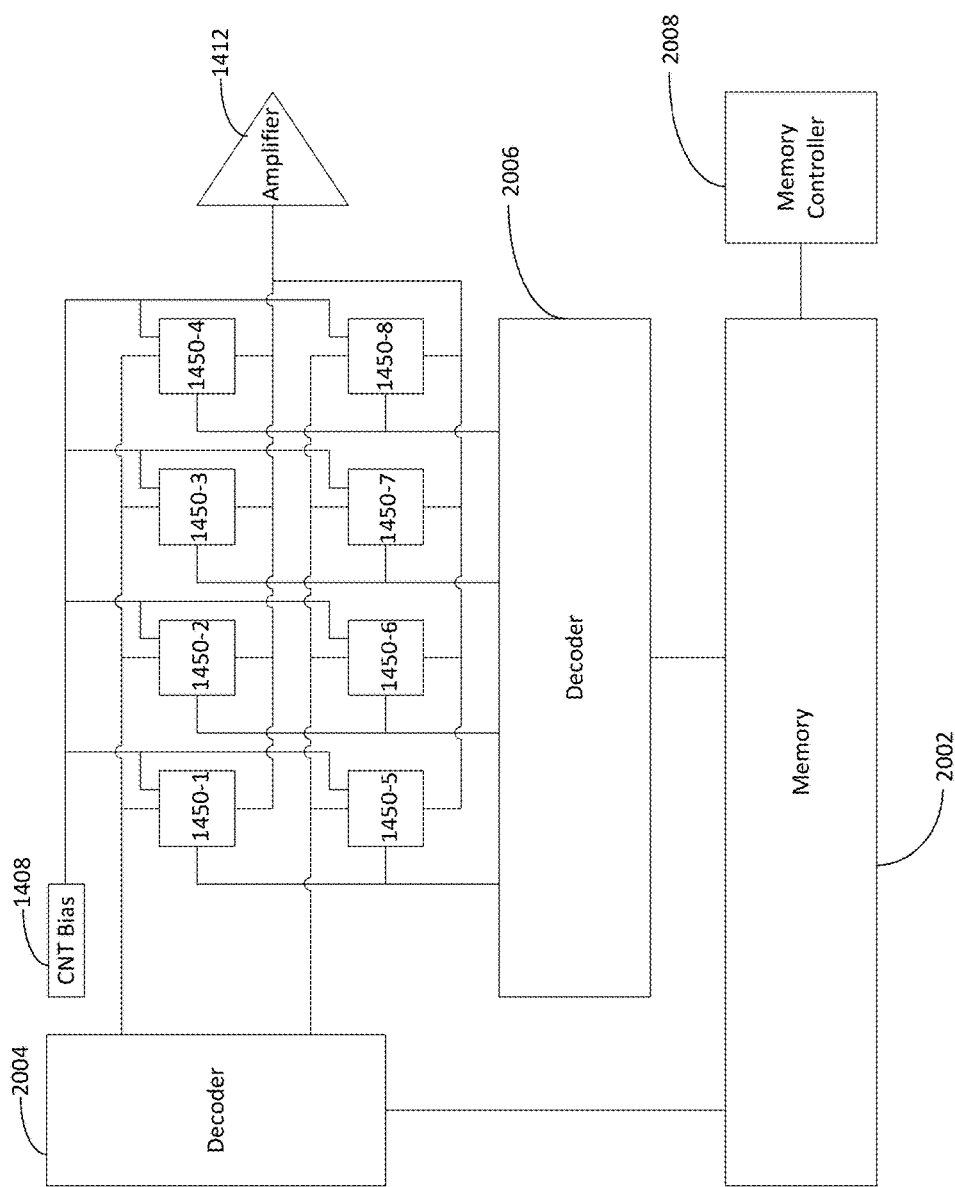
FIG. 20 illustrates a sparse amplifier array for nucleic acid sequencing with a memory bank that can store the address of N functional devices, and in which two decoders, with inputs driven by the memory bank, are used to select a device, in accordance with an embodiment of the present disclosure.

FIG. 20 illustrates a particular embodiment of the sparse amplifier array in accordance with another aspect of the present disclosure. The sparse amplifier array of FIG. 20 comprises one hundred or more such sectors, one thousand or more such sectors, one hundred thousand or more such sectors, or a million or more such sectors on a single chip, and FIG. 20 illustrates one such sector. Each sector of the sparse amplifier array of FIG. 20 has a memory bank 2002 that can store the address of N functional nano-electronic measurement devices 1414 within the sector. Two decoders, a row decoder 2004 and a column decoder 2006, with inputs stored in the memory bank 2002, are used to select a nano-electronic measurement device 1414. In particular, in some embodiments, the memory bank 2002 stores a single bit for each pixel 1450, where one value of the pixel indicates that the corresponding pixel is to read and the other value of the pixel indicates that the corresponding pixel is not to be read. The decoders are used to select the row and column of a nano-electronic measurement device 1414 that is to be read, routing the output of one such device 1414 (e.g., the current across the channel of the device) to an amplifier 1412. This architecture allows direct addressing of any pixel 1450 in the array, where each such pixel includes a nano-electronic measurement device 1414, and pixels can be selected in any order, and any number of pixels can be permanently sealed from reading because their measurement devices 1414 are not functional. The size N of the memory bank 2002 is designed by estimating the number of anticipated functional devices 1414 in the sector.

Figure 21:
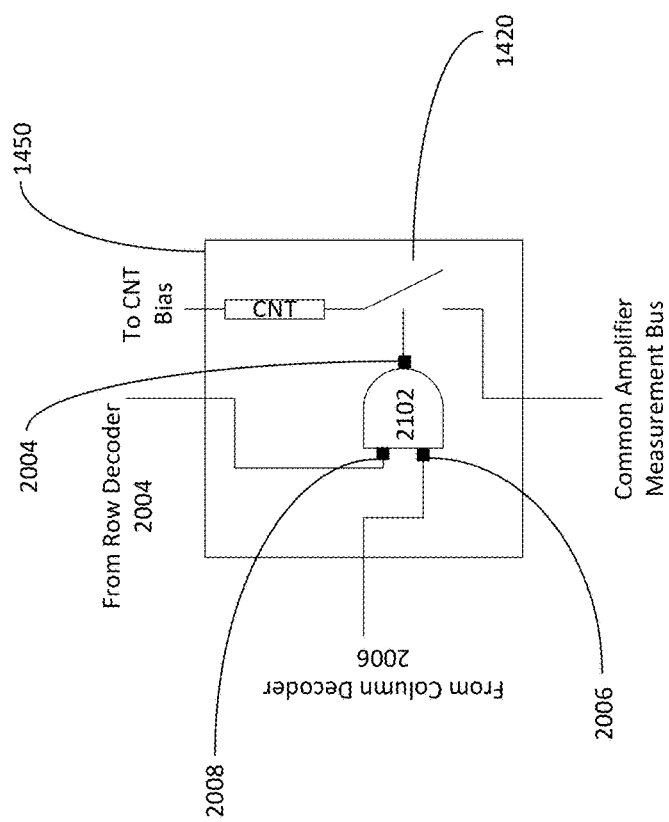
FIG. 21 illustrates the logic around each device in the sparse amplifier array of FIG. 20 in accordance with an embodiment of the present disclosure.

Referring to FIGS. 20 and 21, the depicted embodiment of the sparse amplifier array includes a plurality of sectors of which one is shown. Each sector is associated with an amplifier 1412 and includes a switch controller comprising a memory 2002 in electrical communication with the memory controller 2008, a column decoder 2006 in electrical communication with the memory 2002, and a row decoder 2004 in electrical communication with the memory 2002. Referring to FIG. 21, the sector further comprises a plurality of AND gates. Each AND gate 2102 in the plurality of AND gates comprises an output 2004, a first input 2006 and a second input 2008. The first input 2006 of each respective AND gate 210 in the plurality of AND gates is in electrical communication with the column decoder 2006. The second input 2008 of each respective AND gate 2102 in the plurality of AND gates is in electrical communication with the row decoder 2004. Each respective switch 1420 in the plurality of switches is independently wired to the switch controller through the output 2004 of a corresponding AND gate 2102 in the plurality of AND gates, thereby causing the respective switch 1420 to be in the on state when the row decoder 2004 and the column decoder 2006 both signal a first state to the corresponding AND gate 2102 and otherwise causing the respective switch 1420 to be in the off state.

Figure 22:
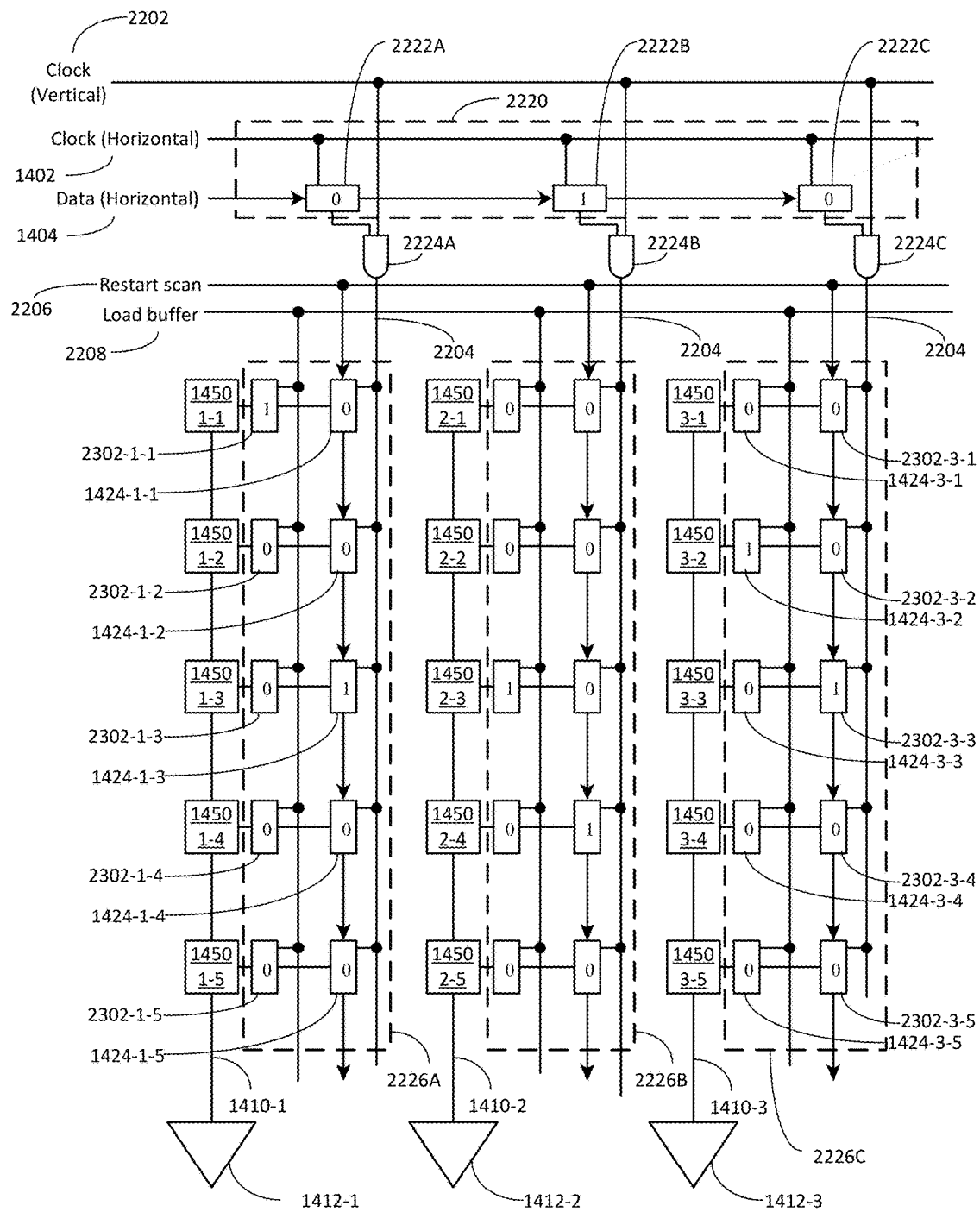
FIG. 22 illustrates a sparse amplifier array, for nucleic acid sequencing, in a first state in a horizontal shift register is loaded with data, a single bit for each column, and then N pulses are applied to the vertical shift clock, and in which, by an appropriate choice of bits and choices of N, any number of shifts can be implemented independently on each column in accordance with an embodiment of the present disclosure.
Figure 23:
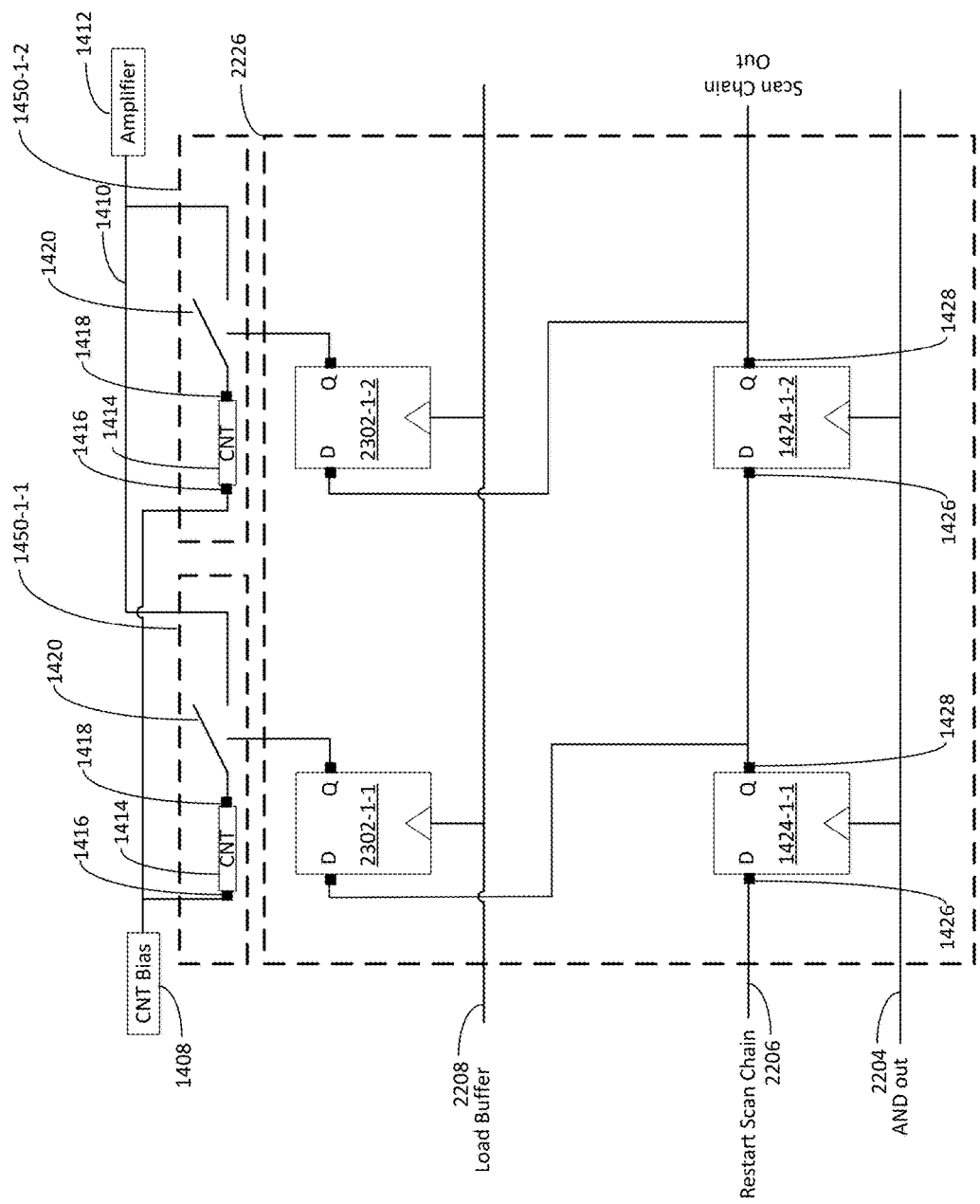
FIG. 23 illustrates more details of the sparse amplifier array of FIG. 22 in accordance with an embodiment of the present disclosure.

FIG. 22 illustrates a particular embodiment of a sparse amplifier array in accordance with another aspect of the present disclosure. FIG. 23 illustrates a more detailed embodiment of the sparse amplifier array of FIG. 22. The integrated circuit comprises a substrate (not shown in FIG. 22) and a plurality of sectors arranged on the substrate. FIG. 22 illustrates one such sector of the sparse amplifier array. In some embodiments the sparse amplifier array comprises one hundred or more such sectors, one thousand or more such sectors, one hundred thousand or more such sectors, or a million or more such sectors on a single chip. In FIG. 22, each sector in the plurality of sectors comprises a first clock signal line 1402 and a data input line 1404. The sector further comprises a counter bias line 1408 (not shown in FIG. 22, but shown in FIG. 23) and an amplifier input line 1410, also referred to as a common measurement bus line. Each amplifier input line 1410 is in electrical communication with a corresponding amplifier 1412. In some embodiments, the corresponding amplifier 1412 is not on the chip. In some embodiments, the corresponding amplifier 1412 is on the chip. Referring to FIG. 23, the sector further comprises a plurality of nano-electronic measurement devices 1424 spatially arranged on the substrate in pixels 1450. As shown in more detail in FIG. 23, each respective nano-electronic measurement device 1414 in the plurality of nano-electronic measurement devices includes a source 1416 that is coupled to the counter bias line 1408 and a drain 1418 that is coupled to the amplifier input line 1410 thereby obtaining an electrical signal on the drain 1418 of the respective nano-electronic measurement device 1414. As disclosed herein, the electrical signal is any one of a discrete set of electrical signals and an identity of the electrical signal in the discrete set of electrical signals is determined by an electrical interaction between the corresponding nano-electronic measurement device 1414 and a particular charge label in a plurality of charge labels. The sector further comprises a plurality of switches of which two are illustrated in FIG. 23. Each switch 1420 in the plurality of switches gates the electrical signal between the drain 1418 of a corresponding nano-electronic measurement device 1414 in the plurality of nano-electronic measurement devices and the amplifier input line 1410 between (i) an on state, in which the electrical signal at the drain 1418 of the corresponding nano-electronic measurement device 1414 is delivered to the amplifier input line 1410, and (ii) an off state, in which the electrical signal at the drain 1418 of the corresponding nano-electronic measurement device 1414 is not delivered to the amplifier input line 1410.

The sector further comprises a second clock line 2202 and a row shift register 2220 comprising a first plurality of flip-flops, such as D flip-flops. The data input of an initial flip-flop 2222A in the first plurality of flip-flops is in electrical communication with the data input line 1404 and the clock pulse input of each flip-flop 2222 in the first plurality of flip-flops is in electrical communication with the first clock signal line 1402. The sector further comprises a plurality of AND gates. Each AND gate 2224 in the plurality of AND gates comprises a first input, a second input and an output. The sector further comprises a plurality of column shift registers. Each column shift register 2226 comprises a second plurality of flip-flops and, in optional embodiments, a third-plurality of flip-flops. The first input of each AND gate 2224 in the first plurality of AND gates is in electrical communication with an output of a corresponding flip-flop 2222 in the first plurality of flip-flops of the row shift register 2220. The second input of each AND gate 2224 in the first plurality of AND gates is in electrical communication with the second clock line 2202.

A clock pulse signal input of each respective column shift register 2226 in the plurality of column shift registers is in electrical communication with the output of a corresponding AND gate 2224 in the first plurality of AND gates. In other words, the output line 2204 of each AND gate 2224 serves as the clock input line of a corresponding shift register 2226 as illustrated in FIG. 22. Thus, line 2204 connects directly to the clock input of each flip-flip 1424 in a second plurality of flip-flops in the column shift register 2226 as illustrated in FIG. 23. The data input to the flip-flops in the second plurality of flip-flops in each column shift register 2226 starts as input 1426 of the initial flip-flop 1424-1-1 of the second plurality of flip-flops from the "restart scan chain" line 2206 and gets serially moved from the output 1428 of one flip-flop 1424 to the input 1426 of the next flip-flop 1424 of the column shift register 2226 as illustrated in more detail in FIG. 23.

The respective second plurality of flip-flops of each respective column shift register 2226 in the plurality of column shift registers comprises an initial flip-flop and a terminal flip-flop and any number of serially connected flip-flops between the initial flip-flop and the terminal flip-flop. FIG. 23 provides more details of a column shift register 2226. The column shift register 2226 of FIG. 23 has been rotated to appear as a row, instead of a column as it appears in FIG. 22, to better illustrate the features of the column shift register 2226. Each flip-flop 1424 in the respective second plurality of flip-flops of the column shift register 2226 includes a serial input 1426, a serial output 1428, and a clock pulse input (denoted as a triangle in each flip-flop). The serial output 1428 of each flip-flop 1424 in the respective second plurality of flip-flops, other than the terminal flip-flop, is uniquely electrically connected to the serial input 1426 of another flip-flop 1424 in the second plurality of flip-flops, thereby electrically coupling the respective second plurality of flip-flops in series. The serial data input 1426 of the initial flip-flop (illustrated as flip flop 1424-1-1 in FIG. 23) is electrically connected to the restart scan chain 2206. Thus, referring back to FIG. 22, the connection 2204 connects the output of an AND gate 2224A to the clock pulse input of each flip-flop 1424 in the second plurality of flip-flops and the restart scan 2206 is connected to the data input 1426 of the initial flip-flop 1424-1-1 of the second plurality of flip-flops of the column shift register 2226. The respective column shift register 2226 is configured to receive a device scan chain sequence, from the restart scan chain line 2206, that is propagated through the second plurality of flip-flops by electrical pulses in the second clock signal line 2202, as filtered by the plurality of AND gates 2224, thereby independently biasing each flip-flop 1424 in the second plurality of flip-flops to one of the first state and the second state.

Referring once again to FIG. 23, each flip-flop 2302 in the third plurality of flip-flops comprises an input (D), an output (Q) and a clock pulse input (denoted as a triangle in each flip-flop). The clock pulse input of each respective flip-flop 2302 in the third plurality of flip-flops is wired to the load buffer line 2208. The data input (D) of each respective flip-flop 2302 in the third plurality of flip-flops is wired to the output 1428 of a corresponding flip-flop 1424 in the second plurality of flip-flops. This causes the state of the corresponding flip-flop 2302 in the third plurality of flip-flops to be biased to the first state when the corresponding flip-flip 1424 in the second plurality of flip-flops is biased to the first state and the load buffer 2208 line is logically asserted, and the state of the corresponding flip-flop 2302 in the third plurality of flip-flops to be biased to the second state when the corresponding flip-flip 1424 in the second plurality of flip-flops is biased to the second state and the load buffer 2208 line is logically asserted. As illustrated in FIG. 23, each respective switch 1420 in the plurality of switches is independently wired to the output of a corresponding flip-flop 2302 in the third plurality of flip-flops of a corresponding column shift register 2226, thereby causing the respective switch to be in the off state when the corresponding flip-flop 2302 in the third plurality of flip-flops of the corresponding column shift register 2226 is biased to the first state, and be in the on state when the corresponding flip-flop 2302 in the third plurality of flip-flops of the corresponding column shift register is biased to the second state.

Thus, referring to FIG. 22, the horizontal shift register 2220 is loaded with data, a single bit for each column, and then N pulses are applied to the vertical shift clock 2202. By an appropriate choice of bits and choices of N, any number of shifts can be implemented independently on each column. For example, if a 4-bit shift integer is desired (meaning a minimum of 0 and a maximum of $2^4-1=15$ shifts down a particular column), first the "ones" place of each 4-bit number is loaded into the horizontal shift register 2220. That is, each flip-flop 2222 is biased to a first or second state to reflect the "ones" position of the four bit number, and N=1 pulses are applied to the vertical clock 2202. Where there is a "1" in the shift register, this pulse is communicated as clock pulses to the associated column shift register 2226. Where there is a "zero" in the horizontal shift register 2220, the vertical clock pulse 2202 is blocked by the logical "and" operation at the first AND 2224 that sits between the vertical clock input 2202 and the column shift register 2226. Then the "twos" place of each 4-bit number is loaded into the flip-flops of the horizontal shift register 2220, and N=4 pulses are applied to the vertical clock 2202. Then the "fours" place is loaded into the flip-flops of the horizontal shift register 2220 and N=8 pulses are applied to the vertical clock 2202. Finally, the "eights" place is loaded and N=16 pulses are applied. In this way each column shift register 2226 will receive a total number of pulses that is defined by the 4-bit number selected for each one column shift register 2226, causing a value "1" to be placed in exactly correct flip-flop in each column. In this way, a value of "1" can be placed five flip-flops down in one column shift register 2226 and 14 flip-flops down in another column shift register 2226 using the same number of pulses (cycles) on the vertical clock. When the cycle is complete and the logical "1" has left the bottom of the shift register, a new scan is initiated by setting the "restart scan" line 2206, which loads a new logical "1" into the vertical shift register upon the receipt of the next vertical pulse. FIG. 23 illustrates how the restart scan 2206 may be used to reset scan sequence loaded into the column shift register 2226.

In some embodiments, the horizontal shift register 2220 is buffered while it is being loaded so that the amplifier 1412 can be fruitfully used while the horizontal shifting takes place. In some embodiments, the full N-bit shift count is loaded into a register at the top of each column and the circuitry needed to count down on that number so that the fully set of pulses need not be interrupted by data shifting.

One advantage of the architecture disclosed in FIGS. 22 and 23 is that the hardware is agnostic as to the number of bits, or even whether the system would be used purely in base 2. For example, if there were three or four columns that needed exactly 17 vertical clock pulses, it is be possible to simply load a horizontal shift register with those columns set to "one" after the 15 pulses had already been applied on the vertical clock 2202, and then apply an additional N=2 pulses of the vertical clock 2202. This would not save on data input in this case, but it would reduce the total time, as an N=16 pulses event would not be necessary. It should also be noted that in this architecture, the number of bits could vary from move to move. A 4-bit string could be followed by a 3-bit and then a 7-bit. Each such bit number would address a different number of flip-flops in a column shift register 2226.

Another way of using the device illustrated in FIG. 22 is to send just a single "one" along the horizontal shift register 2220 and then apply exactly the number of vertical pulses 2202 that that the particular column needs. This could work if the integration time on each amplifier 1412 is sufficiently long to allow N columns×<N pulses> to be applied between each shift of each column.

Figure 24:
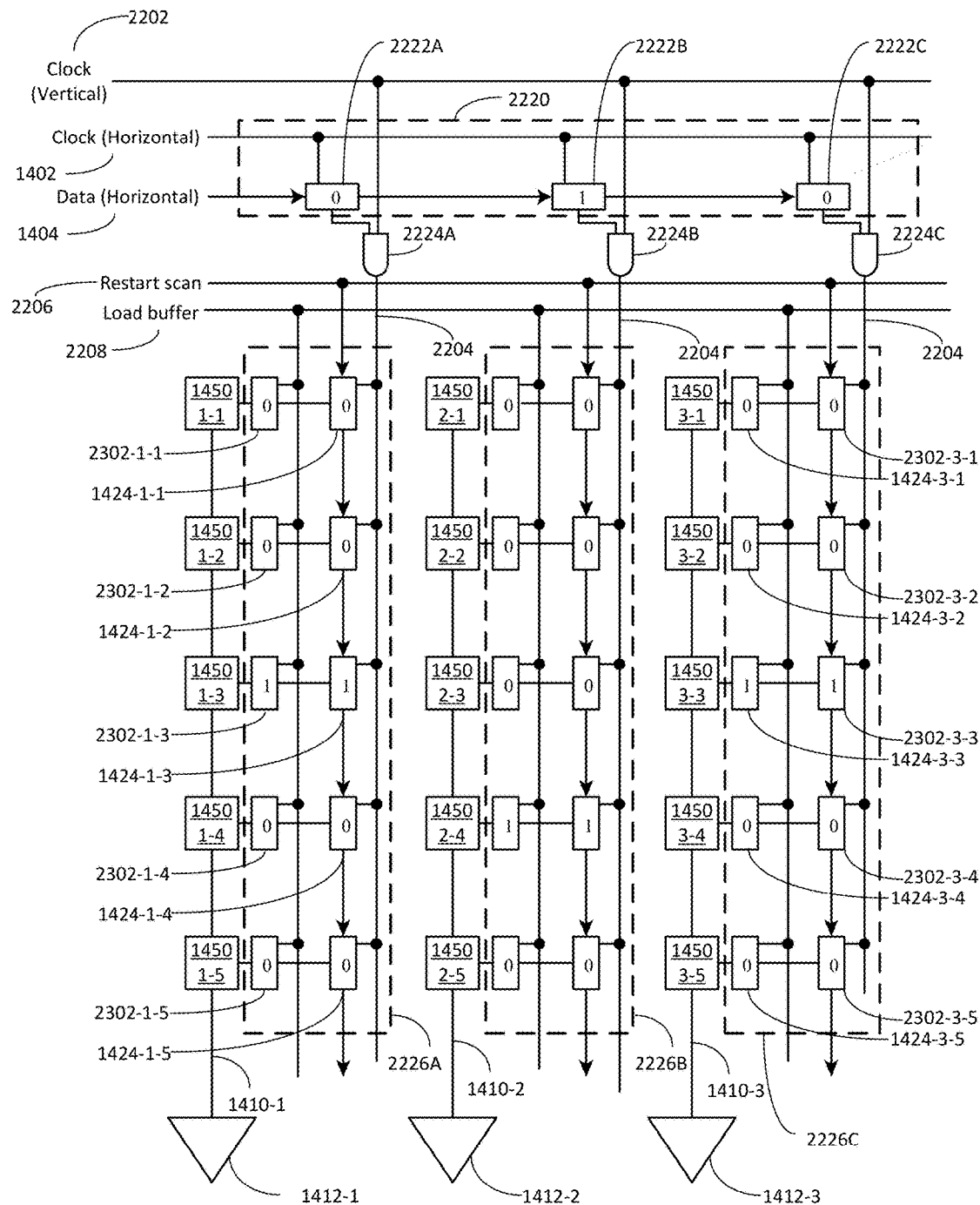
FIG. 24 illustrates the sparse amplifier array of FIG. 22 after a load signal has been asserted in accordance with an embodiment of the present disclosure.

In the embodiments illustrated, the third plurality of flip-flops 2302 is optional. For instance, as in other embodiments, the output of each flip-flop 1424 can be placed in direct electrical communication with a switch 1420. However, the use of the third plurality of flip-flops 2302 in each pixel 1450, in embodiments where this second memory element is present, controls which device 1414 is connected to an amplifier 1412 as illustrated in FIG. 23. The values of the third plurality of flip-flops only change when the "Load Buffer" signal is asserted on line 2208, which is performed after all the vertical shift register values are loaded into the second plurality of flip-flops 1424 of the column shift register 2226. Thus, for example, application of the "Load Buffer" signal on line 2208 of the embodiment illustrated in FIG. 22, results in the state illustrated in FIG. 24 where the state of each flip-flop 2302 in the third plurality of flip-flops matches the state of its corresponding second flip-flop 1424 in the second plurality of flip-flops. Then the load buffer signal is set de-asserted allowing for the horizontal shift register to reload the column shift registers 2226 while at the same time, one of the devices 1412 of a pixel 1450 is read out. This allows devices 1414 to be measured even while a new measurement configuration is being loaded into the column shift register 2226 by the vertical shift register 2220.

Figure 25:
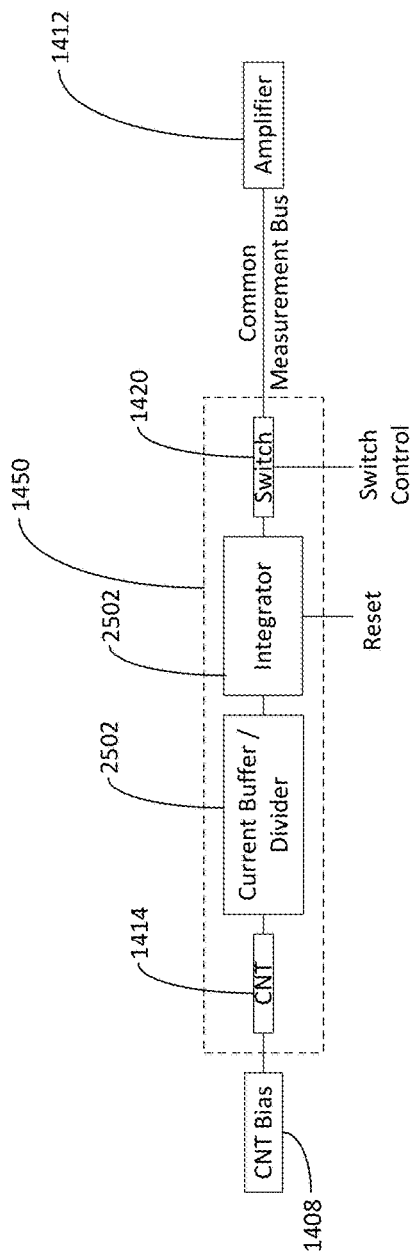
FIG. 25 illustrates a sparse amplifier array for nucleic acid sequencing in which a measurement device current is divided down within a pixel and the current value integrated, and when a switch is turned on, the amplifier amplifies the integrated voltage value, in accordance with an embodiment of the present disclosure.

FIG. 25 illustrates another sparse amplifier array in accordance with another aspect of the present disclosure. While nano-electronic measurement devices 1414 are often measured by clamping a voltage across them and measuring a current through a transimpedance amplifier, the alternative device illustrated in FIG. 25 takes a nano-electronic measurement device current 1414, divides it down within a pixel 1450 and integrates the current value. When the switch 1420 is turned on, the amplifier 1412 amplifies the integrated voltage value. The current divider 2502 has significance because the nano-electronic measurement device 1414 current values are fairly large, and the area for an integrator capacitor will be fairly limited, so by dividing the current value down we can ensure that the integrator 2504 doesn't saturate. This measurement scheme could be addressed with either the scan chain or row/column addressing methods described above.

The circuits for carrying out the logic of the sparse amplifier arrays of FIGS. 14 through 25 have been shown in detail, including the individual gates and their interconnnections. These diagrams were provided for demonstrating the logical construction of the particular sparse amplifier arrays. However, it will be appreciated that, in practice, the function may be obtained from programmable small-scale integration (SSI) devices, medium-scale integration (MSI) devices, large-scale integration (LSI) devices, or very-large scale integration (VLSI) devices where the programmer or system designer only accesses external inputs and outputs but not the inputs and outputs of intermediate gates in the device. For example, incorporation of a register into a sparse amplifier array is more likely done by selecting a suitable MSI circuit than designing the individual digital circuits that are shown in the figures of the present disclosure. As such, any such circuits that carry out the logic of the sparse amplifier arrays disclosed herein are within the scope of the present disclosure.

Common to all of the embodiments of the sparse amplifier arrays of FIGS. 14 through 25 is that they are pushing information into the amplifier array that relates to which nano-electronic measurement devices 1414 are working (e.g., are in a certain state such as an on state or an off state). Moreover, while the addressed measurement devices of these sparse amplifier arrays are each a nano-electronic measurement device 1414, the present disclosure is not so limited and is, in fact, agnostic to the type of measurement device used and the application of such measurement devices. That is, the sparse amplifier arrays of FIGS. 14 through 25 can be used for purposes other than nucleic acid sequencing. Additionally, the sparse amplifier arrays of FIGS. 14 through 25 can make use of measurement devices other than nano-electronic measurement device 1414 devices. That is, any form of arrayed measurement device in which many of the measurement devices are not functional is suitable for the architectures described in the present disclosure. Thus, in some embodiments, a light sensor or any other device that possibly has a high probability of not functioning may serve in the place of element 1414 in FIGS. 14 through 25. The following are some specific embodiments of such devices which make use of FIG. 14 through 25 with the exception that the nano-electronic measurement device 1414 has been substituted for a more general measurement device 2602.

In one aspect in accordance with such embodiments, an integrated circuit comprising a substrate is provided with a plurality of sectors arranged on the substrate (e.g., 10 or more sectors, 100 or more sectors, 1000 or more sectors), where each sector in the plurality of sectors comprises a first clock signal line 1402, a data input line 1404, a switch controller 1406 that is in electrical communication with the first clock signal line 1402 and the data input line 1404. Each sector in the plurality of sectors further comprises a counter bias line 1408 and an amplifier input line 1410. A plurality of measurement devices 2602 are spatially arranged on the substrate. Each respective measurement device 2602 in the plurality of measurement devices includes a source 1416 that is coupled to the counter bias line 1408 and a drain 1418 that is coupled to the amplifier input line 1410 thereby obtaining an electrical signal on the drain 1418 of the respective measurement device 2602. Each sector in the plurality of sectors further comprises a plurality of switches. Each switch 1420 in the plurality of switches gates the electrical signal between the drain 1418 of a corresponding measurement device 2602 in the plurality of measurement devices and the amplifier input line 1410 between (i) an on state, in which the electrical signal at the drain 1418 of the corresponding measurement device 2602 is delivered to the amplifier input line, and (ii) an off state, in which the electrical signal at the drain 1418 of the corresponding measurement device is not delivered to the amplifier input line 1410. Each respective switch 1420 in the plurality of switches is independently wired to the switch controller 1406 thereby causing the respective switch 1420 to be in one of the on state and the off state responsive to the switch controller 1406 as a function of a clock pulse on the first clock signal line 1402 and information received by the data input line 1404.

Referring to FIG. 15 with the exception that the nano-electronic measurement devices 1414 have been substituted for a more general measurement devices 2602, in some embodiments the switch controller of a sector in the plurality of sectors comprises a first shift register 1422 comprising a first plurality of flip-flops in electrical communication with the first clock signal line 1402. In such embodiments, the first plurality of flip-flops comprises an initial flip-flop 1424A and a terminal flip-flop 1424B, and any number of flip-flops between the initial and terminal flip-flop. Each flip-flop 1424 includes a serial input 1426 and a serial output 1428, where the serial output of each flip-flop in the first plurality of flip-flops, other than the terminal flip-flop, is uniquely electrically connected to the serial input of another flip-flop in the first plurality of flip-flops, thereby electrically coupling the first plurality of flip-flops in series. The serial input 1426 of the initial flip-flop 1424A is electrically connected to the data input line 1404. The first shift register 1422 is configured to receive a device scan chain sequence, from the data input line 1404, that is propagated through the first plurality of flip-flops by electrical pulses in the first clock signal line 1402 thereby independently biasing each flip-flop 1424 in the first plurality of flip-flops to one of a first state and a second state. Each respective switch 1420 in the plurality of switches is independently wired to the switch controller through a corresponding flip-flop 1424 in the first plurality of flip-flops thereby causing the respective switch to be in the off state when the corresponding flip-flop is biased to the first state and causing the respective switch to be in the on state when the corresponding flip-flop is biased to the second state.

Referring to FIGS. 16 and 17 with the exception that the nano-electronic measurement devices 1414 have been substituted for a more general measurement devices 2602, in some embodiments, the sector in the plurality of sectors further comprises a shunt scan chain input line 1506, and a shunt clock signal line 1550. The switch controller further comprises a second shift register comprising a second plurality of flip-flops in electrical communication with the shunt clock signal line 1506. Referring to FIG. 17, the second plurality of flip-flops comprises an initial flip-flop 1706A and a terminal flip flop 1706B, and any number of flip-flops between the initial flip-flop and the terminal flip-flop. Each flip-flop 1706 in the second plurality of flip-flops includes a serial input 1708 and a serial output 1710, where the serial output 1710 of each flip-flop 1706 in the second plurality of flip-flops, other than the terminal flip-flop, is uniquely electrically connected to the serial input 1708 of another flip-flop in the second plurality of flip-flops 1706, thereby electrically coupling the second plurality of flip-flops in series. The serial input 1708 of the initial flip-flop 1706A in the second plurality of flip-flops is electrically connected to the shunt scan chain input line 1702. The second shift register is configured to receive a shunt scan chain sequence that is propagated through the second plurality of flip-flops by electrical pulses in the shunt clock signal line 1702, thereby independently biasing each flip-flop 1706 in the second plurality of flip-flops to one of a third state and a forth state. In such embodiments, the switch controller further comprises a plurality of multiplexers, where each multiplexer 1712 in the plurality of multiplexers includes a first input line 1714, a second input line 17, a select line 1718, and an output line 1720. The first input line 1714 of each respective multiplexer 1712 in the plurality of multiplexers is in electrical communication with the serial output of a first corresponding flip-flop 1424 in the first plurality of flip-flops. The second input line 1716 of each respective multiplexer 1712 in the plurality of multiplexers is in electrical communication with the serial input of the first corresponding flip-flop 1424 in the first plurality of flip-flops. The select line 1718 of each respective multiplexer 1712 in the plurality of multiplexers is in electrical communication with the serial output 1710 of a first corresponding flip-flop 1706 in the second plurality of flip-flops. The output line 1720 of each respective multiplexer in the plurality of multiplexers is in electrical communication with the serial input of a second corresponding flip-flop 1424 in the first plurality of flip-flops. Each sector further comprises a first plurality of AND gates, where each AND gate 1722 in the first plurality of AND gates comprises an output 1724, a first input 1726 and a second input 1728. The first input 1726 of each respective AND gate 1722 in the first plurality of AND gates is in electrical communication with the first clock signal line 1402. The second input 1728 of each respective AND gate 1722 in the first plurality of AND gates is in electrical communication with the serial output 1710 of the first corresponding flip-flop 1706 in the second plurality of flip-flops. Each respective flip-flop 1424 in the first plurality of flip-flops is in electrical communication with the first clock signal line 1402 through the output 1724 of a corresponding AND gate 1722 in the first plurality of AND gates, so that, when a respective flip-flop 1706 in the second plurality of flip-flops, that is in electrical communication with the second input 1728 of the respective AND gate 1722, is in the third state, the first clock signal line 1402 is not applied to the respective flip-flop 1424 in the first plurality of flip-flops and the select line 1718 of the multiplexer 1712 in the plurality of multiplexers that is in electrical communication with the output 1710 of the respective flip-flop 1760 in the second plurality of flip-flops is biased to the second input line 1716 of the respective multiplexer 1712, and when the flip-flop 1706 in the second plurality of flip-flops, that is in electrical communication with the second input 1728 of the respective AND gate 1722, is in the fourth state, the first clock signal line 1402 is applied to the respective flip-flop 1424 in the first plurality of flip-flops and the select line 1718 of the multiplexer 1712 in the plurality of multiplexers that is in electrical communication with the output 1710 of the respective flip-flop 1706 in the second plurality of flip-flops is biased to the first input line 1714 of the respective multiplexer.

In some embodiments, the output line 1720 of each respective multiplexer 1712 in the plurality of multiplexers is in electrical communication with the serial input D of a second corresponding flip-flop 1424 in the first plurality of flip-flops through a corresponding buffer gate 1730 in a plurality of buffer gates.

Referring to FIG. 18 with the exception that the nanoelectronic measurement devices 1414 have been substituted for a more general measurement devices 2602, the architecture builds upon the scan chain architecture described above in conjunction with FIGS. 16 and 17 above. The sparse amplifier array further includes a shunt signal and asynchronous reset inputs to the flip flops. The shunt signal allows a pixel 1450 to be set to 'shunt' by asserting the asynchronous reset signal at the same time that a pixel is being measured. This feature allows pixels to be removed from the scan chain without having to reload the entire shunt scan chain.

Referring to FIG. 19 with the exception that the nanoelectronic measurement devices 1414 have been substituted for a more general measurement devices 2602, the sparse amplifier array of FIG. 18 is depicted in greater detail. Each flip-flop 1424 in the first plurality of flip-flops further comprises a first reset 1902. Each flip-flop 1706 in the second plurality of flip-flops further comprises a second reset 1904. Each sector of the sparse amplifier array further comprises a shunt signal line 1906. The switch controller 1422 further comprises a second plurality of AND gates. Each AND gate 1908 in the second plurality of AND gates has an output 1910, a first input 1912 and a second input 1914. The first input 1912 of each respective AND gate 1908 in the second plurality of AND gates is in electrical communication with the serial output Q of a first flip-flop 1424 in the first plurality of flip-flops. The second input 1914 of each respective AND gate 1908 in the second plurality of AND gates is in electrical communication with the shunt signal line 1906. The output 1910 of each respective AND gate 1908 in the second plurality of AND gates is in electrical communication with the first reset 1716 of the corresponding flip-flop 1424 in the first plurality of flip-flops and the second reset 1904 of a corresponding flip-flop 1706 in the second plurality of flip-flops, thereby causing the first corresponding flip-flop 1424 to reset to the first state and the second corresponding flip-flop 1706 to reset to the third state when the shunt signal line 1906 is asserted at the same time that the measurement device 2602 in electrical communication with the first corresponding flip-flop 1424 is driven 1408 by the data input line 1404 to the second state. Thus, in a given pixel 1450, when the flip-flop 1424 is in the second state, meaning that the corresponding switch 1420 is closed (in the on state) and the measurement device 2602 is being measured by the amplifier 1412, a signal on the shunt signal line 1906 will pass through the AND gate 1908 and reset the flip-flop 1424 to the first state, thereby opening the switch 1420 (setting the switch to the off states) and resetting the flip-flop 1706 to the third state thereby causing the scan chain on the data input line 1404 to permanently bypass the pixel 1450.

Referring to FIG. 20 with the exception that the nanoelectronic measurement devices 1414 have been substituted for more general measurement devices 2602, a particular embodiment of the sparse amplifier array is illustrated in accordance with another aspect of the present disclosure. The sparse amplifier array of FIG. 20 comprises one hundred or more such sectors, one thousand or more such sectors, one hundred thousand or more such sectors, or a million or more such sectors on a single chip, and FIG. 20 illustrates one such sector. Each sector of the sparse amplifier array of FIG. 20 has a memory bank 2002 that can store the address of N functional measurement devices 2602 within the sector. Two decoders, a row decoder 2004 and a column decoder 2006, with inputs stored in the memory bank 2002, are used to select a measurement device 2602. In particular, in some embodiments, the memory bank 2002 stores a single bit for each pixel 1450, where one value of the pixel indicates that the corresponding pixel is to read and the other value of the pixel indicates that the corresponding pixel is not to be read. The decoders are used to select the row and column of a measurement device 2602 that is to be read, routing the output of one such device 2602 (e.g., the current across the channel of the device) to an amplifier 1412. This architecture allows direct addressing of any pixel 1450 in the array, where each such pixel includes a measurement device 2602, and pixels can be selected in any order, and any number of pixels can be permanently sealed from reading because their measurement devices 2602 are not functional. The size N of the memory bank 2002 is designed by estimating the number of anticipated functional devices 1414 in the sector.

Referring to FIGS. 20 and 21, with the exception that the nano-electronic measurement devices 1414 have been substituted for more general measurement devices 2602, the depicted embodiment of the sparse amplifier array includes a plurality of sectors of which one is shown. Each sector is associated with an amplifier 1412 and includes a switch controller comprising a memory 2002 in electrical communication with the memory controller 2008, a column decoder 2006 in electrical communication with the memory 2002, and a row decoder 2004 in electrical communication with the memory 2002. Referring to FIG. 21, with the exception that the nano-electronic measurement devices 1414 have been substituted for more general measurement devices 2602, the sector further comprises a plurality of AND gates. Each AND gate 2102 in the plurality of AND gates comprises an output 2004, a first input 2006 and a second input 2008. The first input 2006 of each respective AND gate 210 in the plurality of AND gates is in electrical communication with the column decoder 2006. The second input 2008 of each respective AND gate 2102 in the plurality of AND gates is in electrical communication with the row decoder 2004. Each respective switch 1420 in the plurality of switches is independently wired to the switch controller through the output 2004 of a corresponding AND gate 2102 in the plurality of AND gates, thereby causing the respective switch 1420 to be in the on state when the row decoder 2004 and the column decoder 2006 both signal a first state to the corresponding AND gate 2102 and otherwise causing the respective switch 1420 to be in the off state.

Referring to FIG. 22 with the exception that the nano-electronic measurement devices 1414 have been substituted for more general measurement devices 2602, what is illustrated is a particular embodiment of a sparse amplifier array in accordance with another aspect of the present disclosure. FIG. 23 illustrates a more detailed embodiment of the sparse amplifier array of FIG. 22. The integrated circuit comprises a substrate (not shown in FIG. 22) and a plurality of sectors arranged on the substrate. FIG. 22 illustrates one such sector of the sparse amplifier array. In some embodiments the sparse amplifier array comprises one hundred or more such sectors, one thousand or more such sectors, one hundred thousand or more such sectors, or a million or more such sectors on a single chip. In FIG. 22, each sector in the plurality of sectors comprises a first clock signal line 1402 and a data input line 1404. The sector further comprises a counter bias line 1408 (not shown in FIG. 22, but shown in FIG. 23) and an amplifier input line 1410, also referred to as a common measurement bus line. Each amplifier input line 1410 is in electrical communication with a corresponding amplifier 1412. In some embodiments, the corresponding amplifier 1412 is not on the chip. In some embodiments, the corresponding amplifier 1412 is on the chip. Referring to FIG. 23, the sector further comprises a plurality of measurement devices 2602 spatially arranged on the substrate in pixels 1450. As shown in more detail in FIG. 23, with the exception that the nano-electronic measurement devices 1414 have been substituted for more general measurement devices 2602, each respective measurement device 2602 in the plurality of measurement devices includes a source 1416 that is coupled to the counter bias line 1408 and a drain 1418 that is coupled to the amplifier input line 1410 thereby obtaining an electrical signal on the drain 1418 of the respective measurement device 2602. The sector further comprises a plurality of switches of which two are illustrated in FIG. 23. Each switch 1420 in the plurality of switches gate the electrical signal between the drain 1418 of a corresponding measurement device 2602 in the plurality of measurement devices 2602 and the amplifier input line 1410 between (i) an on state, in which the electrical signal at the drain 1418 of the corresponding measurement device 2602 is delivered to the amplifier input line 1410, and (ii) an off state, in which the electrical signal at the drain 1418 of the corresponding measurement device 2602 is not delivered to the amplifier input line 1410.

The sector further comprises a second clock line 2202 and a row shift register 2220 comprising a first plurality of flip-flops, such as D flip-flops. The data input of an initial flip-flop 2222A in the first plurality of flip-flops is in electrical communication with the data input line 1404 and the clock pulse input of each flip-flop 2222 in the first plurality of flip-flops is in electrical communication with the first clock signal line 1402. The sector further comprises a plurality of AND gates. Each AND gate 2224 in the plurality of AND gates comprises a first input, a second input and an output. The sector further comprises a plurality of column shift registers. Each column shift register 2226 comprises a second plurality of flip-flops and, in optional embodiments, a third-plurality of flip-flops. The first input of each AND gate 2224 in the first plurality of AND gates is in electrical communication with an output of a corresponding flip-flop 2222 in the first plurality of flip-flops of the row shift register 2220. The second input of each AND gate 2224 in the first plurality of AND gates is in electrical communication with the second clock line 2202.

A clock pulse signal input of each respective column shift register 2226 in the plurality of column shift registers is in electrical communication with the output of a corresponding AND gate 2224 in the first plurality of AND gates. In other words, the output line 2204 of each AND gate 2224 serves as the clock input line of a corresponding shift register 2226 as illustrated in FIG. 22. Thus, line 2204 connects directly to the clock input of each flip-flip 1424 in a second plurality of flip-flops in the column shift register 2226 as illustrated in FIG. 23. The data input to the flip-flops in the second plurality of flip-flops in each column shift register 2226 starts as input 1426 of the initial flip-flop 1424-1-1 of the second plurality of flip-flops from the "restart scan chain" line 2206 and gets serially moved from the output 1428 of one flip-flop 1424 to the input 1426 of the next flip-flop 1424 of the column shift register 2226 as illustrated in more detail in FIG. 23.

The respective second plurality of flip-flops of each respective column shift register 2226 in the plurality of column shift registers comprises an initial flip-flop and a terminal flip-flop and any number of serially connected flip-flops between the initial flip-flop and the terminal flip-flop. FIG. 23 provides more details of a column shift register 2226 with the exception that the nano-electronic measurement devices 1414 have been substituted for more general measurement devices 2602. The column shift register 2226 of FIG. 23 has been rotated to appear as a row, instead of a column as it appears in FIG. 22, to better illustrate the features of the column shift register 2226. Each flip-flop 1424 in the respective second plurality of flip-flops of the column shift register 2226 includes a serial input 1426, a serial output 1428 and a clock pulse input (denoted as a triangle in each flip-flop). The serial output 1428 of each flip-flop 1424 in the respective second plurality of flip-flops, other than the terminal flip-flop, is uniquely electrically connected to the serial input 1426 of another flip-flop 1424 in the second plurality of flip-flops, thereby electrically coupling the respective second plurality of flip-flops in series. The serial data input 1426 of the initial flip-flop (illustrated as flip flop 1424-1-1 in FIG. 23) is electrically connected to the restart scan chain 2206. Thus, referring back to FIG. 22, the connection 2204 connects the output of an AND gate 2224A to the clock pulse input of each flip-flop 1424 in the the second plurality of flip-flops and the restart scan line 2206 is connected to the data input 1426 of the initial flip-flop 142-4-1-1 of the second plurality of flip-flops. The respective column shift register 2226 is configured to receive a device scan chain sequence, from the restart scan chain 2206 line, that is propagated through the second plurality of flip-flops by electrical pulses in the second clock signal line 2202, as filtered by the plurality of AND gates 2224, thereby independently biasing each flip-flop 1424 in the second plurality of flip-flops to one of the first state and the second state.

Referring once again to FIG. 23, with the exception that the nano-electronic measurement devices 1414 have been substituted for more general measurement devices 2602, each flip-flop in the third plurality of flip-flops comprises an input (D), an output (Q) and a clock pulse input (denoted as a triangle in each flip-flop). The clock pulse input of each respective flip-flop 2302 in the third plurality of flip-flops is wired to the load buffer line 2208. The data input (D) of each respective flip-flop 2302 in the third plurality of flip-flops is wired to the output 1428 of a corresponding flip-flop 1424 in the second plurality of flip-flops. This causes the state of the corresponding flip-flop 2302 in the third plurality of flip-flops to be biased to the first state when the corresponding flip-flip 1424 in the second plurality of flip-flops is biased to the first state and the load buffer 2208 line is logically asserted, and the state of the corresponding flip-flop 2302 in the third plurality of flip-flops to be biased to the second state when the corresponding flip-flip 1424 in the second plurality of flip-flops is biased to the second state and the load buffer 2208 line is logically asserted. As illustrated in FIG. 23, each respective switch 1420 in the plurality of switches is independently wired to the output of a corresponding flip-flop 2302 in the third plurality of flip-flops of a corresponding column shift register 2226, thereby causing the respective switch to be in the off state when the corresponding flip-flop 2302 in the third plurality of flip-flops of the corresponding column shift register 2226 is biased to the first state, and be in the on state when the corresponding flip-flop 2302 in the third plurality of flip-flops of the corresponding column shift register is biased to the second state.

Thus, referring to FIG. 22, with the exception that the nano-electronic measurement devices 1414 have been substituted for more general measurement devices 2602, the horizontal shift register 2220 is loaded with data, a single bit for each column, and then N pulses are applied to the vertical shift clock 2202. By an appropriate choice of bits and choices of N, any number of shifts can be implemented independently on each column. For example, if a 4-bit shift integer is desired (meaning a minimum of 0 and a maximum of $2^4-1=15$ shifts down a particular column), first the "ones" place of each 4-bit number is loaded into the horizontal shift register 2220. That is, each flip-flop is biased to a first or second state to reflect the "ones" position of the four bit number, and N=1 pulses are applied to the vertical clock 2202. Where there is a "1" in the shift register, this pulse is communicated to the associated column shift register 2226. Where there is a "zero" in the horizontal shift register 2220, the vertical clock pulse 2202 is blocked by the logical "and" operation at the first AND 2224 that sits between the vertical clock input 2202 and the column shift register 2226. Then the "twos" place of each 4-bit number is loaded into the flip-flops of the horizontal shift register 2220, and N=4 pulses are applied to the vertical clock 2202. Then the "fours" place is loaded into the flip-flops of the horizontal shift register 2220 and N=8 pulses are applied to the vertical clock 2202. Finally, the "eights" place is loaded and N=16 pulses are applied. In this way each column shift register 2226 will receive a total number of pulses that is defined by the 4-bit number selected for each one column shift register 2226, causing a value "1" to be placed in exactly correct flip-flop in each column. In this way, a value of "1" can be placed five flip-flops down in one column shift register 2226 and 14 flip-flops down in another column shift register 2226 using the same number of pulses (cycles) on the vertical clock. When the cycle is complete and the logical "1" has left the bottom of the shift register, a new scan is initiated by setting the "restart scan" line 2206, which loads a new logical "1" into the vertical shift register upon the receipt of the next vertical pulse. FIG. 23 illustrates how the restart scan 2206 may be used to reset the column shift register 2226.

In some embodiments, the horizontal shift register 2220 is buffered while it is being loaded so that the amplifier 1412 can be fruitfully used to measure a measurement device 2602 while the horizontal shifting takes place. In some embodiments, the full N-bit shift count is loaded into a register at the top of each column and the circuitry needed to count down on that number so that the fully set of pulses need not be interrupted by data shifting.

One advantage of the architecture disclosed in FIGS. 22 and 23 is that the hardware is agnostic as to the number of bits, or even whether the system would be used purely in base 2. For example, if there were three or four columns that needed exactly 17 vertical clock pulses, it is be possible to simply load a horizontal shift register with those columns set to "one" after the 15 pulses had already been applied on the vertical clock 2202, and then apply an additional N=2 pulses of the vertical clock 2202. This would not save on data input in this case, but it would reduce the total time, as an N=16 pulses event would not be necessary. It should also be noted that in this architecture, the number of bits could vary from move to move. A 4-bit string could be followed by a 3-bit and then a 7-bit. Each such bit number would address a different number of flip-flops in a column shift register 2226.

Another way of using the device illustrated in FIG. 22 is to send just a single "one" along the horizontal shift register 2220 and then apply exactly the number of vertical pulses 2202 that that the particular column needs. This could work if the integration time on each amplifier 1412 is sufficiently long to allow N columns×<N pulses> to be applied between each shift of each column.

In the embodiments illustrated, the third plurality of flip-flops 2302 and the second plurality of AND gates 2302 is optional. For instance, as in other embodiments, the output of each flip-flop 1424 can be placed in direct electrical communication with a switch 1420. However, the use of this second memory element in each pixel 1450, in embodiments where this second memory element is present, controls which device 1414 is connect to an amplifier 1412 as illustrated in FIG. 23. The values of the third plurality of flip-flops only change when the "Load Buffer" signal is asserted on line 2208, which is performed after all the vertical shift register values are loaded into the second flip flops 1424 of the column shift register 2226. Thus, for example, application of the "Load Buffer" signal on line 2208 of the embodiment illustrated in FIG. 22, results in the state illustrated in FIG. 24 where the state of each third flip-flop 2302 matches the state of its corresponding second flip flop 1424. Then the load buffer signal is set de-asserted allowing for the horizontal shift register to reload the column shift registers 2226 while at the same time, one of the devices 1412 of a pixel 1450 is read out. This allows devices 1414 to be measured even while a new measurement configuration is being loaded into the column shift register 2226 by the vertical shift register 2220.

Referring to FIG. 25 with the exception that the nano-electronic measurement devices 1414 have been substituted for more general measurement devices 2602, another sparse amplifier array in accordance with another aspect of the present disclosure is disclosed. While measurement devices 2602 are often measured by clamping a voltage across them and measuring a current through a transimpedance amplifier, the alternative device illustrated in FIG. 25 takes a measurement device 2602 current, divides it down within a pixel 1450 and integrates the current value. When the switch 1420 is turned on, the amplifier 1412 amplifies the integrated voltage value. The current divider 2502 has significance because the measurement device 2602 current values can be fairly large for some forms of measurement devices, and the area for an integrator capacitor will be fairly limited, so by dividing the current value down we can ensure that the integrator 2504 doesn't saturate. This measurement scheme could be addressed with either the scan chain or row/column addressing methods described above.

In some embodiments, a measurement device in the plurality of nano-electronic measurement devices is a nanoFET that comprises the source, the drain, a gate, and a channel and wherein the input from the counter bias line is applied from the source to the drain across the channel. In some such embodiments, the channel is a nanowire, a carbon nanotube, or a graphene nanoribbon. In some embodiments, the counter bias line carries a DC voltage and the application of the counter bias line to the measurement device results in a DC current in the channel measurement device. In some embodiments, the counter bias line carries an AC voltage and a frequency of the AC voltage is changed with time during application of the counter bias line to the measurement device.

In some embodiments, each measurement device 2602 in the plurality of measurement devices is a light sensor.

In some embodiments, the measurement devices 2602 in a plurality of measurement devices of a sector in the plurality of sectors are arranged as a row or a column on the substrate. In some embodiments, the measurement devices 2602 in a plurality of measurement devices of a sector in the plurality of sectors are arranged as a plurality of rows or a plurality of columns on the substrate. Some embodiments provide any of the integrated circuits disclosed herein, and further comprise a plurality of amplifiers, where each amplifier in the plurality of amplifiers is in electrical communication with the amplifier input line of a corresponding sector in the plurality of sectors. In some such embodiments, an amplifier in the plurality of amplifiers is a current-to-voltage amplifier.

In some embodiments, the plurality of measurement devices 2602 in a sector in the plurality of sectors comprises 1,000 measurement devices. In some embodiments, the integrated circuit chip comprises 10,000 measurement devices 2602 arranged in the plurality of sectors. In some embodiments, the chip consists of between 1,000 measurement devices 2602 and 10 million measurement devices 2602 arranged in the plurality of sectors. In some embodiments, the chip consists of between 10,000 measurement devices 2602 and 1 million measurement devices 2602 arranged in the plurality of sectors.

In some embodiments, only a single respective measurement device 2602 in the plurality of measurement devices is in the on state in each sector in the plurality of sectors at a given point in time and the plurality of measurement devices of a sector in the plurality of sectors comprises three hundred devices.

In some embodiments, the data input line is configured to receive instructions that permanently by-pass more than fifty percent of the measurement devices 2602 in the plurality of measurement devices in a sector in the plurality of sectors.

In some embodiments, the plurality of sectors comprises ten or more sectors and the plurality of measurement devices 2602 in each sector in the plurality of sectors comprises one hundred devices. In some embodiments, the integrated circuit is configured to receive signals on the data input line that permanently bypass five percent, ten percent, fifteen percent, twenty percent, twenty-five percent, thirty-percent, thirty-five percent, fifty percent, or sixty percent or more of the measurement devices 2602 in a sector in the plurality of sectors thereby permanently causing bypassed measurement devices 2602 to be in the off state.

In some embodiments, the integrated circuit is configured to receive signals on the data input line that permanently bypass eighty percent or more of the measurement devices 2602 in a sector in the plurality of sectors thereby permanently causing bypassed measurement devices to be in the off state.

In some embodiments, the plurality of sectors comprises one hundred or more sectors and the plurality of measurement devices 2602 in each sector in the plurality of sectors comprises one thousand devices.

In some embodiments, the plurality of sectors comprises one hundred or more sectors and the plurality of measurement devices 2602 in each sector in the plurality of sectors comprises one thousand devices, and a single measurement device 2602 in two or more of the sectors in the plurality of sectors is in the off state where all other measurement devices 2602 in the two or more sectors are in the off state.

As discussed above, common to all of the embodiments of the sparse amplifier arrays of FIGS. 14 through 25 is that they are pushing information into the amplifier array that relates to which measurement devices 1414 are working (e.g., are in a certain state such as an on state or an off state). Moreover, in each of the embodiments illustrates, the switch is interrupts the electrical signal of a measurement device between the drain of the measurement device and the amplifier output line. Again, the present disclosure is not so limited and is, in fact, agnostic to what component (e.g., gate) of the measurement device the switch interacts with so long as one state of the switch prevents a measurement signal associated with the measurement device from reaching the amplifier output line. This can be achieved by using the switch to prevent the measurement device from generating a measurement signal altogether or by isolating the measurement signal from the amplifier output line. Moreover, there is no requirement that the amplifier output line be routed to an amplifier, and so in some embodiments, the amplifier output line is termed a "sector output line." Moreover, still, while a use case scenario in which a single measurement device in any given sector is producing a measurement signal that is reported to the amplifier output line at any given time, the present disclosure is not so limited. Specifically, more generally, at any given time less than the full plurality of measurement devices in a given sector are reporting measurement signals to the amplifier output line at any given time. Thus, methods, in which different patterns of measurement devices report out to the amplifier output line at any given time (are allowed to be in the on state) and such output is then deconvoluted, are expressly encompassed by the present disclosure.

With the above in mind, some specific embodiments of how a switch is used to prevent a measurement signal associated with a measurement device from reaching a sector output line will now be described. As such, it will be appreciated that the sparse amplifier arrays of any FIGS. 14 through 25 can easily be modified to change the interaction of the switch 1420 with the measurement device 1416 accordingly.

One such aspect of the present disclosure is an integrated circuit comprising a substrate and a plurality of sectors arranged on the substrate. Each sector in the plurality of sectors comprises a programmable switch controller, a sector input line, and a sector output line. Referring to FIG. 14A, a nonlimiting example of a sector input line is line 1408 and a nonlimiting examplle of a sector output line is line 1410. Each sector comprises a plurality of measurement devices spatially arranged on the substrate. Each respective measurement device in the plurality of measurement devices is electrically coupled to the sector input line and to the sector output line. Each sector further comprises a plurality of switches. Each respective switch in the plurality of switches gates a corresponding measurement device in the plurality of measurement devices between (i) an on state, in which an electrical measurement signal of the corresponding measurement device is delivered to the sector output line, and (ii) an off state, in which the electrical measurement signal of the corresponding measurement device is not delivered to the sector output line. In such embodiments, each respective switch in the plurality of switches is independently wired to the programmable switch controller thereby causing the respective switch to be in one of the on state and the off state responsive to the programmable switch controller and wherein the plurality of switches is configured to cause a subset of the measurement devices in the plurality of measurement devices to be in the on state at any given time.

In some embodiments in accordance with this aspect of the present disclosure, the subset of the measurement devices is a single measurement device, meaning that only one measurement device in the plurality of measurement devices of a sector is configured to be in the on state at any given time. In other embodiments, the subset of the measurement devices is two measurement devices, three or more device, four or more device or N or more devices, provided that N is less than the total number of devices in the sector.

In some embodiments in accordance with this aspect of the present disclosure, each respective measurement device in the plurality of measurement devices comprises a source, a drain, and a gate. An example of such embodiments is where the measurement device is a nanoFET. In such embodiments, the respective sector further comprises a gate line. Further, the sector input line is connected to the source of each respective measurement device in the plurality of measurement devices and the sector output line is connected to the drain of each respective measurement device in the plurality of measurement devices. Each respective switch in the plurality of switches gates the gate line to the gate of the corresponding measurement device in the plurality of measurement devices. In other words, when the switch is in the off state, the gate line is not connected to the gate of the corresponding measurement device and thus the corresponding measurement device does not deliver a measurement signal to the sector output line. When the switch is in the on state, the gate line is connected to the gate of the corresponding measurement device, and thus the corresponding measurement device delivers a measurement signal to the sector output line.

In some alternative embodiments in accordance with this aspect of the present disclosure, each respective measurement device in the plurality of measurement devices comprises a source and a drain. The sector input line is connected to the source of each respective measurement device in the plurality of measurement devices and the sector output line is connected to the drain of each respective measurement device in the plurality of measurement devices. The measurement device may have any number of additional inputs, such as a gate. Regardless of the measurement device type, in such embodiments, each respective switch in the plurality of switches gates the sector input line to the source of the corresponding measurement device in the plurality of measurement devices. In other words, when the switch is in the off state, the sector input line is not connected to the source of the corresponding measurement device and thus the corresponding measurement device does not deliver a measurement signal to the sector output line. When the switch is in the on state, the sector input line is connected to the source of the corresponding measurement device, and thus the corresponding measurement device delivers a measurement signal to the sector output line.

In still alternative embodiments in accordance with this aspect of the present disclosure, each respective measurement device in the plurality of measurement devices comprises a source and a drain. The sector input line is connected to the source of each respective measurement device in the plurality of measurement devices and the sector output line is connected to the drain of each respective measurement device in the plurality of measurement devices. The measurement device may have any number of additional inputs, such as a gate. Regardless of the measurement device type, in such embodiments, each respective switch in the plurality of switches gates the sector output line to the drain of the corresponding measurement device in the plurality of measurement devices. This embodiment is expressly illustrated in FIGS. 14 through 25.

In some aspects, the sparse amplifier comprises a chip that is able to concurrently read out from multiple sectors of the chip independently at the same time. In some embodiments the invention comprises an imaging chip such as a CMOS chip where each sector of the imaging chip has a separate shift register. The following describes a non-limiting embodiment to illustrate this aspect of the invention. The sparse amplifier can have e.g. 2000 columns×2000 rows or 3600 columns×3600 rows. As described above, only a fraction of the nano-electronic measurement devices 1414 will be productive devices. Here, the productive device fraction is around 1.5% (due to various stages of yield and Poisson loading losses described above). There is an amplifier 1412 associated with each row in some embodiments, so in the second example, there are 3600 amplifiers. Instead of the typical row/column addressing that is used in CMOS imagers, here, there is a separate shift register for each row, or 3600 separate shift registers running alongside the switching transistors that are used to "electrify" the nanoFET devices when they are to be probed.

A key difference between this embodiment of the sparse chip and a conventional chip is that this chip is capable of concurrently reading out from the chip sequencing data from a polymerase, for example, in column 1, row 16; and column 2, row 8; and column 3, row 22. In order to accomplish this, shift registers are provided for each row, allowing us to read independently from these different rows at the same time.

The operation of the shift register is illustrated by the following example. At the start of one "frame" of data collection (which would happen, for example, 1000 times per second), a "1" would be loaded in the first slot of every shift register and the rest of the values set to zero. Then a series of integers would be loaded into 3600 registers at the base of each column. The shift registers would then be pulsed N times if the integer is N . . . . So, when the column receives a "15" it pulses its shift register 15 times. This has the effect of moving the "1" up to the $16^{th}$ row where it stops. Now the switches are driven from the value in shift register; so where it is a "0" then the switch remains off, and where it is a "1" then it links it with the amplifier. For this example we count on reading from the 50 best nano-electronic measurement devices in each row, so after 25 microseconds another integer is loaded, and the shift register is again pulsed N times followed by the acquisition of 25 microseconds more data. In implementing this approach, the number of bits used to represent the number is chosen to balance the requirements of the system. For example, more bits will result in more data that needs to be processed, but could provide more precision. In some cases, the system is designed such that some precision is lost at the benefit of easier data handling. For example, in the description above the device would bump each column about 50 times for each "frame" generating a significant amount of data.

In some aspects, the invention provides a system for sequencing template nucleic acids that has a housing with housing electrical connection sites. The housing electrical connection sites are made to connect with electrical connections on the chip for providing electrical signals to the chip and for receiving electrical signals from the chip. There is a chip that reversibly mates with the housing. The chip is a nano-electronic measurement device chip as described herein. The system includes an electronic control system electrically connected to the nano-electronic measurement devices through the electrical connections to apply desired electrical signals to the nano-electronic measurement devices and for receiving electrical signals from the nano-electronic measurement devices. The system typically has a computer that receives information on the electrical signals at the nano-electronic measurement devices over time and uses such information to identify a sequence of the template nucleic acid. The computer can also control the performance of the chip, for example, by providing a sequence of electrical signals to the nano-electronic measurement devices on the chip.

Nucleotide analogs comprising charge labels will typically be larger, i.e. have a larger molecular weight than natural nucleotides. These analogs can include, for example, nucleotide analogs describe in U.S. Pat. No. 9,062,091 entitled Polymerase Enzyme Substrates with Protein Shield, and in U.S. patent application Ser. No. 14/452,497, entitled Protected Fluorescent Reagent Compounds, filed Aug. 5, 2014 which are incorporated herein by reference for all purposes.

In some cases the charge labels comprise beads, for example beads comprising multiple nucleotides attached via their polyphosphate portion. Such analogs are described, for example in U.S. Pat. No. 8,367,813 which is incorporated by reference herein in its entirety for all purposes. The beads can be coated with charged functional groups, anionic, cationic, or a combination of anionic and cationic groups. The amount of charge on the bead can be controlled in order to control the electrical signal at the gate of the nanoFET. The beads can have any usable size range, for example, between about 2 nm and about 50 nm in size. The shapes of the beads can be spherical, elongated, or other effective shape for controlling the current at the gate of the nanoFET.

Methods for making and addressing nano-electronic measurement devices including nanoFETs comprising nanowires are known in the art. See, for example, Choi et al. "Single-Molecule Lysozyme Dynamics Monitored by an Electronic Circuit" Science 335, 319 (2012), and Patolsky et al., "Electrical Detection of Viruses," PNAS, 101(39), 14017, 2004 which are incorporated herein by reference in their entirety for all purposes.

While the labels that interact with the channel are referred to as charge labels, the measured signal can be from a change in any suitable electrical property of the nanoscale wire, such as voltage, current, conductivity, resistivity, inductance, impedance, electrical change, an electromagnetic change, etc. The signal may further include various aspects of the kinetics of the reaction, e.g., on/off rates, incorporation rates, and rates of conformational changes in the enzyme. Yet further, the kinetics can be influenced experimentally to enhance kinetic signals, e.g., by changing the ionic strength or types of ions present in the reaction mixture or the concentrations of various components, e.g., nucleotides, salts, etc., or the types/lengths of the linkers attaching the labels to the nucleotide analogs, where those changes impact the kinetics of the reaction. In yet further embodiments, enzymes can be used that have more distinct, and therefore more detectable, conformational changes. These and other methods of changing the kinetics of a reaction that can be used with the methods described herein are further described in the art, e.g., in U.S. Pat. No. 8,133,672, U.S. Pat. No. 8,986,930, U.S. Pat. No. 8,999,676, and U.S. Pat. No. 9,279,155, all of which are incorporated herein by reference in their entireties.

Thus, the polymerase complex may be positioned relative to the nanoscale wire to cause a detectable change in the nanoscale wire. In some cases, the polymerase complex may be positioned within about 100 nm of the nanoscale wire, within about 75 nm of the nanoscale wire, within about 50 nm of the nanoscale wire, within about 20 nm of the nanoscale wire, within about 15 nm of the nanoscale wire, or within about 10 nm of the nanoscale wire. The actual proximity can be determined by those of ordinary skill in the art. In some cases, the polymerase complex is positioned less than about 5 nm from the nanoscale wire. In other cases, the polymerase complex is positioned within about 4 nm, within about 3 nm, within about 2 nm, or within about 1 nm of the nanoscale wire.

In some embodiments, the polymerase complex is fastened to or directly bonded (e.g., covalently) to the nanowire (nanoscale wire) or channel, e.g., as further described herein. However, in other embodiments, the polymerase complex is not directly bonded to the nanoscale wire, but is otherwise immobilized relative to the nanowire, i.e., the polymerase complex is indirectly immobilized relative to the nanowire. For instance, the polymerase complex may be attached to the nanowire through a linker, i.e., a species (or plurality of species) to which the polymerase complex and the nanoscale wire are each immobilized relative thereto, e.g., covalently or non-covalently bound to. As an example, a linker may be directly bonded to the nanoscale wire, and the polymerase complex may be directly bonded to the linker, or the polymerase complex may not be directly bonded to the linker, but immobilized relative to the linker, e.g., through the use of non-covalent bonds such as hydrogen bonding (e.g., as in complementary nucleic acid-nucleic acid interactions), hydrophobic interactions (e.g., between hydrocarbon chains), entropic interactions, or the like. The linker may or may not be directly bonded (e.g., covalently) to the nanoscale wire.

Many nanowires as used in accordance with the present invention are individual nanowires. As used herein, "individual nanowire" means a nanowire free of contact with another nanowire (but not excluding contact of a type that may be desired between individual nanowires, e.g., as in a crossbar array). For example, an "individual" or a "free-standing" article may, at some point in its life, not be attached to another article, for example, with another nanowire, or the free-standing article may be in solution. An "individual" or a "free-standing" article is one that can be (but need not be) removed from the location where it is made, as an individual article, and transported to a different location and combined with different components to make a functional device such as those described herein and those that would be contemplated by those of ordinary skill in the art upon reading this disclosure.

In another set of embodiments, the nanowire (or other nanostructured material) may include additional materials, such as semiconductor materials, dopants, organic compounds, inorganic compounds, etc. The following are non-limiting examples of materials that may be used as dopants within the nanowire. The dopant may be an elemental semiconductor, for example, silicon, germanium, tin, selenium, tellurium, boron, diamond, or phosphorous. The dopant may also be a solid solution of various elemental semiconductors. Examples include a mixture of boron and carbon, a mixture of boron and P(BP6), a mixture of boron and silicon, a mixture of silicon and carbon, a mixture of silicon and germanium, a mixture of silicon and tin, a mixture of germanium and tin, etc. In some embodiments, the dopant may include mixtures of Group IV elements, for example, a mixture of silicon and carbon, or a mixture of silicon and germanium. In other embodiments, the dopant may include mixtures of Group III and Group V elements, for example, BN, BP, BAs, AlN, AlP, AlAs, AlSb, GaN, GaP, GaAs, GaSb, InN, InP, InAs, or InSb. Mixtures of these combinations may also be used, for example, a mixture of BN/BP/BAs, or BN/AlP. In other embodiments, the dopants may include mixtures of Group III and Group V elements. For example, the mixtures may include AlGaN, GaPAs, InPAs, GaInN, AlGaInN, GaInAsP, or the like. In other embodiments, the dopants may also include mixtures of Group II and Group VI elements. For example, the dopant may include mixtures of ZnO, ZnS, ZnSe, ZnTe, CdS, CdSe, CdTe, HgS, HgSe, HgTe, BeS, BeSe, BeTe, MgS, MgSe, or the like. Alloys or mixtures of these dopants are also possible, to for example, ZnCd Se, or ZnSSe or the like. Additionally, mixtures of different groups of semiconductors may also be possible, for example, combinations of Group II-Group VI and Group III-Group V elements, such as $(GaAs)_x(ZnS)_{1-x}$. Other non-limiting examples of dopants may include mixtures of Group IV and Group VI elements, for example GeS, GeSe, GeTe, SnS, SnSe, SnTe, PbO, PbS, PbSe, PbTe, etc. Other dopant mixtures may include mixtures of Group I elements and Group VII elements, such as CuF, CuCl, CuBr, CuI, AgF, AgCl, AgBr, AgI, or the like. Other dopant mixtures may include different mixtures of these elements, such as $BeSiN_2$, $CaCN_2$, $ZnGeP_2$, $CdSnAs_2$, $ZnSnSb_2$, $CuGeP_3$, $CuSi_2P_3$, $Si_3N_4$, $Ge_3N_4$, $Al_2O_3$, $(Al, Ga, In)_2(S, Se, Te)_3$, $Al_2CO_3$ $(Cu, Ag)(Al, Ga, In, Tl, Fe)(S, Se, Te)_2$ or the like.

As a non-limiting example, a p-type dopant may be selected from Group III, and an n-type dopant may be selected from Group V. For instance, a p-type dopant may include at least one of B, Al and In, and an n-type dopant may include at least one of P, As and Sb. For Group III-Group V mixtures, a p-type dopant may be selected from Group II, including one or more of Mg, Zn, Cd and Hg, or Group IV, including one or more of C and Si. An n-type dopant may be selected from at least one of Si, Ge, Sn, S, Se and Te. It will be understood that the invention is not limited to these dopants, but may include other elements, alloys, or mixtures as well.

As used herein, the term "Group," with reference to the Periodic Table, is given its usual definition as understood by one of ordinary skill in the art. For instance, the Group II elements include Mg and Ca, as well as the Group II transition elements, such as Zn, Cd, and Hg. Similarly, the Group III elements include B, Al, Ga, In and Tl; the Group IV elements include C, Si, Ge, Sn, and Pb; the Group V elements include N, P, As, Sb and Bi; and the Group VI elements include O, S, Se, Te and Po. Combinations involving more than one element from each Group are also possible. For example, a Group II-VI material may include at least one element from Group II and at least one element from Group VI, e.g., ZnS, ZnSe, ZnSSe, ZnCdS, CdS, or CdSe. Similarly, a Group III-V material may include at least one element from Group III and at least one element from Group V, for example GaAs, GaP, GaAsP, InAs, InP, AlGaAs, or InAsP. Other dopants may also be included with these materials and combinations thereof, for example, transition metals such as Fe, Co, Te, Au, and the like. The nanoscale wire of the present invention may further include, in some cases, any organic or inorganic to molecules. In some cases, the organic or inorganic molecules are polarizable and/or have multiple charge states.

In some embodiments, at least a portion of a nanowire may be a bulk-doped semiconductor. As used herein, a "bulk-doped" article (e.g. an article, or a section or region of an article) is an article for which a dopant is incorporated substantially throughout the crystalline lattice of the article. For example, some articles such as carbon nanotubes are typically doped after the base material is grown, and thus the dopant only extends a finite distance from the surface or exterior into the interior of the crystalline lattice. In some embodiments, a bulk-doped semiconductor may comprise two or more bulk-doped regions. Thus, as used herein to describe nanowires, "doped" refers to bulk-doped nanowires, and, accordingly, a "doped nanoscopic (or nanoscale) wire" is a bulk-doped nanowire. "Heavily doped" and "lightly doped" are terms the meanings of which are understood by those of ordinary skill in the art.

In certain embodiments, a carbon nanowire can be functionalized with a thin layer that results in an affinity to the labels that increases partitioning of the current modulating label in the detection layer. In examples above hydrophobicity of a nanotube can serve the purpose of providing an attractive force that can be used to recruit conductivity-modulating labels close to the nanowire, but other interactions can be used. Optionally, pi-stacking can be used. For example, molecules with lots of pi electrons such as certain fluorescent labels will have a high affinity for a carbon nanotube beyond just what is due to the hydrophobic interaction. Further, a nanowire can be coated with charged groups to increase affinity to the conductance labels on the analogs. Yet further, the surface charge can be modified to affect the partitioning of the label.

In one set of embodiments, the invention includes a nanoscale wire (or other nanostructured material) that is a single crystal. As used herein, a "single crystal" item (e.g., a semiconductor) is an item that has covalent bonding, ionic bonding, or a combination thereof throughout the item. Such a single-crystal item may include defects in the crystal.

In yet another set of embodiments, the nanoscale wire (or other nanostructured material) may comprise two or more regions having different compositions. Each region of the nanoscale wire may have any shape or dimension, and these can be the same or different between regions. For example, a region may have a smallest dimension of less than 1 micron, less than 100 nm, less than 10 nm, or less than 1 nm. In some cases, one or more regions may be a single monolayer of atoms (i.e., "delta-doping"). In certain cases, the region may be less than a single monolayer thick (for example, if some of the atoms within the monolayer are absent).

In still another set of embodiments, a nanoscale wire may be positioned proximate the surface of a substrate, i.e., the nanoscale wire may be positioned within about 50 nm, about 25 nm, about 10 nm, or about 5 nm of the substrate. In some cases, the proximate nanoscale wire may contact at least a portion of the substrate. In one embodiment, the substrate comprises a semiconductor and/or a metal. Non-limiting examples include Si, Ge, GaAs, etc. Other suitable semiconductors and/or metals are described above with reference to nanoscale wires. In certain embodiments, the substrate may comprise a nonmetal/nonsemiconductor material, for example, a glass, a plastic or a polymer, a gel, a thin film, etc. Non-limiting examples of suitable polymers that may form or be included in the substrate include polyethylene, polypropylene, poly(ethylene terephthalate), polydimethylsiloxane, or the like.

A nanowire, nanoscopic wire on nanoscale wire is generally a wire, that at any point along its length, has at least one cross-sectional dimension and, in some embodiments, two orthogonal cross-sectional dimensions less than about 200 nm, less than about 150 nm, less than about 100 nm, less than about 70, less than about 50 nm, less than about 20 nm, less than about 10 nm, or less than about 5 nm. In other embodiments, the cross-sectional dimension can be less than 2 nm or 1 nm. In one set of embodiments, the nanoscale wire has at least one cross-sectional dimension ranging from 0.5 nm to 100 nm or 200 nm. In some cases, the nanoscale wire is electrically conductive. Where nanoscale wires are described having, for example, a core and an outer region, the above dimensions generally relate to those of the core. The cross-section of a nanoscopic wire may be of any arbitrary shape, including, but not limited to, circular, square, rectangular, annular, polygonal, or elliptical, and may be a regular or an irregular shape. The nanoscale wire may be solid or hollow. A non-limiting list of examples of materials to from which nanoscale wires of the invention can be made appears below. Any nanoscale wire can be used in any of the embodiments described herein, including carbon nanotubes, molecular wires (i.e., wires formed of a single molecule), nanorods, nanowires, nanowhiskers, organic or inorganic conductive or semiconducting polymers, and the like, unless otherwise specified. Other conductive or semiconducting elements that may not be molecular wires, but are of various small nanoscopic-scale dimensions, can also be used to form the channels of the nano-electronic measurement devices in some instances, e.g. inorganic structures such as main group and metal atom-based wire-like silicon, transition metal-containing wires, gallium arsenide, gallium nitride, indium phosphide, germanium, cadmium selenide, etc.

A wide variety of these and other nanoscale wires can be grown on and/or applied to surfaces in patterns useful for nano-electronic measurement devices in a manner similar to techniques described herein involving the specific nanoscale wires used as examples, without undue experimentation.

The nanoscale wires, in some cases, may be formed having dimensions of at least about 1 micron, at least about 3 microns, at least about 5 microns, or at least about 10 microns or about 20 microns in length, and can be less than about 100 nm, less than about 80 nm, less than about 60 nm, less than about 40 nm, less than about 20 nm, less than about 10 nm, or less than about 5 nm in thickness (height and width). The nanoscale wires may have an aspect ratio (length to thickness) of greater than about 2:1, greater than about 3:1, greater than about 4:1, greater than about 5:1, greater than about 10:1, greater than about 25:1, greater than about 50:1, greater than about 75:1, greater than about 100:1, greater than about 150:1, greater than about 250:1, greater than about 500:1, greater than about 750:1, or greater than about 1000:1 or more in some cases. The nanowires of the invention include wires that are solid, and may be elongated in some cases. In some cases, a nanowire is an elongated semiconductor, i.e., a nanoscale semiconductor.

A "nanotube" (e.g. a carbon nanotube) is typically a nanoscopic wire that is hollow, or that has a hollowed-out core, including those nanotubes known to those of ordinary skill in the art. Nanotubes are used as one example of small wires for use in the invention and, in certain embodiments, devices of the invention include wires of scale commensurate with nanotubes. Examples of nanotubes that may be used in the present invention include, but are not limited to, single-walled nanotubes (SWNTs). Structurally, SWNTs are formed of a single graphene sheet rolled into a seamless tube. Depending on the diameter and helicity, SWNTs can behave as one-dimensional metals and/or semiconductors. Methods of manufacture of nanotubes, including SWNTs, and characterization are known. Methods of selective functionalization on the ends and/or sides of nanotubes also are known, and the present invention makes use of these capabilities for molecular electronics in certain embodiments. Multi-walled nanotubes are well known, and can be used as well.

Another aspect of the invention is a hidden-Markov model (HMM) data analysis method in which the voltage transitions are explained by a hidden state (the sequence) through a 10-base context-dependent allosteric lookup table which produces about 4,000,000 different voltage levels, but each base position is interrogated 10 times by the progressing polymerase, so the sequence can be resolved by looking at the complete set of voltage transitions. One novel aspect of this approach is the recognition that the kinetics being impacted by 10 bases of context likely means that the allosteric interactions will also be strongly influenced by 10 bases of context. These effects can be as strong as the analog structure impact on the observed voltage change—meaning that the same analog in the same polymerase in one context could produce a positive change while in another context it could produce a negative change. In certain embodiments, the same DNA is sequenced with different enzymes to help resolve singularities in the HMM model that mean that errors will always occur in the same contexts. Where the 10-base context table is different for different enzymes or for different analogs used with those enzymes, the systematic errors that would normally result from ambiguous 10-base stretches will be removed.

One or more of the analogs (e.g., via the conductance label, nucleobase, phosphate chain, sugar, other modification, or a combination thereof) can produce a positive change and the other analogs produce a negative change. For example, if two produce a positive change and two produce a negative change, only two amplitudes of voltage on either side of the quiescent state voltage would be required to discern the order of base incorporation into the nascent strand.

The nano-electronic measurement devices chips can also have other incorporated components. Since the devices can be made by semiconductor processing techniques, it is straightforward to include other components such as resistors, capacitors, amplifiers, memory circuits, A/D converters, logic circuits, and the like. The circuits can provide the functions of amplification, analog to digital conversion, signal processing, memory, and data output. By having components such as CMOS processors included in the device addresses the issue of monitoring multiple events simultaneously. Rather than having at least one pair of wires bringing signals out from the chip, the inclusion of these components allows for a multiplexed output or an addressable output such as used in a DRAM chip. Where the number of devices is large, there tends to be more of a demand for building in extra circuitry onto the chip. This allows for carrying out partial analysis on the chip in a way that can significantly reduce the need for the amount of electrical signals that have to go to and from the chip.

The electrodes used in the devices including the source and the drain can be made of any suitable conducting material. They are typically made of a conductive metal that is amenable to semiconductor processing. Metals include aluminum, silver, gold, and platinum. The electrodes are fabricated to be on the order of nanometers in at least one dimension, at least two dimensions, or three dimensions. The size of the electrode is dependent on various design parameters. When discussing the size of the electrodes in this application, we are generally referring to the portion of the electrode which is exposed to the fluid sequencing mixture. In many cases, the size of the conductive portions not in contact with the solution are made larger in size to increase conductivity.

Figure 9:
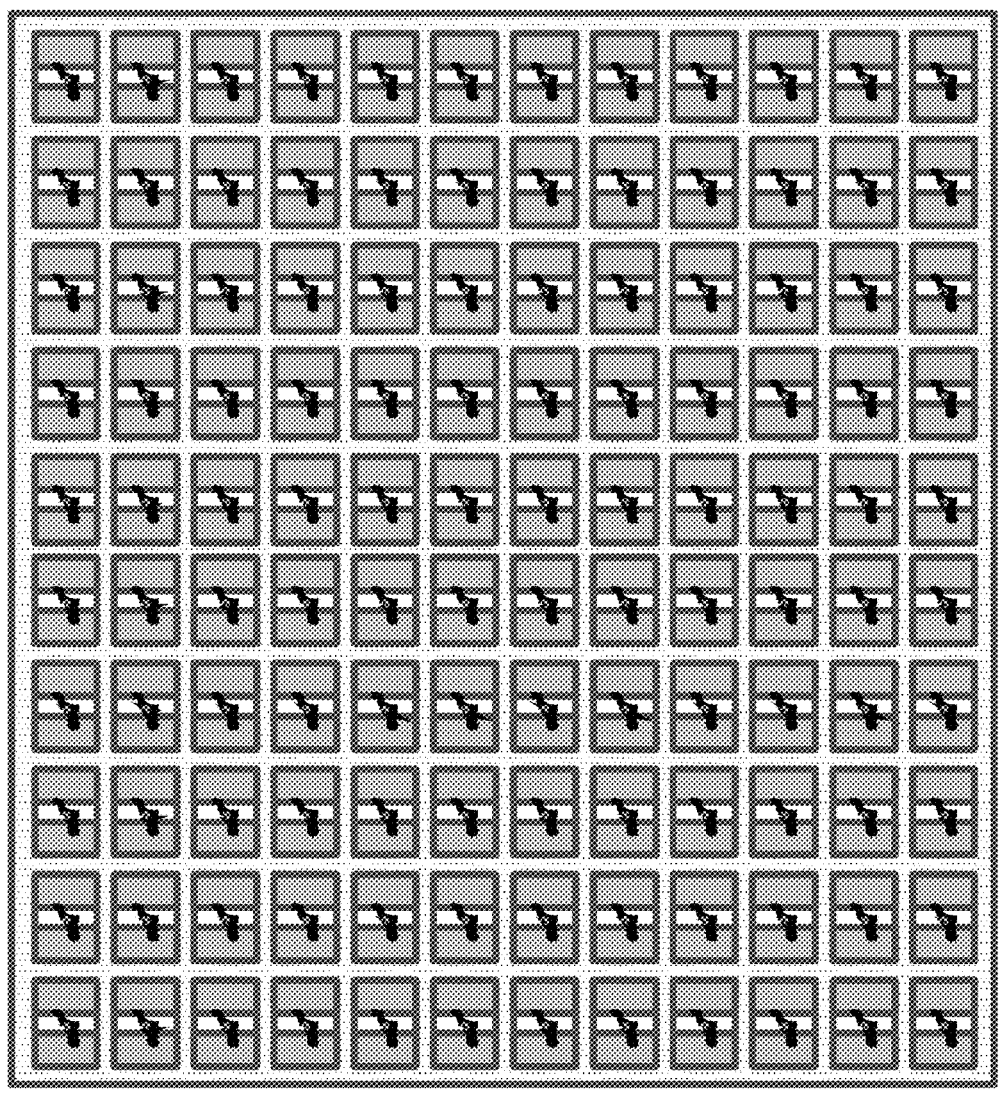
FIG. 9 illustrates how arrays of nano-electronic measurement device on a substrate can produce a sequencing device capable of concurrently sequencing multiple template nucleic acids.

FIG. 9 illustrates an array of nano-electronic measurement devices in two dimensions on a chip. A semiconductor surface can be patterned to produce an array of nano-electronic measurement devices. The interconnects to connect the nano-electronic measurement devices to the electrical inputs and outputs can be provided by dropping through vias to lower layers. The electrical connections to the chip are typically made to the sides or to the bottom of the chip.

Charge Labels

The labels of the invention are moieties that can cause a change in the electric properties of the channel of a nanoFET, e.g. a nanowire or nanotube. The labels are referred to herein as conductance labels, charge labels, impedance labels and the like. It is understood by those of skill in the art that the electronic changes in the channel of the nano-electronic measurement device can be due to changes in the electric field surrounding the channel, or, for example, changes in the conductivity of the nanowire or nanotube. In some cases, the change at the channel can be due to the displacement of charges in solution that are surrounding the channel. Often, the electrical signal at the channel is measured by putting a voltage across the source and drain of the nano-electronic measurement device, and monitoring an electrical property of the channel of the nano-electronic measurement device. Any such change in the monitored electrical property can be used to detect a charge label. In some cases, the charge label comes into contact (possibly repeated contact) with the channel, and in other cases, the charge label comes within a distance of the nanotube (channel) such that its presence is detected. The charge labels are often charged species. They can be positively charged, negatively charged or have both negative and positive charge. In some cases, the charge label can cause an increase in conductivity of the channel, and in some cases, the charge label can case a decrease in conductivity of the channel. In some cases, then the nano-electronic measurement device can be considered an ion sensitive FET or ISFET. Charge labels can be charged species that are water soluble. The charge labels can have multiple charges, e.g. from about 2 to about 2,000 charges. The charge labels can comprise dendrimers or nanoparticles. Multiple charge labels can be employed, each having a different level of charge, in some cases, with some charge labels positively charged and some charge labels negatively charged.

The charge label is selected such that when the nucleotide analog to which it is attached is within the active site of the enzyme, the charge label produces a change in conductivity of the nanowire to which the polymerase is attached or to which the polymerase enzyme is proximal. The change can be a positive change or a negative change, and where multiple charge labels are used in a single reaction mixture, one subset may produce positive changes while another subset produces negative changes. Different types of charge labels are contemplated for use with the methods provided herein. In general, charge labels include charge affecting groups, i.e., groups that enhance or diminish impedance or conductance of the channel, and are useful in applications where incorporation is detected by changes in impedance or conductance at or near the synthesis complex. Examples of charge-impacting functional groups include, e.g., long alkane chains which optionally include solubility enhancing groups, such as amido substitutions; long polyethylene glycol chains; polysaccharides; particles, such as latex, silica, polystyrene, metal, semiconductor, or dendrimeric particles; branched polymers, such as branched alkanes, branched polysaccharides, branched aryl chains. Charge labels may additionally or alternatively include electrochemical groups that detectably alter the charge of the molecule and may be detected or otherwise exploited for their electrochemical properties, such as their overall electric charge. For example, one may include highly charged groups as the functional group, like additional phosphate groups, sulfate group(s), amino acid groups or chains, e.g., polylysine, polyarginine, etc. Likewise, one may include redox active groups, such as redox active compounds, e.g., heme, or redox active enzymes. Other charge labels may include, e.g., electrochemical labels, magnetic particles, beads, semiconductor nanocrystals or quantum dots, metal nanoparticles (e.g., gold, silver, platinum, cobalt, or the like), mass labels, e.g., particle or other large moieties. A wide variety of charge labels are generally commercially available (See, e.g., the Molecular Probes Handbook, available at online at probes.invitrogen.com/handbook/), incorporated herein by reference. In some cases, nanoparticles are used as charge labels. For example, nanoparticles of metals, seimconductors, glasses, oxides, carbon, silicon, protein, polymers, ionic materials, can be used.

Figure 10:
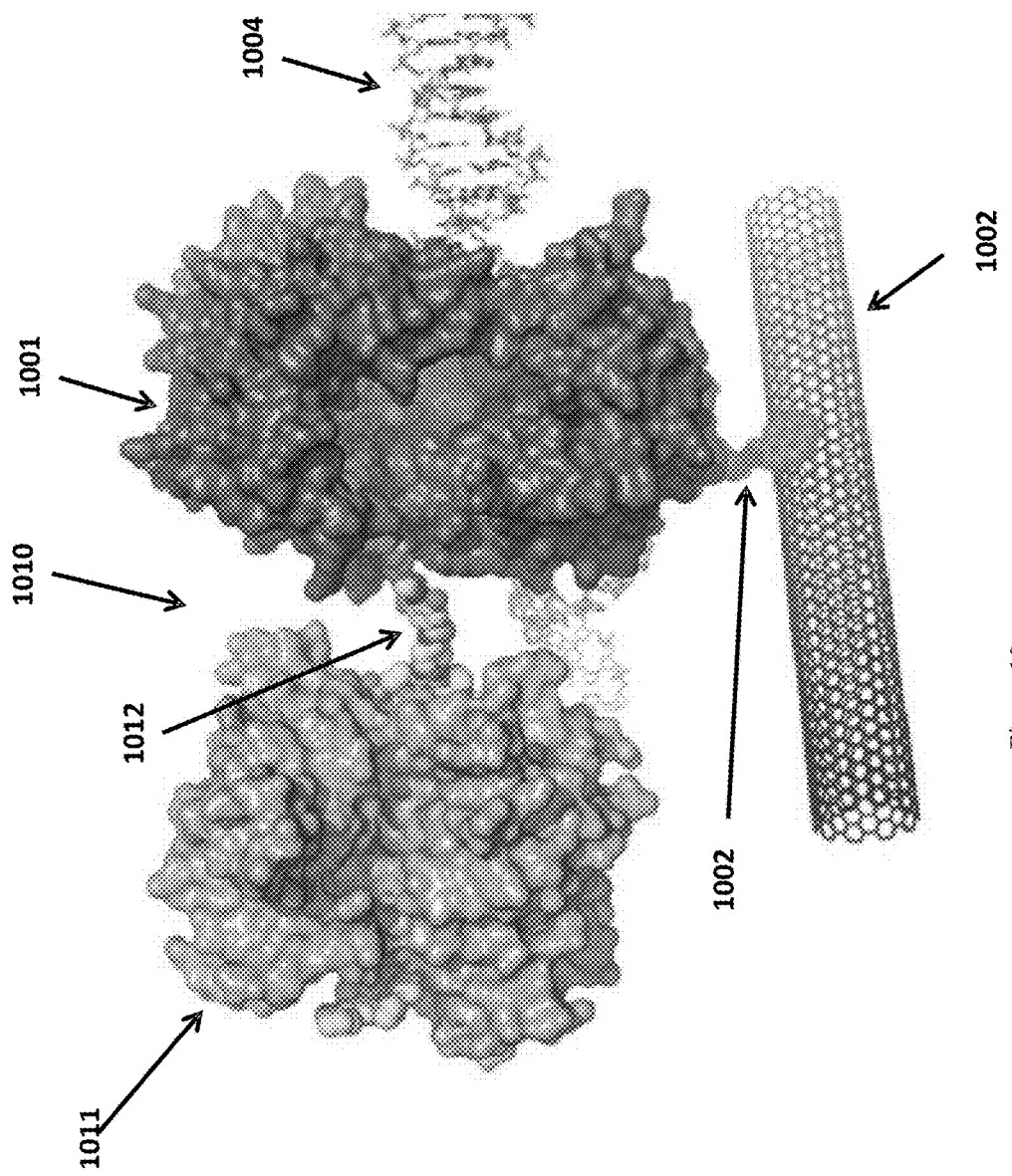
FIG. 10 illustrates carrying out nano-electronic measurement device sequencing using a protein conductance label with a size on the order of the size of a polymerase enzyme.

As described herein, for a charge label to be detected at the channel of the nano-electronic measurement device, it typically must be at least close enough to the nanowire to be within the Debye screening length. Thus, the length or size of the nucleotide analog, linker, and label must be sufficient to extend between the active site of the polymerase and the channel (e.g. nanowire or nanotube). In some cases, this can be accomplished by employing a long linker. In some cases this can be accomplished using a relatively large charge label. This charge label can be, for example, a protein. In some cases, the protein has a size on the same order of the polymerase enzyme. For example, the protein charge label can have a molecular weight from about 1/10 of the weight of the polymerase to about 3 times the molecular weight of the polymerase, or from about 1/5 of the molecular weight of the polymerase to about 2 times the molecular weight of the polymerase. The polymerase can be, for example a phi29 DNA polymerase. An example of a nucleotide analog having a protein charge label having a size on the order of the polymerase enzyme is shown in FIG. 10. Polymerase enzyme 1001 is attached to a nanotube 1002 which is the channel of a nano-electronic measurement device via linker 1003, for example through a covalent bond. The polymerase enzyme 1001 is carrying out template directed nucleic acid synthesis on nucleic acid template 1004. A nucleotide analog 1010 that has the correct (cognate) base for incorporation is held within the active site of the enzyme, and the phosphate portion of the nucleotide analog is extending out of the polymerase. Attached to the phosphate portion of the nucleotide analog through linker 1012 is charge label 1011. As can be seen in the figure, the charge label 1011 has a size that is on the order of the size of the polymerase enzyme. Because of the selection of size of the charge label, and the lengths of nucleotide analog linker 1012 and polymerase to nanotube linker 1002, the charge label is in the position to product a change in electric signal at the nanotube 1002. It would be understood by those of skill in the art that the sizes and lengths of the components described can be selected in order to control the signal that is detected at the gate. Proteins that can be used as charge labels are described, for example in [protein shield application–146], which is incorporated herein by reference, where such proteins are used as shields in nucleotide analogs. The protein charge labels can be mutated by known methods described elsewhere herein for polymerase enzymes to modify the charge and solubility characteristics of the protein charge label for control of signal measured at the nanoFET gate.

Figure 11:
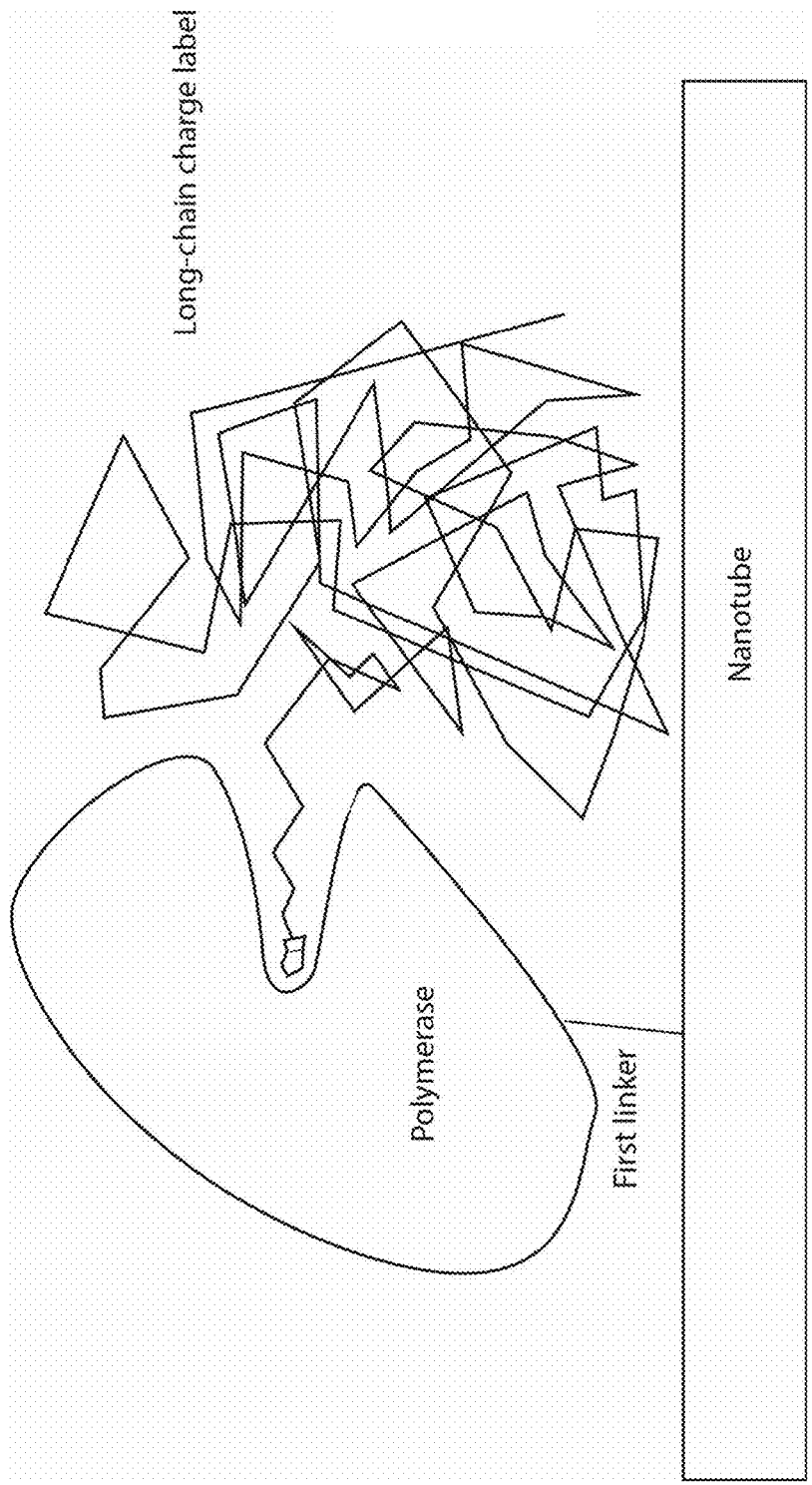
FIG. 11 shows how a long-chain conductance label can come into the vicinity of the channel of the nano-electronic measurement device and thereby be detected.

FIG. 11 illustrates how a long chain charge label can be used to provide effective signal at the gate of the nano-electronic measurement device. The length of the label can be controlled to obtain the desired level of contact of the charge label with the nanotube or nanowire while the labeled nucleotide analog is in the active site of the polymerase. For example, in the embodiment shown in FIG. 11, a long-chain charge label is linked to a nucleotide in the active site of a polymerase, where the polymerase is attached to a nanowire or nanotube via a first linker. The label is linked to the terminal phosphate of the nucleotide and has a length sufficient to produce a radius of gyration that will include the surface of the nanowire detector even from the position of the active site of the polymerase. For this purpose, molecules of about 1 nm to about 3 nm are typically used for ensuring the occasional visitation of charged portions of the labeled molecule within range of the nanowire detector, although longer molecules, up to 5, 10, 20, 40, or even 100 nm in length can also be useful. Note that the long chain is described herein as part of the charge label. It would be understood that in some cases, some of the length could be in the linker within the nucleotide analog.

In a related embodiment, a terminal phosphate charge label contains a block co-polymer or other polymer such that the label includes a hydrophobic or other non-covalent moiety that has affinity for the nanotube. This label can be charged or uncharged. The affinity of the polymer for the nanotube results in the polymer and therefore the label spending more time within the detection region near the nanotube. That is, the polymer will be gyrating over time, and its affinity for the nanotube will allow for it to partition towards the surface (and hence the detection region) of the nanotube. In a preferred embodiment of this strategy, the off rate of the non-covalent binding moiety is greater than 10 times the incorporation rate of the polymerase or more preferably more than 100 times the incorporation rate of the polymerase, or even more preferably more than 500 times the incorporation rate of the polymerase. In some embodiments, the duty cycle of association with the nanowire is 50% higher than without the moiety or 100% higher or 300% higher or 1000% higher that without the moiety or greater.

Distinguishing Labels—Calling Bases

In the sequencing methods of the invention, there are usually two or more different types of labeled nucleotide analogs, and typically there are four different types of nucleotide analog. There are various approaches to distinguish the various types of bases. The discussion will generally involve distinguishing four bases but it is understood that the same approaches can be used to distinguish, two, three, five or more types of nucleotide analogs.

Figure 12:
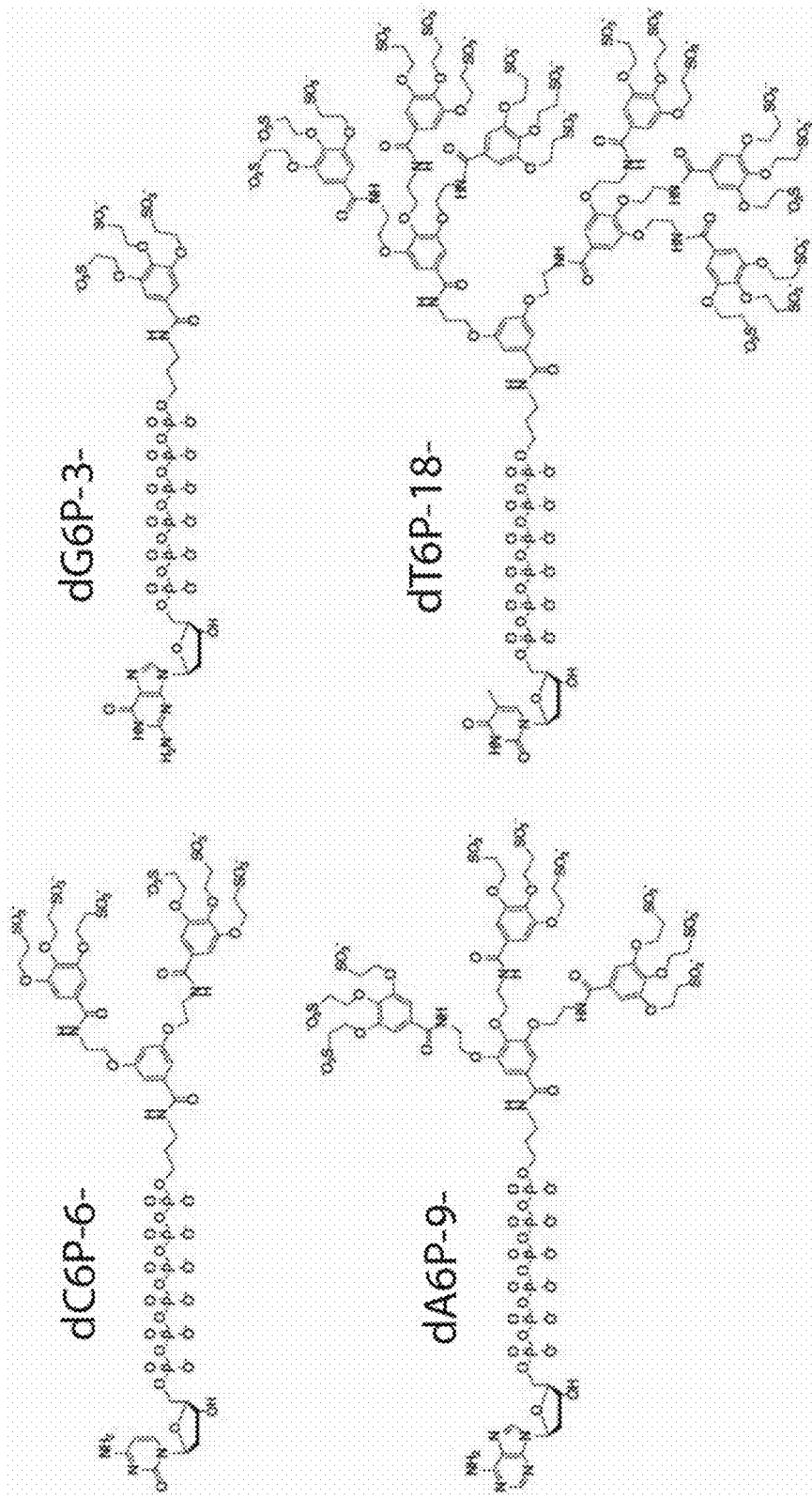
FIG. 12 shows an exemplary set of nucleotide analogs providing four differentiable charged charge labels.

One example of such a set of four differently labeled nucleotide analogs is shown in FIG. 12. Each of four different nucleotide types carries a distinguishable charge label, with 3, 6, 9 or 18 negative charges. There are four different nucleotide analogs. The analogs correspond to analogs for DNA synthesis corresponding to the natural bases C, G, A, and T. In each of the analogs, the polyphosphate chain has 6 phosphates. Here the charged charge labels are connected through a relatively short linker of a few carbons. One of skill will appreciate that this is an illustrative set of nucleotide analogs, and that changes in the nucleotide portion, the number of phosphates in the polyphosphate change, the length and chemical structure of the linker and the relative number of charges can be changed in order to select the desired level of signal at the nano-electronic measurement devices for the sequencing system of interest.

Figure 13:
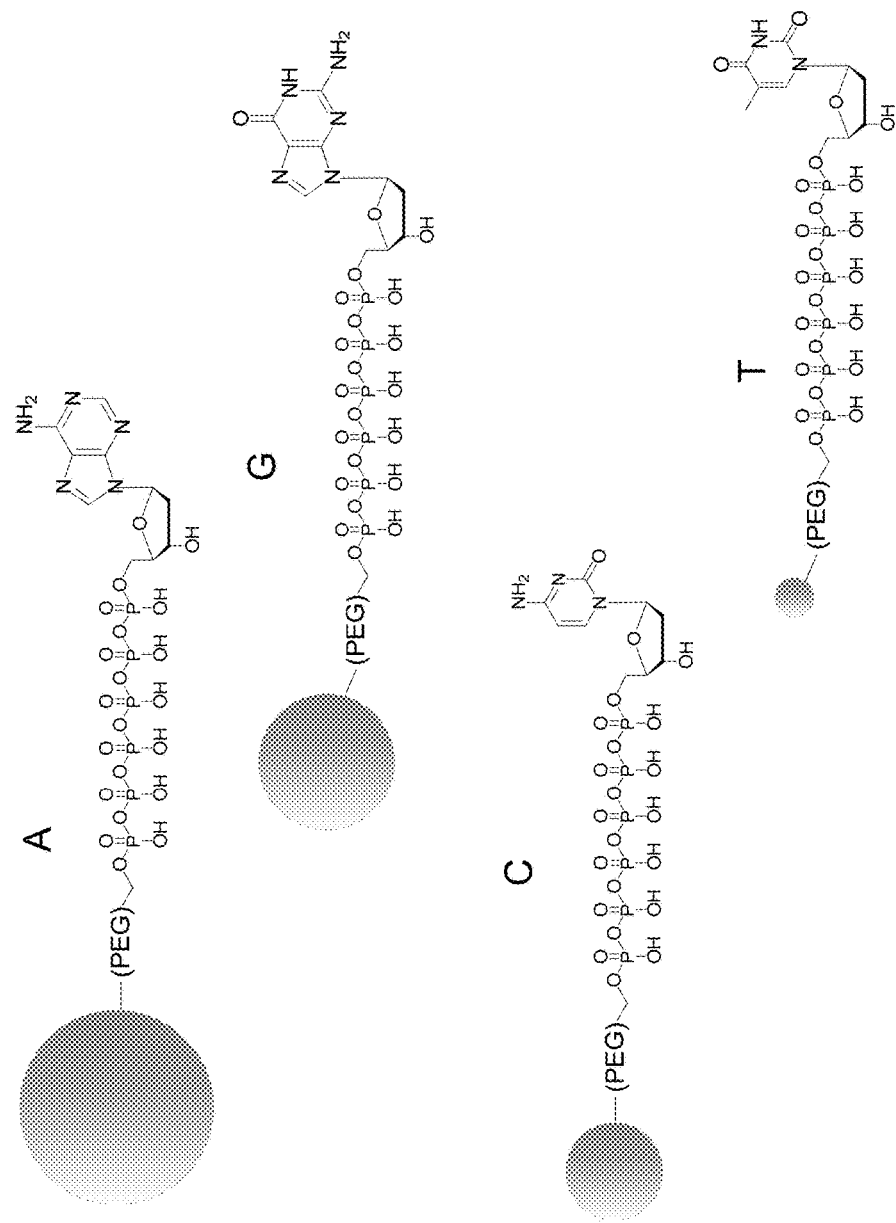
FIG. 13 shows an exemplary set of nucleotide analogs providing four differentiable nanoparticle charge labels.

One example of such a set of four differently labeled nucleotide analogs is shown in FIG. 13. Each of the analogs has a nucleotide portion comprising a hexaphosphate, a deoxy ribose, and a nucleobase. Attached to the terminal phosphate of the nucleotide moiety is a polyethylene glycol (PEG) linker. The PEG linker has 77 PEG units and is connected to the charge label. Attached to each of the nucleotide analogs is a sphere of a different size. In this example, polystyrene spheres are used. In other examples, for example, titanium dioxide, or gold spheres are used. The nucleotide analog corresponding to G has a polystyrene sphere with diameter of about 15 nm. The nucleotide analog corresponding to A has a polystyrene sphere with diameter of about 25 nm. The nucleotide analog corresponding to T has a polystyrene sphere with diameter of about 5 nm, and the nucleotide analog corresponding to C has a polystyrene sphere with diameter of about 10 nm. This is just one of many sets of four different nucleotide analogs that can be used for sequencing. In some cases, rather than four different sized nanoparticles, the four different nucleotides can each have the same type and size of nanoparticle, but each having a different type of linker.

Distinguishing nucleotide types is done, for example, using the characteristics of magnitude of impedance, impedance versus frequency, and impedance current versus time characteristics (current oscillation color) measured at the channel of the nano-electronic measurement device. Combinations of the above can also be useful; for example by using two labels and two amplitudes; two types of impedance versus frequency, and two types of current oscillation color, etc. For example, controlling the number, density, and type of charge, and the use of macromolecular charged labels can be useful for either type of electrical detection.

Charge labels that can provide differences in channel conductivity are known in the art. In some cases, small molecules can be used. In some case a particle, such as a nanoparticle is used as the charge label. The characteristics of the nanoparticle can be varied in order to produce different electrical signals through the channel of the nanoFET. The size of the nanoparticle can influence the capacitance of the particle, as well as the chemical structure. Nanoparticles of metals, seimconductors, glasses, oxides, carbon, silicon, protein, polymers, ionic materials, can be used and can be produced to have widely different channel conductivity magnitude and gate conductivity versus frequency characteristics. The size of the particles can be varied over a wide range, for example from about 2 nanometers to about 50 nanometers in diameter. One contributor to the electrical signal change near an electrode is the capacitance characteristics of the nano-electronic measurement device and associated nanowires. However, it is to be understood that the impedance that is being measured is that of the region around the electrode, and not just that of the label. For example, a nanoparticle label will displace the solution near the electrode, such that the measured electrical signal at the channel will include that change. Thus, a label near the channel of the nano-electronic measurement device can result in the conductivity either going up or going down as compared to the conductivity when the charge label is not present.

Differentiating nucleotide analogs based on the magnitude conductivity change can be carried out, for example, by providing a charge label having multiple conductive moieties on a nucleotide analog. Nucleotide analog structures including those having multivalent scaffolds and nucleotides having multiple moieties can be prepared as described, for example, in US Patent Application 20120058473 entitled "Molecular Adaptors for Dye Conjugates," and U.S. Pat. No. 8,906,612 entitled "Scaffold-Based Polymerase Enzyme Substrates," which are incorporated herein by reference for all purposes. While these references generally describe a fluorescent label, it is to be understood in conjunction with the teachings of this application that a suitable charge label connected by a suitable linker as described herein can be substituted for the fluorescent label.

The terms impedance, conductivity, and capacitance are used herein to describe electrical characteristics, of a channel of a nano-electronic measurement devices. It is to be understood that impedance is a more general term, and that impedance typically has both capacitive and resistive (conductivity) components. For example, for a given system, current flow at low frequencies is dominated by the level of conductivity or resistivity, while the current flow at high frequencies is dominated by the level of capacitance. In some cases frequencies are on the order of tens of kilohertz or greater. At these frequencies, for the geometries and materials described, the impedance is predominated by capacitive rather than resistive components. In some cases, low frequencies including DC can be used in which resistivity (conductivity) is the dominant component. While the impedance in each case may be dominated by one component, either capacitance or resistivity, it is will be understood by those of skill in the art that in some cases a combination of these components is present and those of skill in the art will understand the meanings of the terms by their context herein.

Nucleotide analogs can also be differentiated by their impedance versus frequency characteristics. The measured impedance of a label will also be highly dependent on the frequency. It is well known that the components that contribute to impedance in a given system can vary significantly with frequency, for example ionic motion can predominate at some frequencies and dipolar contributions can predominate at other frequencies. Measurements of this type are sometimes referred to as impedance spectroscopy or dielectric spectroscopy measurements. See e.g. Barsoukov, et al. "Impedance Spectroscopy: Theory, Experiment, and Applications", Wiley, 2005, and Kremer et al. "Broadband dielectric spectroscopy", Springer, 2003, the contents of which are incorporated herein by reference for all purposes. Different labels exhibit different impedance versus frequency characteristics, and these characteristics can be used to provide distinct labels and to increase the confidence in base calling.

The impedance of a label can also vary with the amplitude of the voltage applied to the nanoscale electrode at a given frequency. The voltage applied can be adjusted to obtain the best distinction between the various labels. In some cases, the voltage can be varied instead of or in addition to varying the frequency as described above, allowing labels to be distinguished, at least in part, by their impedance versus electrode voltage characteristics.

The current versus time characteristics can be referred to as current oscillation color. For example, two nucleotide analogs, each having the same charge label but having different length linkers can exhibit different electrical signal versus time characteristics. Current oscillation color can be used for nano-electronic measurement devices. The nucleotide with the longer linker, may, for example, diffuse differently and thus exhibit a different impedance over time characteristics than the nucleotide analog with the shorter linker. This difference in frequency of current oscillation can be used to determine which of the nucleotide analogs is associated with the enzyme. In addition to linker length, the current oscillation color can be influenced by other characteristics of the linker such as its spring constant. The current oscillation color will depend on the characteristics of the measurement system such as electrode geometry and polymerase complex attachment. These factors can be chosen to control differences in current oscillation color to enhance the determination of which nucleotide is incorporated.

Nucleotides or analogs that can thus be identified by the spectrum of the electrical oscillation they produce. In some cases, oscillations looks like noise, but with reproducible and identifiable characteristics including the frequency and the magnitude of the signal. These different types of oscillations can be used like different colored dyes are used to differentiate between different nucleotide analogs in optical systems, thus, we refer herein to a distinguishable type of current oscillation as a current oscillation color.

One aspect of the invention is the utilization of additional parameters beyond just the impedance change and the impedance spectrum of a label to classify the species associated with the enzyme. Such parameters are measurable over the duration of a pulse. Two general categories of measurement scenarios are: quasi-equilibrium measurement and non-equilibrium measurement.

In quasi-equilibrium measurement, there is some static constraint that remains in place over the duration of the event, and that the removal of that constraint effectively determines the end of the event (except for a negligibly short interval at the end while the detectable object clears the electrode). Though the constraint is fixed, the rest of the components of the system are free to move, and this leads to fluctuations in the signal. For example, diffusion (or equivalently Brownian motion) will cause movement of the label. Under most circumstances, that motion will be correlated with changes in the current across the nanopore, and thus the voltages that might be measured elsewhere in the system. Because of this, aspects of the detectable moiety such as the submolecular diffusion constant (the diffusibility of just that part of the molecule, even when another part of the molecule is constrained) will change the speed of those motions and thus the characteristic frequencies with which the observed voltages or currents will change. For example, a fast diffuser will generally have a whiter noise spectrum, while a slower diffuser will tend to produce a pinker current oscillation spectrum.

The current oscillation color can be used as the basis for a discriminator, for example, by 1) taking the current oscillation signature over a region of interest (e.g. over the duration of the event), 2) performing a Fourier transform analysis or an autocorrelation analysis, and examine the spectrum of the current oscillation over the range of frequencies available (e.g. from f=1/T where T is the duration of the pulse, up to the cutoff frequency of the amplifier system, or somewhat beyond the cutoff). This process will result in a digitally sampled current oscillation amplitude as a function of frequency. This could be represented by as few as two samples (a low frequency region and a high frequency region), 3, 4, 5, 6, 7, 8, 9, 10, 11, 12, 16, 32, 64, 128, 256, 512, 1024 or more bins. The values in these bins could be discrete samples of a function or they represent integrals over a region of interest of the idealized continuous function. This set of discrete values can be represented as a vector that can be classified by one of many machine learning systems such as k-means clustering, SVM, CART or boosted CART, PCA and many others. Thus, as described herein, current oscillation color can be used to discriminate detectable moieties. Detection systems that are based on current oscillation color can be referred to as "current oscillation color identification systems", and when moieties engineered for producing different current oscillation color are used, they are referred to as "current oscillation color tags." In a sequencing system, when nucleotide base sequence is identified on this basis it can be referred to as a current oscillation color sequencing system (whether the current oscillation color is intrinsic to the bases or the result of current oscillation color tags).

Other aspects besides the diffusion constant can affect the current oscillation color of the signal. For example, in the embodiments that use linkers with different elastic constants, this will affect the magnitude of these diffusive fluctuations, which will then affect the current oscillation signal (not to be confused with the amplitude of the DC current during the event—this is referring to the RMS noise of the signal over the duration of the event.). In analogy with color systems that have RGB, or HSV, color can be generalized to include the "brightness" of the color. In the above-mentioned spectrum analysis model, this would result in the values in the vector being larger for moieties capable of larger excursions, and lower values for moieties that are more constrained in position. Some or all of these signals can be exploited in the machine learning paradigm indicated above. There are many aspects that can affect the size of the excursions.

The nanoscale electrodes used to connect the nano-electronic measurement devices or that are part of the nano-electronic measurement device, e.g. the source and the drain are typically prepared such that the electrodes have low capacitance in order to allow for rapidly changing the voltage on the electrodes to carry out the sequencing methods described herein. The resistance and capacitance are kept low by the selection of materials and by the geometry of the electrodes and the spacing of the electrodes. One of the considerations is keeping the RC time constant of each capacitive device low enough to allow for changing the voltage on the electrodes to carry out the methods described herein. In some cases, the RC time constant for the electrode is less than 100 microseconds, less than 10 microseconds, less than 1 microsecond, less than 0.1 microseconds, or less than 0.01 microseconds. In some cases, the RC time constant is between 0.01 microseconds and 100 microseconds. In order to keep the RC time constant low, the electrodes and the interconnects that carry current to and from the electrodes are formed from a material having an electrical conductivity of greater than 106 S/m. Suitable materials include copper, silver, gold, platinum, and aluminum. In order to keep the capacitance low, the dimensions of the electrodes are also generally small—on the nanometer scale. In addition, where there are two electrodes near each other as in the two electrode configuration, while the electrode portions exposed to the surface are close together, the electrodes are configured not to have large portions where the two electrodes are within a few nanometers. It is also an aspect of the invention to minimize the area of electrodes that is in contact with conductive liquid so as to control the capacitance of the system. Similarly it is an aspect of the invention to use insulating layers to increase the distance to ground planes, other electrodes, or any other conductor which could produce stray capacitance.

The ability to electrically address the small nano-electronic measurement devices of the instant invention quickly due to the low RC time constant of the structures is useful for carrying out the invention as it allows for sampling multiple frequency regimes to identify the identity of the different components that are present.

The methods described herein provide for identifying the nucleotide analogs that are incorporated in to a growing nucleic acid strand as they are incorporated in the bound polymerase-template complex. The presence and identity of the bases is measured by measuring electrical signals in the nano-electronic measurement devices proximate to the bound polymerase-template complex. As described above, the presence of a charge label corresponding to a particular base proximate to a nano-electronic measurement device for a period of time corresponding to the time for base incorporation indicates that that base has been incorporated. The incorporation of that base into the growing strand indicates the presence of the complementary base in the template strand, providing sequence information about the template. The calling of bases is done using software that takes the current versus time information, and in some cases other information in order to call the base that has been incorporated.

An exemplary process for pulse recognition is as follows. Once the current traces have been generated for a given nano-electronic measurement devices for a certain time period, the current traces are subjected to a pulse recognition process. In the initial step, a baseline is established for the trace. Typically, the baseline may comprise signal contributions from a number of background sources (depending on the details of the spectral and trace extraction steps). For example, such noise can include, e.g., global background (e.g. large scale spatial cross-talk) and diffusion background. These backgrounds are generally stable on the timescales of pulses, but still may vary slowly over longer timescales. Baseline removal comprises any number of techniques, ranging from, e.g.: a median of the trace, running lowest-percentile with bias correction, polynomial and/or exponential fits, or low-pass filtering with an FFT. Generally these methods will attempt to be robust to the presence of pulses in the trace and may actually be derived at through iterative methods that make multiple passes at identifying pulses and removing them from consideration of baseline estimation. In certain preferred embodiments, a baseline or background model is computed for each trace channel, e.g., to set the scale for threshold-based event detection.

Other baselining functions include correction for drift or decay of overall signal levels. For example, global background decay is sometimes observed. This global background decay is present on portions of the substrate at which there is no enzyme bound proximate to nano-electronic measurement devices, thus allowing the traces derived from these locations to be used in combination with the two dimensional global background image to estimate the contribution of this signal to every trace/channel across the chip. This component of variability can then be subtracted from each trace and is usually very effective at removing this decay. Typically, this is carried out prior to the baselining processes.

Following establishment of the baseline the traces are subjected to noise suppression filtering to maximize pulse detection. In particularly preferred aspects, the noise filter is a 'matched filter' that has the width and shape of the pulse of interest. While current pulse timescales (and thus, pulse widths) are expected to vary among different capacitive labeled nucleotides, the preferred filters will typically look for pulses that have a characteristic shape with varying overall duration. For example, a boxcar filter that looks for a current pulse of prolonged duration, e.g., from about 10 ms to 100 or more ms, provides a suitable filter. This filtering is generally performed in the time-domain through convolution or low-pass frequency domain filtering. Other filtering techniques include: median filtering (which has the additional effect of removing short timescale pulses completely from the trace depending on the timescale used), and Savitsky-Golay filtering which tends to preserve the shape of the pulse—again depending on the parameters used in the filter).

Although described in terms of a generic filtering process across the various traces, it will be appreciated that different pulses may have different characteristics, and thus may be subjected to trace specific filtering protocols. For example, in some cases, a given labeled analog (e.g., A) may have a different pulse duration for an incorporation event than another different labeled analog (e.g., T). As such, the filtering process for the spectral trace corresponding to the A analog will have different filtering metrics on the longer duration pulses, than for the trace corresponding to the T analog incorporation. In general, such filters (e.g., multi-scale filters) enhance the signal-to-noise ratio for enhanced detection sensitivity. Even within the same channel there may be a range of pulse widths. Therefore typically a bank of these filters is used in order to maximize sensitivity to pulses at a range of timescales within the same channel.

In identifying pulses on a filtered trace, a number of different criteria can be used. For example, one can use absolute current amplitude, either with or without normalization. Alternatively, one can identify pulses from the pulse to diffusion background ratio as a metric for identifying the pulse. In still other methods, one may use statistical significance tests to identify likely pulses over the background noise levels that exist in a given analysis. The latter method is particularly preferred as it allows for variation in potential pulse intensities, and reduces the level of false positives called from noise in the baseline.

As noted previously, a number of signal parameters including amplitude of capacitance change, impedance versus frequency, residence time, and current oscillation color may be and generally are used in pulse identification (as well as in pulse classification). For purposes of illustration, the discussion below primarily on the use of two pulse metrics, namely pulse intensity and pulse width. As will be appreciated, the process may generally include any one or more of the various pulse metric comparisons set forth elsewhere herein.

As such, following filtering, standard deviation of the baselines (noise and current pulses) and determination of pulse detection thresholds are carried out. Preferred methods for determining the standard deviation of a trace include robust standard deviation determinations including, e.g., being based upon the median absolute difference about the baseline, a Gaussian or Poisson fit to the histogram of baselined intensities, or an iterative sigma-clip estimate in which extreme outliers are excluded. Once determined for each trace, a pulse is identified if it exceeds some preset number of standard deviations from the baseline. The number of standard deviations that constitute a significant pulse can vary depending upon a number of factors, including, for example, the desired degree of confidence in identification or classification of significant pulses, the signal to noise ratio for the system, the amount of other noise contributions to the system, and the like. In a preferred aspect, the up-threshold for an incorporation event, e.g., at the initiation of a pulse in the trace, is set at about 5 standard deviations or greater, while the down-threshold (the point at which the pulse is determined to have ended) is set at 1.25 standard deviations. Up thresholds can be used as low as 3.75 standard deviations and as high as the signal-to-noise ratio will allow—up to 7, 10, 20 or 50 standard deviations. The down threshold can be set anywhere from minus 1 standard deviation up to the up threshold. Alternatively, the down threshold can be computed from the mean and standard deviation of the up signal, in which case it could be set between minus 3 standard deviations to minus 6 standard deviations. If the signal-to-noise ratio is sufficiently high it could be set to minus 7, 10, 20 or 50 standard deviations. The pulse width is then determined from the time between the triggering of the up and down thresholds. Once significant pulses are initially identified, they are subjected to further processing to determine whether the pulse can be called as a particular base incorporation. Alternatively the signals can be filtered ahead of time to eliminate frequency components that correspond to timescales not likely to correspond to true incorporation events, in which case the further processing steps are optional.

In some cases, multiple passes are made through traces examining pulses at different timescales, from which a list of non-redundant pulses detected at such different time thresholds may be created. This typically includes analysis of unfiltered traces in order to minimize potential pulse overlap in time, thereby maximizing sensitivity to pulses with width at or near the highest frame rate of the camera. This allows the application of current oscillation color or other metrics to current pulses that inherently operate on different timescale. In particular, an analysis at longer timescales may establish trends not identifiable at shorter timescales, for example, identifying multiple short timescale pulses actually correspond to a single longer, discrete pulse.

In addition, some pulses may be removed from consideration/evaluation, where they may have been identified as the result of systematic errors, such as through spatial cross-talk of adjacent devices, or cross-talk between detection channels (to the extent such issues have not been resolved in a calibration processes). Typically, the calibration process will identify cross-talk coefficients for each device, and thus allow such components to be corrected.

In certain embodiments, a trace-file comprises L-weighted-sum (LWS) traces, where trace is optimized to have maximum pulse detection sensitivity to an individual label in the reaction mixture. This is not a deconvolved or multicomponent trace representation, and suffers from spectral cross-talk.

Classification of an extracted pulse into one of the 4 (or N) labels is then carried out by comparing the extracted spectrum to the spectra of the labels sets established in a calibration process. A number of comparative methods may be used to generate a comparative metric for this process. For example, in some aspects, $\chi 2$ test is used to establish the goodness of fit of the comparison. A suitable $\chi 2$ test is described, for example, in U.S. Patent Application 20120015825, incorporated herein by reference for all purposes.

Once the pulse spectrum is classified as corresponding to a particular label spectrum, that correlation is then used to assign a base classification to the pulse. As noted above, the base classification or "calling" may be configured to identify directly the labeled base added to the extended primer sequence in the reaction, or it may be set to call the complementary base to that added (and for which the pulse spectrum best matches the label spectrum). In either case, the output will be the assignment of a base classification to each recognized and classified pulse. For example, a base classification may be assignment of a particular base to the pulse, or identification of the pulse as an insertion or deletion event.

In an ideal situation, once a pulse is identified as significant and its spectrum is definitively identified, a base is simply called on the basis of that information. However, as noted above, in typical sequencing runs, signal traces can include signal noise, such as missing pulses (e.g., points at which no pulse was found to be significant, but that correspond to an incorporation event) false positive pulses, e.g., resulting from nonspecifically adsorbed analogs or labels, or the like. Accordingly, pulse classification (also termed base classification) can in many cases involve a more complex analysis. As with pulse identification, above, base classification typically relies upon a plurality of different signal characteristics in assigning a base to a particular identified significant pulse. In many cases, two, three, five, ten or more different signal characteristics may be compared in order to call a base from a given significant pulse. Such characteristics include those used in identifying significant pulses as described above, such as pulse width or derivative thereof (e.g., smooth pulse width estimate, cognate residence time, or non-cognate residence time), pulse intensity, pulse channel, estimated average current amplitude of pulse, median current amplitude of all pulses in the trace corresponding to the same channel, background and/or baseline level of channel matching pulse identity, signal to noise ratio (e.g., signal to noise ratio of pulses in matching channel, and/or signal to noise ratio of each different channel), power to noise ratio, integrated counts in pulse peak, maximum signal value across pulse, pulse density over time (e.g., over at least about 1, 2, 5, 10, 15, 20, or 30 second window), shape of and distance/time to neighboring pulses (e.g., interpulse distance), channel of neighboring pulses (e.g., channel of previous 1, 2, 3, or 4 pulses and/or channel of following 1, 2, 3, or 4 pulses), similarity of pulse channel to the channel of one or more neighboring pulses, signal to noise ratio for neighboring pulses; spectral signature of the pulse, pulse centroid location, and the like, and combinations thereof. Typically, such comparison will be based upon standard pattern recognition of the metrics used as compared to patterns of known base classifications, yielding base calls for the closest pattern fit between the significant pulse and the pattern of the standard base profile.

Comparison of pulse metrics against representative metrics from pulses associated with a known base identity will typically employ predictive or machine learning processes. In particular, a "training" database of "N previously solved cases" is created that includes the various metrics set forth above. For example, a vector of features is analyzed for each pulse, and values for those features are measured and used to determine the classification for the pulse, e.g., an event corresponding to the pulse, e.g., an incorporation, deletion, or insertion event. As used herein, an incorporation event refers to an incorporation of a nucleotide complementary to a template strand, a deletion event corresponds to a missing pulse resulting in a one position gap in the observed sequence read, and an insertion event corresponds to an extra pulse resulting in detection of a base in the absence of incorporation. For example, an extra pulse can be detected when a polymerase binds a cognate or noncognate nucleotide but the nucleotide is released without incorporation into a growing polynucleotide strand. From that database, a learning procedure is applied to the data in order to extract a predicting function from the data. A wide variety of learning procedures are known in the art and are readily applicable to the database of pulse metrics. These include, for example, linear/logistic regression algorithms, neural networks, kernel methods, decision trees, multivariate splines (MARS), multiple additive regression trees (MART™), support vector machines.

In addition to calling bases at pulses identified as significant, the present methods also allow for modeling missing pulses. For example, conditional random fields (CRF) are probabilistic models that can be used to in pulse classification (see, e.g., Lafferty, et al. (2001) Proc. Intl. Conf. on Machine Learning 01, pgs. 282-289, incorporated herein by reference in its entirety for all purposes). A CRF can also be conceptualized as a generalized Hidden Markov Model (HMM), some examples of which are described elsewhere herein and are well known in the art. The present invention includes the use of CRFs to model missing bases in an observed pulse trace. In addition to base calling, algorithms for consensus generation and sequence alignment can be used to obtain further information from the sequencing methods described herein.

Methods for calling bases, consensus generation, and sequence alignment are described, for example, in the following patents and applications, which are incorporated herein for all purposes: U.S. Pat. No. 7,995,202, entitled "Methods and Systems for Simultaneous real-time monitoring of optical signals from multiple sources"; U.S. Pat. No. 7,626,704 entitled "Methods and systems for simultaneous real-time monitoring of optical signals from multiple sources"; U.S. Pat. No. 8,182,993 entitled "Methods and Processes for Calling Bases in Sequence by Incorporation Methods"; U.S. Ser. No. 13/468,347 filed May 10, 2012, entitled "Algorithms for Sequence Determination"; US 20120015825 entitled "Analytical Systems and Methods with Software Mask"; US 20110257889 entitled "Sequence Assembly and Consensus Sequence Determination"; US 20120052490 entitled "Methods and Systems for Monitoring Reactions"; US 20100169026 entitled "Algorithms for Sequence Determination Processing the data". While the base identification and base calling algorithms in the above documents are typically described referring to optical systems, in light of the current specification, one of ordinary skill in the art would understand how to bring such methods to bear in the nano-electronic measurement devices sequencing systems and methods of the present invention.

Polymerase-Nucleic Acid Complex

The polymerase-enzyme complex of the invention comprises a nucleic acid polymerase enzyme associated with a template molecule. The template also typically has a primer hybridized to it, while some polymerase enzymes can initiate nucleic acid synthesis without the addition of an external primer. While many enzyme-substrate interactions are transient, some polymerase enzymes can form relatively stable complexes with nucleic acids that can be manipulated, purified, and then subsequently used to carry out nucleic acid synthesis. For example, DNA polymerases having relatively high processivity can have strong associations with template nucleic acid molecules. An exemplary DNA Polymerase is phi-29 DNA polymerase. Methods for forming and manipulating polymerase-nucleic acid complexes are described, for example in copending U.S. Patent Application entitled Purified Extended Polymerase/Template Complex for Sequencing" 61/385,376, filed Sep. 22, 2010 and U.S. Pat. No. 8,658,364 entitled "Isolation of Polymerase-Nucleic Acid Complexes" which is incorporated by reference herein in its entirety for all purposes.

The polymerase-nucleic acid complex will typically comprise a polymerase and a nucleic acid having a double stranded region. The polymerase-nucleic acid complex will generally have a primer from which a nascent nucleic acid strand will be produced complementary to a template strand of the nucleic acid. The primer is usually a short oligonucleotide that is complementary to a portion of the template nucleic acid. The primers of the invention can comprise naturally occurring RNA or DNA oligonucleotides. The primers of the invention may also be synthetic analogs. The primers may have alternative backbones as described above for the nucleic acids of the invention. The primer may also have other modifications, such as the inclusion of heteroatoms, the attachment of labels, or substitution with functional groups which will still allow for base pairing and for recognition by the enzyme. Primers can select tighter binding primer sequences, e.g., GC-rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template. In some cases, the primer is added as a separate component to form the complex; in other cases, the primer can be part of the nucleic acid that used. For example, in some cases priming can begin at a nick or a gap in one strand of a double-stranded nucleic acid.

The template nucleic acid can be derived from any suitable natural or synthetic source. In preferred embodiments, the template comprises double stranded DNA, but in some circumstances double-stranded RNA or RNA-DNA heteroduplexes can be used. The template nucleic acid can be genomic DNA from eukaryotes, bacteria, or archaea. The template nucleic acid can be cDNA derived from any suitable source including messenger RNA. The template nucleic acid can comprise a library of double stranded segments of DNA. The template nucleic acid can be linear or circular. For example, the nucleic acid can be topologically circular and have a linear double stranded region. A circular nucleic acid can be, for example, a gapped plasmid. In some embodiments the nucleic acid is a double stranded linear DNA having a gap in one of the strands. The gap provides a site for attachment of the polymerase enzyme for nucleic acid synthesis. The linear double stranded DNA having a double-stranded DNA adaptor can be made by ligation of DNA fragment to an adaptor through blunt end-ligation or sticky end ligation. The ligation produces a linear DNA having a gap close to the 5' end of one or both of the strands. The gap can be any suitable width. For example, the gap can be from 1 to 50 bases, from 2 to 30 bases, or from 3 to 12 bases.

The terms "nucleic acid" or "oligonucleotide" or grammatical equivalents herein mean at least two nucleotides covalently linked together. A nucleic acid of the present invention will generally contain phosphodiester bonds, although in some cases, nucleotide analogs are included that may have alternate backbones, comprising, for example, phosphoramide, phosphorothioate, phosphorodithioate, and peptide nucleic acid backbones and linkages. Other analog nucleic acids include those with positive backbones, non-ionic backbones, and non-ribose backbones, including those described in U.S. Pat. Nos. 5,235,033 and 5,034,506. The template nucleic acid may also have other modifications, such as the inclusion of heteroatoms, the attachment of labels, or substitution with functional groups which will still allow for base pairing and for recognition by the enzyme.

The template sequence may be provided in any of a number of different format types depending upon the desired application. The template may be provided as a circular or functionally circular construct that allows redundant processing of the same nucleic acid sequence by the synthesis complex. Use of such circular constructs has been described in, e.g., U.S. Pat. Nos. 7,315,019 and 7,901,889. Alternate functional circular constructs are also described in U.S. Pat. No. 8,236,499 "Methods and Compositions for Nucleic Acid Sample Preparation"; U.S. Pat. No. 8,153,375 "Compositions and Methods for Nucleic Acid Sequencing; U.S. Pat. No. 8,003,330 "Error-Free Amplification of DNA for Clonal Sequencing"; and Ser. No. 13/363,066 filed Jan. 31, 2012 entitled "Methods and Compositions for Nucleic Acid Sample Preparation," the full disclosures of each of which are incorporated herein by reference in their entirety for all purposes.

Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

The nucleic acids can comprise a population of nucleic acids having universal sequence regions that are common to all of the nucleic acids in the population and also have specific regions that are different in the different members of the population. The current invention allows for capturing and isolating polymerase-nucleic acid complexes using either the universal or the specific regions.

While in many cases nucleic acid synthesis is describe herein as extending from a primer, it is to be understood that some polymerases do not require an added external primer, and can be initiated using terminal protein. Polymerases that can be initiated using terminal protein include phi-29 polymerase.

Polymerase Enzymes

Polymerase enzymes useful in this invention can include any suitable nucleic acid polymerase. Types of polymerases that can be used are described in more detail herein.

DNA Polymerases

DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y) which are incorporated by reference herein for all purposes. For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398, which are incorporated by reference herein for all purposes. The basic mechanisms of action for many polymerases have been determined. The sequences of literally hundreds of polymerases are publicly available, and the crystal structures for many of these have been determined, or can be inferred based upon similarity to solved crystal structures of homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296) which are incorporated by reference herein for all purposes. In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584, 481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. Pat. No. 9,127,259 entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.) which are incorporated by reference herein for all purposes. Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, *E. coli* DNA Polymerase 1, Klenow fragment, reverse transcriptases, Φ29-related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204 which are incorporated by reference herein for all purposes. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases are described, for example, in U.S. Pat. Nos. 8,420,366 and 8,257,954 which are each incorporated by reference herein for all purposes.

Polymerase enzymes useful in the invention include polymerases mutated to have desirable properties for sequencing. For example, suitable enzymes include those taught in, e.g., 61/593,569 filed Feb. 1, 2012 Recombinant Polymerases with Increased Phototolerance; U.S. Pat. No. 8,999, 676 entitled "Recombinant Polymerases for Improved Single Molecule Sequencing"; U.S. Pat. No. 9,127,29 entitled "Enzymes Resistant to Photodamage"; U.S. Pat. No. 8,420,366 entitled "Generation of Modified Polymerases for Improved Accuracy in Single Molecule Sequencing"; U.S. Pat. No. 8,257,954 entitled "Generation of Modified Polymerases for Improved Accuracy in Single Molecule Sequencing"; U.S. Pat. No. 8,343,746 entitled "Polymerase enzymes and reagents for enhanced nucleic acid sequencing"; US 20110059505 entitled "Polymerases for Nucleotide Analogue Incorporation"; and U.S. Provisional Patent No. 61/708,469 filed Oct. 1, 2012, all of which are incorporated by reference herein for all purposes. The modified polymerases can have modified properties such as e.g., decreased branch fraction formation, improved specificity, improved processivity, altered rates, improved retention time, improved stability of the closed complex, etc.

In addition, the polymerases can be further modified for application-specific reasons, such as to increase photostability, e.g., as taught in U.S. Pat. No. 9,127,259 entitled "Enzymes Resistant to Photodamage," to improve activity of the enzyme when bound to a surface, as taught, e.g., in WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al., or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. Pat. No. 8,133,672 entitled "Two slow-step polymerase enzyme systems and methods," incorporated herein by reference in its entirety for all purposes.

The polymerase enzymes used in the invention will generally have strand-displacement activity. Many polymerases have this capability, and it is useful in the context of the current invention for opening up and exposing the regions of a nucleic acid sample for capture by a hook molecule. In some cases, strand displacement is part of the polymerase enzyme itself. In other cases, other cofactors or co-enzymes can be added to provide the strand displacement capability.

RNA Dependent RNA Polymerases

In some embodiments, the polymerase enzyme that is used for sequencing is an RNA polymerase. Any suitable RNA polymerase (RNAP) can be used including RNA polymerases from bacteria, eukaryotes, viruses, or archea. Suitable RNA polymerases include RNA Pol I, RNA Pol II, RNA Pol III, RNA Pol IV, RNA Pol V, T7 RNA polymerase, T3 RNA polymerase or SP6 RNA polymerase. The use of RNA polymerases allows for the direct sequencing of messenger RNA, transfer RNA, non-coding RNA, ribosomal RNA, micro RNA or catalytic RNA. Where RNA polymerases are used, the polymerizing reagents will generally include NTPs or their analogs rather than the dNTPs used for DNA synthesis. In addition, RNA polymerases can be used with specific cofactors. There are many proteins that can bind to RNAP and modify its behavior. For instance, GreA and GreB from *E. coli* and in most other prokaryotes can enhance the ability of RNAP to cleave the RNA template near the growing end of the chain. This cleavage can rescue a stalled polymerase molecule, and is likely involved in proofreading the occasional mistakes made by RNAP. A separate cofactor, Mfd, is involved in transcription-coupled repair, the process in which RNAP recognizes damaged bases in the DNA template and recruits enzymes to restore the DNA. Other cofactors are known to play regulatory roles; i.e., they help RNAP choose whether or not to express certain genes. RNA dependent RNA polymerases (RNA replicases) may also be used including viral RNA polymerases: e.g. polioviral 3Dpol, vesicular stomatitis virus L, and hepatitis C virus NS5b protein; and eukaryotic RNA replicases which are known to amplify microRNAs and small temporal RNAs and produce double-stranded RNA using small interfering RNAs as primers.

Reverse Transcriptases

The polymerase enzyme used in the methods or compositions of the invention includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Thus, any suitable polymerase enzyme can be used in the systems and methods of the invention. Suitable polymerases include DNA dependent DNA polymerases, DNA dependent RNA polymerases, RNA dependent DNA polymerases (reverse transcriptases), and RNA dependent RNA polymerases.

Immobilization of the Polymerase-Template Complex

The polymerase-template complex can be attached to a surface such as to the channel of the nano-electronic measurement devices or to a region of the substrate proximate to the channel of the nano-electronic measurement devices. Such attachment is typically by binding the polymerase itself, but in some cases can be accomplished by binding the template nucleic acid, or a primer. The binding can be either covalent or non-covalent. In some cases, covalent attachment, for example, covalent attachment to a carbon nanotube is preferred. It is known that in some cases such covalent attachment can result to a single-walled carbon nanotube can result in an enhanced ability to detect molecular changes near the point of covalent attachment. See for example US20130285680, which is incorporated herein by reference. In some cases, a $SiO_2$ region of the surface can be selectively functionalized to bind the polymerase complex. The selective functionalization of $SiO_2$ can be carried out, for example, using silane chemistry. For example, the $SiO_2$ portion of the surface can be selectively treated with a biotin functionalized silane, and the surface can be treated with an enzyme complex attached to streptavidin. The streptavidin-polymerase-template complex will bind specifically to the biotin on the $SiO_2$ portions of the surface providing selective binding. See e.g. U.S. Pat. No. 8,193,123 which is incorporated herein by reference for all purposes. In some cases, small regions, e.g. balls, islands, or pits can be made on the surface that allow only a small number, and in some cases allow only a single polymerase enzyme to bind. The creation of regions to bind a single polymerase enzyme complex are described, for example in U.S. Pat. No. 8,906,831 entitled "Single Molecule Loading Methods and Compositions"; and U.S. Patent Application 20110257040 entitled "Nanoscale Apertures Having Islands of Functionality" which are incorporated herein by reference for all purposes. DNA molecules typically possess a strong negative charge and can thus be directed using electric fields in aqueous solution. Because the devices of the instant invention contemplate arrays of electrodes with means of applying electric potentials and concurrently measuring currents from proximate labels, the capability exists to use the potential-setting capacity to attract polymerases bound to DNA molecules to the electrode region and then either concurrently or in alternating periods check to see if a polymerase has bound the channel of a nano-electronic measurement devices. In this way each active nano-electronic measurement device can be loaded with a single polymerase by ceasing the attractive potential when the binding of a DNA-polymerase complex is detected.

The immobilization of a component of an analytical reaction can be engineered in various ways. For example, an enzyme (e.g., polymerase, reverse transcriptase, kinase, etc.) may be attached to the substrate at a reaction site, e.g., proximate to a nanoscale electrode. In other embodiments, a substrate in an analytical reaction (for example, a nucleic acid template, e.g., DNA, RNA, or hybrids, analogs, and mimetics thereof, or a target molecule for a kinase) may be attached to the substrate at a reaction site. Certain embodiments of template immobilization are provided, e.g., in U.S. Pat. No. 8,481,264 and incorporated herein by reference in its entirety for all purposes. One skilled in the art will appreciate that there are many ways of immobilizing nucleic acids and proteins, whether covalently or non-covalently, via a linker moiety, or tethering them to an immobilized moiety. These methods are well known in the field of solid phase synthesis and micro-arrays (Beier et al., Nucleic Acids Res. 27:1970-1-977 (1999)). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, hydrazone linkages, among others. Antibodies that specifically bind to one or more reaction components can also be employed as the binding moieties. In addition, a silyl moiety can be attached to a nucleic acid directly to a substrate such as glass using methods known in the art.

In some embodiments, a nucleic acid template is immobilized onto a reaction site (e.g., proximate to a channel of a nano-electronic measurement devices) by attaching a primer comprising a complementary region at the reaction site that is capable of hybridizing with the template, thereby immobilizing it in a position suitable for monitoring. In certain embodiments, an enzyme complex is assembled, e.g., by first immobilizing an enzyme component. In other embodiments, an enzyme complex is assembled in solution prior to immobilization. Where desired, an enzyme or other protein reaction component to be immobilized may be modified to contain one or more epitopes for which specific antibodies are commercially available. In addition, proteins can be modified to contain heterologous domains such as glutathione S-transferase (GST), maltose-binding protein (MBP), specific binding peptide regions (see e.g., U.S. Pat. Nos. 5,723,584, 5,874,239 and 5,932,433), or the Fc portion of an immunoglobulin. The respective binding agents for these domains, namely glutathione, maltose, and antibodies directed to the Fc portion of an immunoglobulin, are available and can be used to coat the surface of a device of the present invention. The binding moieties or agents of the reaction components they immobilize can be applied to a support by conventional chemical techniques which are well known in the art. In general, these procedures can involve standard chemical surface modifications of a support, incubation of the support at different temperature levels in different media comprising the binding moieties or agents, and possible subsequent steps of washing and cleaning.

The various components of the surface of the devices can be selectively treated in order to bind the polymerase-template complex to a specific portion of the substrate. Selective treatment and immobilization is described, for example, in U.S. Pat. No. 5,624,711; U.S. Pat. No. 5,919, 523; Hong et al., (2003) Langmuir 2357-2365; U.S. Pat. No. 5,143,854; U.S. Pat. No. 5,424,186; U.S. Pat. No. 8,137,942; U.S. Pat. No. 7,993,891 Reactive surfaces, substrates and methods of producing and using same; U.S. Pat. No. 7,935, 310; U.S. Pat. No. 7,932,035 U.S. Pat. No. 7,931,867 entitled "Uniform surfaces for hybrid material substrates and methods of making and using same"; and U.S. Pat. No. 8,193,123 "Articles having localized molecules disposed thereon and methods of producing same", all of which are incorporated herein by reference for all purposes.

The polymerase complex is typically attached directly to the channel of the nanoFET (e.g. the nanowire or carbon nanotube), but in some cases the polymerase complex is attached proximate to the gate. Such an attachment is made close enough to the nano-electronic measurement device that the charge label on a nucleotide analog held in the active site of the enzyme can extend close enough to the channel of the nano-electronic measurement device to allow for detection. The polymerase complex can be attached for example from about 1 nm to about 100 nm from the channel of a nano-electronic measurement devices, from about 2 nm to about 50 nm from the channel of a nano-electronic measurement devices, or from about 4 nm to about 20 nm from the channel of a nano-electronic measurement devices.

Conditions for Nucleic Acid Synthesis

The conditions required for nucleic acid synthesis are well known in the art. The polymerase reaction conditions include the type and concentration of buffer, the pH of the reaction, the temperature, the type and concentration of salts, the presence of particular additives that influence the kinetics of the enzyme, and the type, concentration, and relative amounts of various cofactors, including metal cofactors. For carrying out the methods of the instant invention, the conditions for polymerase mediated nucleic acid synthesis must also be compatible with conditions for measuring electrical signals at the nano-electronic measurement device. One aspect of carrying out electrical measurements in solution is controlling the ionic strength of the medium. It is know that polymerase enzymes can effectively operate over a range of ionic strengths, and that the ionic strength can be varied by changing the levels of monovalent ions such as Li+, Na+, K+, Rb+, or Cs+. As has been shown, the amount of one or more of these cations can have an effect on the kinetics of the polymerase, and that the kinetic behavior can be tuned by varying the relative amounts of these ions. Using combinations of these ions, conditions can be chosen where both the kinetic parameters of the enzyme, and the ionic strength for electrical detection can be useful for the instant methods.

See, e.g. U.S. Pat. No. 8,986,930 which is incorporated herein by reference for all purposes.

Enzymatic reactions are often run in the presence of a buffer, which is used, in part, to control the pH of the reaction mixture. Buffers suitable for the invention include, for example, TAPS (3-{[tris(hydroxymethyl)methyl] amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the rate of the polymerase reaction. The temperature of the reaction can be adjusted to enhance the performance of the system. The reaction temperature may depend upon the type of polymerase which is employed.

Nucleotide Analogs

Components of the sequencing reaction mixture include nucleotides or nucleotide analogs. For the methods of the instant invention, at least some of the nucleotide analogs have charge labels attached to them. The nucleotide analogs comprising charge labels are generally constructed in order to enhance the electrical signal at the nano-electronic measurement device when the label is in the enzyme active site.

Typically the nucleotide analogs of the invention have the following structure: Base-Sugar-PP-Linker-Label.

In some embodiments, the Base is a nucleobase, Sugar is a sugar such as ribose or deoxyribose, PP is a polyphosphate moiety, Linker is a linking group, and the Label is a group that is detectable by the nano-electronic measurement device. The label can be for example, a charge label as described herein.

Typically there are four nucleotides in a sequencing reaction mixture corresponding to A, G, T, and C for DNA and A, G, C, U for RNA. In some cases, a $5^{th}$, $6^{th}$, or more base is included. In some cases all of the nucleotide analogs have a charge label, in other cases, fewer than all of the nucleotides will have a charge label. In still other cases all of the different nucleotide analog types will carry a charge label, but a particular charge label will be assigned to more than one base type. Typically each of the types of nucleotide will have a nucleotide that is different and can be distinguished from the other nucleotides, for example the other three nucleotides. As described herein, the different nucleotides can exhibit different impedance intensities, different impedance versus frequency characteristics, different current versus time characteristics (current oscillation color), or different combinations of two or more of the above.

The Base is a nucleobase which can be one of the natural bases, a modified natural base or a synthetic base. The Base will selectively associate with its complementary base on the template nucleic acid such that it will be inserted across from its complementary base. The Sugar is a group that connects the base to the polyphosphate group. It is typically either ribose or deoxyribose, but can be any sugar or other group that allows for the complexation and incorporation of the nucleotide analog into the growing strand. PP is a polyphosphate group generally from 2 to 20 phosphates in length, typically from 3 to 12 phosphates in length, and in some preferred embodiments from 4 to 10 phosphates in length. The nucleotide analog can have for example 4, 5, 6, 7 or more phosphate groups. Such nucleotides have been described, for example, in U.S. Pat. Nos. 6,936,702 and 7,041,812, which are incorporated herein by reference for all purposes. Together, the Base, Sugar and PP portion of the nucleotide analog is sometimes referred to as the nucleotide portion or nucleoside phosphate portion.

As used in the art, the term nucleotide refers both to the nucleoside triphosphates that are added to a growing nucleic acid chain in the polymerase reaction, or can refer to the individual units of a nucleic acid molecule, for example the units of DNA and RNA. Herein, the term nucleotide is used consistently with its use in the art. Whether the term nucleotide refers to the substrate molecule to be added to the growing nucleic acid or to the units in the nucleic acid chain can be derived from the context in which the term is used.

The Linker is a linking group that connects the label to the nucleotide portion of the nucleotide analog. The linker can be long linear or branched moiety whose length and flexibility is used to control the diffusion of the nucleotide analog that is held within the polymerase enzyme while it is being incorporated. The length of the Linker is, for example, from between 2 nm and 200 nm when fully extended. It is understood that a long molecule such as a polymer will not spend much time, if any, in its fully extended configuration. The Linker can be made up of groups including alkanes, ethers, alcohols, amines, acids, sulfates, sulfonates, phosphates, phosphonates, amides, esters, peptides, and sugars. The groups on the Linker can be neutral, positively charged, or negatively charged. In some cases, the Linker comprises polyethylene glycol (PEG). It is desirable that the Linker have a fixed length (i.e. not be polydisperse) such that the size of any analog molecule in the population will be the same. It is generally desirable that the linker be water compatible. In some cases the Linker can include one or more macromolecules, such as proteins, or one or more nanoparticles.

In some, the covalent attachment site is far from the active site, but the Linker is long, e.g., more than 5 nm, or more than 10 nm or more than 20 nm, allowing the active site to spend some amount of time in proximity to the detection zone. When a long Linker is used, rotational freedom of the polymerase permits the active site to enter the detection zone of the nanotube. In one preferred example of this method, a covalent attachment is provide at a location on the enzyme surface that is convenient (for example the c or n terminus) and an affinity label is engineered into a residue near the active site (375, 512 or near as before) to bias the orientation. This strategy provides a degree of freedom in the construction of the enzyme.

The length or size of the Linker can be chosen for performance with the particular geometry of the nano-electronic measurement device that is used. The charge label is tethered to the nucleotide analog (comprising the Linker), the enzyme and the attachment moiety. The length of this complete tether and the distance of the polymerase complex from the nano-electronic measurement device (e.g., from the channel of the device) can be used in order to select the appropriate Linker.

The charge label is attached to the nucleotide portion of the nucleotide analog through the Linker and phosphate. The Linker is typically attached to the terminal phosphate in the polyphosphate moiety, but in some cases can be connected to a phosphate in the polyphosphate chain that is not the terminal phosphate. The Linker is typically attached to a phosphate that is cleaved on the act of the polymerase enzyme of nucleotide incorporation. The polymerase enzyme cleaves the polyphosphate between the alpha and beta phosphates, thus, the Linker should be connected to the beta (second) phosphate or greater.

The impedance label may be made up of one or more moieties that provide a measurable electrical signal by the nano-electronic measurement device. Acceptable labels or moieties can comprise organic compounds, organometallic compounds, nanoparticles, metals, or other suitable substituent.

Kinetic Measurements—Modified Base Detection

The methods of the invention provide for measuring the incorporation of nucleotides into a growing chain in real time. The real time measurements allow for the determination of enzyme kinetics, which are can be sensitive to template characteristics such as secondary structure, and modified bases. The ability to detect modifications within nucleic acid sequences is useful for mapping such modifications in various types and/or sets of nucleic acid sequences, e.g., across a set of mRNA transcripts, across a chromosomal region of interest, or across an entire genome. The modifications so mapped can then be related to transcriptional activity, secondary structure of the nucleic acid, siRNA activity, mRNA translation dynamics, kinetics and/or affinities of DNA- and RNA-binding proteins, and other aspects of nucleic acid (e.g., DNA and/or RNA) metabolism.

In certain aspects of the invention, methods are provided for identification of a modification in a nucleic acid molecule using real time nanoFET sequencing. In general, a template nucleic acid comprising the modification and an enzyme capable of processing the template are provided. The template nucleic acid is contacted with the enzyme, and the subsequent processing of the template by the enzyme is monitored. A change in the processing is detected, and this change is indicative of the presence of the modification in the template. Exemplary modifications that can be detected by the methods of the invention include, but are not limited to methylated bases (e.g., 5-methylcytosine, N6-methyladenosine, etc.), pseudouridine bases, 7,8-dihydro-8-oxoguanine bases, 2'-O-methyl derivative bases, nicks, apurinic sites, apyrimidic sites, pyrimidine dimers, a cis-platen crosslinking products, oxidation damage, hydrolysis damage, bulky base adducts, thymine dimers, photochemistry reaction products, interstrand crosslinking products, mismatched bases, secondary structures, and bound agents. In preferred embodiments, nucleotides or analogs thereof that are incorporated into a nascent strand synthesized by the enzyme are distinctly labeled to allow identification of a sequence of specific nucleotides or nucleotide analogs so incorporated. Labels are linked to nucleotides or nucleotide analogs through a phosphate group, e.g., a phosphate group other than the alpha phosphate group. As such, the labels are removed from the nucleotide or nucleotide analog upon incorporation into the nascent strand. Techniques for kinetically identifying modified bases are described, for example in U.S. Pat. No. 9,175,338 entitled "Methods for Identifying Nucleic Acid Modifications" which is incorporated herein by reference for all purposes.

The term "modification" as used herein is intended to refer not only to a chemical modification of a nucleic acids, but also to a variation in nucleic acid conformation or composition, interaction of an agent with a nucleic acid (e.g., bound to the nucleic acid), and other perturbations associated with the nucleic acid. As such, a location or position of a modification is a locus (e.g., a single nucleotide or multiple contiguous or noncontiguous nucleotides) at which such modification occurs within the nucleic acid. For a double-stranded template, such a modification may occur in the strand complementary to a nascent strand synthesized by a polymerase processing the template, or may occur in the displaced strand. Although certain specific embodiments of the invention are described in terms of 5-methylcytosine detection, detection of other types of modified nucleotides (e.g., $N^6$-methyladenosine, $N^3$-methyladenosine, $N^7$-methylguanosine, 5-hydroxymethylcytosine, other methylated nucleotides, pseudouridine, thiouridine, isoguanosine, isocytosine, dihydrouridine, queuosine, wyosine, inosine, triazole, diaminopurine, β-D-glucopyranosyloxymethyluracil (a.k.a., β-D-glucosyl-HOMedU, β-glucosyl-hydroxymethyluracil, "dJ," or "base J"), 8-oxoguanosine, and 2'-O-methyl derivatives of adenosine, cytidine, guanosine, and uridine) are also contemplated. Further, although described primarily in terms of DNA templates, such modified bases can be modified RNA bases and can be detected in RNA (or primarily RNA) templates. These and other modifications are known to those of ordinary skill in the art and are further described, e.g., in Narayan P, et al. (1987) Mol Cell Biol 7(4):1572-5; Horowitz S, et al. (1984) Proc Natl Acad Sci U.S.A. 81(18):5667-71; "RNA's Outfits: The nucleic acid has dozens of chemical costumes," (2009) C&EN; 87(36): 65-68; Kriaucionis, et al. (2009) Science 324 (5929): 929-30; and Tahiliani, et al. (2009) Science 324 (5929): 930-35; Matray, et al. (1999) Nature 399(6737):704-8; Ooi, et al. (2008) Cell 133: 1145-8; Petersson, et al. (2005) J Am Chem Soc. 127(5):1424-30; Johnson, et al. (2004) 32(6):1937-41; Kimoto, et al. (2007) Nucleic Acids Res. 35(16):5360-9; Ahle, et al. (2005) Nucleic Acids Res 33(10):3176; Krueger, et al., Curr Opinions in Chem Biology 2007, 11(6):588); Krueger, et al. (2009) Chemistry & Biology 16(3):242; McCullough, et al. (1999) Annual Rev of Biochem 68:255; Liu, et al. (2003) Science 302(5646):868-71; Limbach, et al. (1994) Nucl. Acids Res. 22(12):2183-2196; Wyatt, et al. (1953) Biochem. J. 55:774-782; Josse, et al. (1962) J. Biol. Chem. 237:1968-1976; Lariviere, et al. (2004) J. Biol. Chem. 279:34715-34720; and in International Application Publication No. WO/2009/037473, the disclosures of which are incorporated herein by reference in their entireties for all purposes. Modifications further include the presence of non-natural base pairs in the template nucleic acid, including but not limited to hydroxypyridone and pyridopurine homo- and hetero-base pairs, pyridine-2,6-dicarboxylate and pyridine metallo-base pairs, pyridine-2,6-dicarboxamide and a pyridine metallo-base pairs, metal-mediated pyrimidine base pairs T-Hg(II)-T and C-Ag(I)-C, and metallo-homobasepairs of 2,6-bis(ethylthiomethyl)pyridine nucleobases Spy, and alkyne-, enamine-, alcohol-, imidazole-, guanidine-, and pyridyl-substitutions to the purine or pyridimine base (Wettig, et al. (2003) J Inorg Biochem 94:94-99; Clever, et al. (2005) Angew Chem Int Ed 117:7370-7374; Schlegel, et al. (2009) Org Biomol Chem 7(3):476-82; Zimmerman, et al. (2004) Bioorg Chem 32(1):13-25; Yanagida, et al. (2007) Nucleic Acids Symp Ser (Oxf) 51:179-80; Zimmerman (2002) J Am Chem Soc 124(46): 13684-5; Buncel, et al. (1985) Inorg Biochem 25:61-73; Ono, et al. (2004) Angew Chem 43:4300-4302; Lee, et al. (1993) Biochem Cell Biol 71:162-168; Loakes, et al. (2009), Chem Commun 4619-4631; and Seo, et al. (2009) J Am Chem Soc 131:3246-3252, all incorporated herein by reference in their entireties for all purposes). Other types of modifications include, e.g, a nick, a missing base (e.g., apurinic or apyridinic sites), a ribonucleoside (or modified ribonucleoside) within a deoxyribonucleoside-based nucleic acid, a deoxyribonucleoside (or modified deoxyribonucleoside) within a ribonucleoside-based nucleic acid, a pyrimidine dimer (e.g., thymine dimer or cyclobutane pyrimidine dimer), a cis-platin crosslinking, oxidation damage, hydrolysis damage, other methylated bases, bulky DNA or RNA base adducts, photochemistry reaction products, interstrand crosslinking products, mismatched bases, and other types of "damage" to the nucleic acid. As such, certain embodiments described herein refer to "damage" and such damage is also considered a modification of the nucleic acid in accordance with the present invention. Modified nucleotides can be caused by exposure of the DNA to radiation (e.g., UV), carcinogenic chemicals, crosslinking agents (e.g., formaldehyde), certain enzymes (e.g., nickases, glycosylases, exonucleases, methylases, other nucleases, glucosyltransferases, etc.), viruses, toxins and other chemicals, thermal disruptions, and the like. In vivo, DNA damage is a major source of mutations leading to various diseases including cancer, cardiovascular disease, and nervous system diseases (see, e.g., Lindahl, T. (1993) Nature 362(6422): 709-15, which is incorporated herein by reference in its entirety for all purposes). The methods and systems provided herein can also be used to detect various conformations of DNA, in particular, secondary structure forms such as hairpin loops, stem-loops, internal loops, bulges, pseudoknots, base-triples, supercoiling, internal hybridization, and the like; and are also useful for detection of agents interacting with the nucleic acid, e.g., bound proteins or other moieties.

In some embodiments, five color DNA sequencing can be carried out by the sequencing methods of the invention. Five color sequencing generally utilizes a nucleotide analog having a base that preferentially associates with a fifth base in the template or an abasic site. Such five color sequencing is described for example in U.S. Pat. No. 9,175,338, which is incorporated herein by reference in its entirety for all purposes.

It will be apparent to the ordinary artisan that although various strategies herein are described independently, they can also be used in combination in certain embodiments. For example, as noted above, a strategy for extend the zone of sensitivity to the charge of interest can be combined with a strategy for bringing the charge of interest to the nanowire. Further, an embodiment can include a reference nanowire as well as an attachment that positions an active site of a polymerase proximal to a nanowire. Different types of charge labels can be combined with different types of protein immobilization strategies. As such, combinations of the strategies are contemplated and within the scope of the invention.

Monitoring Biological Reactions

While the nanoscale devices and systems of the invention are described throughout most of this application for use in nucleic acid sequencing, it is to be understood that the devices and systems can also find use in other analytical reactions including monitoring biological reactions in real time, in particular monitoring the interactions of biological molecules at the single molecule level. The ability to analyze such reactions provides an opportunity to study those reactions as well as to potentially identify factors and/or approaches for impacting such reactions, e.g., to stimulate, enhance, or inhibit such reactions.

The invention provides for observation of the interaction of two or more specifically interacting reactants at the single molecule (or single molecular complex) level in order to monitor the progress of the interaction separately from other interactions. In other words, a single immobilized reaction component can be monitored at a single reaction site on a support such that electrical signals received from that reaction site are resolvable from other immobilized reaction components at other reaction sites on that support. In preferred embodiments, the methods monitor charge labels with a nano-electronic measurement devices, such that a single reactant comprising a label is distinguishable from a different single reactant comprising a different label. A plurality of analytical reactions may also be carried out in an array of nano-electronic measurement devices. Analytical reactions in an array of nano-electronic measurement devices can be carried out concurrently, and may or may not be synchronized with one another. In such an array, multiple reactions can therefore be monitored simultaneously and independently.

The monitoring typically comprises providing the interaction with one or more signaling events that are indicative of one or more characteristics of that interaction. Such signaling events may comprise the retention of a labeled reactant proximate to a given nano-electronic measurement device. For example, in some embodiments, the charge labels provide electrical signals that are detected by a detection system operably linked to a reaction site at which the analytical reaction is taking place. As used herein, a reaction site is a location on or adjacent to a substrate at which an analytical reaction is monitored, and may refer to, e.g., a position on the substrate at which one or more components of an analytical reaction are immobilized or to a "detection volume" within which an analytical reaction is monitored. The detected signals are analyzed to determine one or more characteristics of the analytical reaction, e.g., initiation, termination, affinity, biochemical event (e.g., binding, bond cleavage, conformational change, etc.), substrate utilization, product formation, kinetics of the reaction (e.g., rate, time between subsequent biochemical events, time between the beginning/end of subsequent biochemical events, processivity, error profile, etc.), and the like.

These characteristics may generally be broken into two categories: reactant characteristic(s) and interaction characteristic(s). Reactant characteristic(s) includes characteristics of a particular reactant, e.g., type/identity of reactant, concentration of the reactant, a label on the reactant, etc. Interaction characteristic(s) includes characteristics of a given interaction between multiple reactants, e.g., rates, constants, affinities, etc., and is typically determined based on reaction data gathered during such an interaction. For example, some characteristics of a polymerization reaction include the identity of a monomer incorporated into a growing polymer, the rate of incorporation, length of time the polymerase is associated with the template, and the length of the polymer synthesized. In some embodiments, various different components of an analytical reaction (e.g., different types of monomers) are differentially labeled to allow each labeled component to be distinguished from other labeled components during the course of the reaction. For example, incorporation of monomer A into a polymer can be distinguished from incorporation of monomer B.

In certain preferred embodiments, multiple characteristics of a reaction are monitored and/or determined. For example, these may be multiple characteristics of one or more reaction components (e.g., identity, concentration, etc.; "reactant characteristic(s)"), one or more characteristics of an interaction between two or more reaction components (e.g., related to product formation, kinetics of the reaction, binding or dissociation constants, etc.; "interaction characteristic(s)"), or, preferably, a combination reactant characteristic(s) and interaction characteristic(s).

In some embodiments, a reaction mixture comprises a plurality of types of non-immobilized binding partners, and a characteristic determined is the particular type of one of the non-immobilized binding partners, e.g., that associates with a particular reaction site. Typically, the charge label is attached to the non-immobilized binding partner through a linking group as described herein such that the label on the non-immobilized binding partner will be sensed when it is interacting with the immobilized binding partner that is immobilized proximate to a nanoscale electrode or electrodes. In some embodiments, an array of reaction sites comprises a plurality of types of immobilized binding partners, each at a different reaction site, and a characteristic is determined that identifies which type of immobilized binding partner is located at each of the different reaction sites. In some embodiments, an array of reaction sites comprising a plurality of types of immobilized binding partners, each at a different reaction site, is contacted with a reaction mixture comprising a plurality of types of non-immobilized binding partners; characteristics determined during the reaction serve to both identify which of the types of immobilized binding partners is located at each reaction site and which of the types of non-immobilized binding partners associate with the immobilized binding partners. In some cases, the specificity of the interaction between the non-immobilized and immobilized binding partners is high enough that detection of a label on a non-immobilized binding partner residing at a particular reaction site is sufficient to identify the immobilized binding partner at that reaction site. In some embodiments, a characteristic is determined that quantifies a particular aspect of an interaction between reaction components, e.g., affinity between an immobilized binding partner and a non-immobilized binding partner, a rate of catalysis of a reaction, or other aspects of the interaction. In some cases, different electronic signaling events (e.g., different labels on one or more reaction components) are used to monitor or determine different characteristics of a reaction under observation, but in some embodiments a single electrical signaling event can provide more than one type of characteristic information. For example, if a non-immobilized binding partner has a label that not only identifies it from a plurality of different non-immobilized binding partners, but also provides kinetic information about the reaction based on various parameters monitored in real time, e.g., the time it takes for binding to occur, the time it remains associated with the reaction site, the on/off rate, etc.

In some embodiments, multiple different interactions or reactions can occur and be monitored concurrently or sequentially, where each individual interaction is monitored separately from every other, e.g. in an electronic element such as a nanoFET, such that there is resolution between different interactions under observation. For example, multiple different non-immobilized reaction components may concurrently or sequentially interact with an immobilized reaction component; e.g., the multiple different non-immobilized reaction components can be different non-immobilized binding partners for an immobilized binding partner, or different agents that may alter an interaction between two reaction components, or different monomers for incorporation into a polymer being synthesized at the reaction site. In other embodiments, an interaction between a non-immobilized reaction component and a product of a synthesis reaction occurs during the synthesis reaction, e.g., once the product is suitable for such interaction. For example, the product may need to be of a certain length, or in a certain conformation (e.g., in a particular higher-order structure) to be suitable for interaction with the non-immobilized reaction component. Alternatively, a synthesis reaction can be performed at a reaction site, and subsequently exposed to a reaction mixture comprising non-immobilized reaction components that can then interact with the product of the synthesis reaction, which is preferably immobilized at the reaction site. In preferred embodiments, the synthesis reaction is monitored to determine characteristics of the product (e.g., length, chemical composition, etc.) being synthesized. Knowledge of characteristics of the product of synthesis combined with the detection of an interaction with a particular reaction component provides additional characteristics, e.g., the binding site for the particular reaction component. Examples of biological interactions that can be measured with the nanoFET devices and systems of the invention are described, for example, in U.S. Pat. No. 9,063,156 entitled "Real-Time Analytical Methods and Systems" which is incorporated herein by reference for all purposes.

Systems

In some aspects, the invention provides systems for carrying out real time single molecule electronic sequencing using nano-electronic measurement devices. A nano-electronic measurement device measuring system is used to monitor the nano-electronic measurement device over time, allowing for the determination of whether a nucleotide analog having a charge label is associating with the enzyme. That is, the nano-electronic measurement device element and enzyme are configured such that the freely diffusing charge labeled nucleotide analogs in the solution are not substantially detected at the nano-electronic measurement device. Only when a charge label is brought into the vicinity of the nano-electronic measurement device due to its association with the polymerase enzyme is the charge label detected and identified as an incorporated nucleotide. One distinction between the freely diffusing nucleotide analogs and an analog in the active site of the enzyme is the amount of time spent proximate to the nano-electronic measurement device. Diffusing nucleotide analogs will be quickly diffusing in and out of the vicinity of the nanoscale electrode, while the nucleotide analog to be incorporated will spend a longer amount of time, for example on the order of milliseconds proximate to the nanoscale electrode. Thus, the nano-electronic measurement device measuring system will detect the presence of a nucleotide analog which is to be incorporated into the growing nucleic acid chain while it is in the active site of the enzyme. When the nucleotide is incorporated into the growing strand, the label, which is attached to the phosphate portion of the nucleotide analog is cleaved and diffuses away from the enzyme and the electrode. Thus, the system determines the presence of the analog in the active site prior to incorporation. In addition, the identity of the distinct label is determined, e.g. by the magnitude of a change in an electrical property at the gate of the electrode. As the polymerase reaction continues and is monitored by the nano-electronic measurement device measuring system, the sequence of the template nucleic acid can be determined by the time sequence of incorporation of the complementary nucleotide analog into the growing nucleic acid strand.

The systems of the invention include a chip comprising an array of nano-electronic measurement devices as described herein that is reversibly mated with other system components. The chip with an array of nano-electronic measurement devices can be a single use chip or the chip can be used multiple times. The system typically has a housing into which the chip is placed. The housing has electrical connectors that provide reversible connections to the electrical connections on the chip. Sockets that provide reliable reversible electrical connections to chips inserted into the socket are well known. Electrical connections to the top, sides, bottom, or a combination of these sides can be used.

When the chip is inserted into the housing, the system provides a fluid reservoir to which fluid comprising the sequencing reaction mixture is added. In some cases, the fluid reservoir is included as part of the chip. In some cases, part of the fluid reservoir is associated with the housing, such that the insertion of the chip forms the reservoir. The fluid reservoir can be, for example a well or a chamber into which fluid can be introduced. The introduced fluid sequencing reaction mixture comes into contact with the nanoFET devices on the surface of the chip. The system will typically include environmental control components including temperature control and control of a vapor phase above the fluid. The chemical makeup and the temperature of the vapor can be controlled, for example by providing a flow of inert gas over the reaction mixture to minimize oxidation of the sample. In some cases the system can have fluid handling systems for delivering and removing components to the fluid reservoir before, during, or after performing the sequencing reaction.

In some cases the fluid reservoir will also provide contact of the sequencing reaction mixture with the either or both of a reference electrode or counter electrode. As described above, in order to carry out the method, in some cases a reference electrode, a counter electrode, or both are used. In some one or more of these electrodes are on the chip. Where the reference electrode and/or counter electrode are used, and not on the chip, they are brought into contact with the sequencing reaction mixture in the fluid reservoir.

Connected to the chip through the connectors on the housing are the electronics for providing voltage to the nano-electronic measurement device and for measuring the electronic signals of the channels of the nano-electronic measurement devices, for example, a current/voltage source and a meter. For example, the source can provide the current and voltage to bring the electrodes to a proper alternating current signal over time to carry out the methods of the invention. The meter can be used to measure the electrical signals. In some cases, the source and meter are combined into a single unit. In some cases each of the electronic elements in the array on the chip are addressed by a separate source and separate meter component within the system. In some cases, multiplexing is used so a single source can drive multiple electronic elements. In some cases a single source will drive all of the electronic elements on a chip, while each of the electronic elements is measured with a separate meter component. Any suitable combination of sources and meters can be used.

A computer control and analysis system is typically used to control both the input voltages and currents and to provide computer-implemented control functions, e.g., controlling robotics, environmental conditions, and the state of various components of the system. The computer control system also includes components for computational data analysis (e.g., for single molecule sequencing applications, determining and characterizing nucleotide incorporation events). As described above, in some cases, some of the control functions can be implemented on the chip, in particular controlling source wave functions, or handling electrical signals from the nano-electronic measurement devices on the chip. In some cases the computer control and analysis system provides substantially all of the control of the signals to and from the chip, and the chip simple acts as an electronic element from which information related to the electronic signal is extracted. In some cases, the chip can take on some of the functionality of control and analysis. The chip can process the analog data from the electronic elements. The chip can also have analog to digital components, and can perform analysis and storage functions for the digital signals. The decision on how much functionality is implemented on the chip and how much is retained with the computer control and analysis system can be made based on the relative functionality gained versus the cost of adding the functionality.

Also provided is a user interface operatively coupled to the components for computational data, permitting a user of the system to initiate and terminate an analysis, control various parameters (e.g., with respect to analysis conditions, sequencing reaction mixture environment, etc.), and manage/receive data (e.g., nucleic acid sequence data) obtained by the system. In some aspects, the user interface is attached the computer control and analysis system. Additionally, remote user interfaces can be provided that are in communication with the overall system via a wireless network. Such user input devices may include other purposed devices, such as notepad computers, e.g., Apple iPad, or smartphones running a user interface application. Optionally, the user interface includes a component, e.g., a data port, from which the user can receive data obtained by the analysis system to a portable electronic storage medium for use at location other than the location of the substrate analysis system.

Aspects of the present invention are directed to machine or computer implemented processes, and/or software incorporated onto a computer readable medium instructing such processes. As such, signal data generated by the reactions and systems described above, is input or otherwise received into a computer or other data processor, and subjected to one or more of the various process steps or components set forth herein. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or MACINTOSH® type computers, to workstations, laboratory equipment, or high speed servers, running UNIX, LINUX, WINDOWS®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

The following documents provide teachings of various aspects of carrying out the instant invention. These documents are incorporated by reference herein in their entirety for all purposes.

1. Rosenblatt S, Yaish Y, Park J, Gore J, Sazonova V, McEuen P L. High performance electrolyte gated carbon nanotube transistors. Nano Letters. 2002; 2(8):869-72. doi: Doi 10.1021/N1025639a. PubMed PMID: ISI: 000177485500016.
2. Star A, Tu E, Niemann J, Gabriel J-C P, Joiner C S, Valcke C. Label-free detection of DNA hybridization using carbon nanotube network field-effect transistors. Proc Natl Acad Sci USA. 2006; 103(4):921-6. doi: 10.1073/pnas.0504146103.
3. Besteman K, Lee J-O, Wiertz F G M, Heering H A, Dekker C. Enzyme-Coated Carbon Nanotubes as Single-Molecule Biosensors. Nano Letters. 2003; 3(6):727-30. doi: 10.1021/nl034139u.
4. Heller I, Janssens A M, Mannik J, Minot E D, Lemay S G, Dekker C. Identifying the mechanism of biosensing with carbon nanotube transistors. Nano Letters. 2008; 8(2):591-5. Epub 2007/12/29. doi: 10.1021/nl072996i. PubMed PMID: 18162002.
5. Sorgenfrei S, Chiu C Y, Gonzalez R L, Yu Y J, Kim P, Nuckolls C, et al. Label-free single-molecule detection of DNA-hybridization kinetics with a carbon nanotube field-effect transistor. Nature Nanotechnology. 2011; 6(2):125-31. doi: 10.1038/nnano.2010.275. PubMed PMID: ISI: 000286968500015.
6. Goldsmith B R, Coroneus J G, Kane A A, Weiss G A, Collins P G. Monitoring Single-Molecule Reactivity on a Carbon Nanotube. Nano Letters. 2008; 8(1):189-94. doi: 10.1021/nl0724079.
7. Sorgenfrei S, Chiu C-y, Johnston M, Nuckolls C, Shepard K L. Debye Screening in Single-Molecule Carbon Nanotube Field-Effect Sensors. Nano Letters. 2011; 11(9): 3739-43. doi: 10.1021/nl201781q.
8. Goldsmith B R, Coroneus J G, Khalap V R, Kane A A, Weiss G A, Collins P G. Conductance-Controlled Point Functionalization of Single-Walled Carbon Nanotubes. Science. 2007; 315(5808):77-81. doi: 10.1126/science.1135303.
9. Rothberg J M, Hinz W, Rearick T M, Schultz J, Mileski W, Davey M, et al. An integrated semiconductor device enabling non-optical genome sequencing. Nature. 2011; 475(7356):348-52. doi:
10. Huang TcD, Sorgenfrei S, Gong P, Levicky R, Shepard K L. A 0.18-um CMOS Array Sensor for Integrated Time-Resolved Fluorescence Detection. Solid-State Circuits, IEEE Journal of 2009; 44(5):1644-54.
11. Huang T-C D, Paul S, Gong P, Levicky R, Kymissis J, Amundson S A, et al. Gene expression analysis with an integrated CMOS microarray by time-resolved fluorescence detection. Biosensors and Bioelectronics. 2011; 26(5):2660-5. doi: 10.1016/j.bios.2010.03.001.
12. Johnston M L, Kymissis I, Shepard K L. FBAR-CMOS Oscillator Array for Mass-Sensing Applications. Sensors Journal, IEEE. 2010; 10(6):1042-7.
13. Lei N, Ramakrishnan S, Shi P, Orcutt J S, Yuste R, Kam L C, et al. High-resolution extracellular stimulation of dispersed hippocampal culture with high-density CMOS multielectrode array based on non-Faradaic electrodes. Journal of neural engineering. 2011; 8(4):044003. Epub 2011/07/05. doi: 10.1088/1741-2560/8/4/044003. PubMed PMID: 21725154.
14. Levine P M, Gong P, Levicky R, Shepard K L. Real-time, multiplexed electrochemical DNA detection using an active complementary metal-oxide-semiconductor biosensor array with integrated sensor electronics. Biosensors and Bioelectronics. 2009; 24(7):1995-2001.
15. Levine P M, Ping G, Levicky R, Shepard K L. Active CMOS Sensor Array for Electrochemical Biomolecular Detection. Solid-State Circuits, IEEE Journal of. 2008; 43(8):1859-71.
16. Patounakis G, Shepard K L, Revicky R. Active CMOS array sensor for time-resolved fluorescence detection. IEEE Journal of Solid-State Circuits. 2006; 41(11):2521-30.
17. Rosenstein J K, Wanunu M, Merchant C A, Drndic M, Shepard K L. Integrated nanopore sensing platform with sub-microsecond temporal resolution. Nat Meth. 2012; 9(5):487-92.
18. Schwartz D, Gong P, Shepard K L. Time-resolved Forster-resonance-energy-transfer DNA assay on an active CMOS microarray. Biosensors and Bioelectronics. 2008; 24(3):383-90.
19. Bronson J E, Fei J, Hofman J M, Gonzalez Jr R L, Wiggins C H. Learning Rates and States from Biophysical Time Series: A Bayesian Approach to Model Selection and Single-Molecule FRET Data. Biophys J. 2009; 97(12):3196-205. doi: DOT: 10.1016/j.bpj 0.2009.09.031.
20. Fei J, Bronson J E, Hofman J M, Srinivas R L, Wiggins C H, Gonzalez R L. Allosteric collaboration between elongation factor G and the ribosomal L1 stalk directs tRNA movements during translation. Proceedings of the National Academy of Sciences. 2009; 106(37):15702-7. doi: 10.1073/pnas.0908077106.
21. Lu H P, Xun L, Xie X S. Single-Molecule Enzymatic Dynamics. Science. 1998; 282(5395):1877-82. doi: 10.1126/science.282.5395.1877.
22. van Oijen A M, Blainey P C, Crampton D J, Richardson C C, Ellenberger T, Xie X S. Single-Molecule Kinetics of λ Exonuclease Reveal Base Dependence and Dynamic Disorder. Science. 2003; 301(5637):1235-8. doi: 10.1126/science.1084387.
23. Meric I, Caruso V, Caldwell R, Hone J, Shepard K L, Wind S J. Hybrid carbon nanotube-silicon complementary metal oxide semiconductor circuits. Journal of Vacuum Science & Technology B. 2007; 25(6):2577-80. doi: 10.1116/1.2800322. PubMed PMID: ISI: 000251611900161.
24. Kang S J, Kocabas C, Ozel T, Shim M, Pimparkar N, Alam M A, et al. High-performance electronics using dense, perfectly aligned arrays of single-walled carbon nanotubes. Nat Nano. 2007; 2(4):230-6.
25. Polk B J, Stelzenmuller A, Mijares G, MacCrehan W, Gaitan M. Ag/AgCl microelectrodes with improved stability for microfluidics. Sensors and Actuators B: Chemical. 2006; 114(1):239-47. doi: 10.1016/j.snb.2005.03.121.
26. Wang L, Meric I, Huang P Y, Gao Q, Gao Y, Tran H, et al. One-Dimensional Electrical Contact to a Two-Dimensional Material. Science. 2013; 342(6158):614-7. doi: 10.1126/science.1244358. PubMed PMID: WOS: 000326334300047.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. An integrated circuit comprising:
    a substrate;
    a plurality of sectors arranged on the substrate, wherein each sector in the plurality of sectors comprises:
        a programmable switch controller;
        a counter bias line;
        an amplifier input line;

a plurality of nano-electronic measurement devices spatially arranged on the substrate, wherein
each respective nano-electronic measurement device in the plurality of nano-electronic measurement devices includes a source that is coupled to the counter bias line and a drain that is coupled to the amplifier input line thereby obtaining an electrical signal on the drain of the respective nano-electronic measurement device,
the electrical signal is any one of a discrete set of electrical signals,
an identity of the electrical signal in the discrete set of electrical signals is determined by an electrical interaction between the corresponding nano-electronic measurement device and a particular charge label in a plurality of charge labels; and
a plurality of switches, wherein each switch in the plurality of switches gates the electrical signal between the drain of a corresponding nano-electronic measurement device in the plurality of nano-electronic measurement devices and the amplifier input line between
(i) an on state, in which the electrical signal at the drain of the corresponding nano-electronic measurement device is delivered to the amplifier input line, and
(ii) an off state, in which the electrical signal at the drain of the corresponding nano-electronic measurement device is not delivered to the amplifier input line, wherein
each respective switch in the plurality of switches is independently wired to the programmable switch controller thereby causing the respective switch to be in one of the on state and the off state responsive to the programmable switch controller.

2. The integrated circuit of claim 1, further comprising:
a first clock signal line and a data input line, and wherein
the programmable switch controller of a sector in the plurality of sectors comprises a first shift register comprising a first plurality of flip-flops in electrical communication with the first clock signal line, wherein
the first plurality of flip-flops comprises an initial flip-flop and a terminal flip-flop,
each flip-flop includes a serial input and a serial output, wherein the serial output of each respective flip-flop in the first plurality of flip-flops, other than the terminal flip-flop, is uniquely electrically connected to the serial input of another flip-flop in the first plurality of flip-flops, thereby electrically coupling the first plurality of flip-flops in series,
the serial input of the initial flip-flop is electrically connected to the data input line, wherein the first shift register is configured to receive a device scan chain sequence, from the data input line, that is propagated through the first plurality of flip-flops by electrical pulses in the first clock signal line thereby independently biasing each flip-flop in the first plurality of flip-flops to one of a first state and a second state; and
each respective switch in the plurality of switches is independently wired to the programmable switch controller through a corresponding flip-flop in the first plurality of flip-flops thereby causing the respective switch to be in the off state when the corresponding flip-flop is biased to the first state and causing the respective switch to be in the on state when the corresponding flip-flop is biased to the second state.

3. The integrated circuit of claim 2, wherein the sector in the plurality of sectors further comprises:
a shunt scan chain input line; and
a shunt clock signal line;
the programmable switch controller further comprises a second shift register comprising a second plurality of flip-flops in electrical communication with the shunt clock signal line, wherein
the second plurality of flip-flops comprises an initial flip-flop and a terminal flip flop,
each flip-flop in the second plurality of flip-flops includes a serial input and a serial output, wherein the serial output of each flip-flop in the second plurality of flip-flops, other than the terminal flip-flop, is uniquely electrically connected to the serial input of another flip-flop in the second plurality of flip-flops, thereby electrically coupling the second plurality of flip-flops in series,
the serial input of the initial flip-flop in the second plurality of flip-flops is electrically connected to the shunt scan chain input line, wherein the second shift register is configured to receive a shunt scan chain sequence that is propagated through the second plurality of flip-flops by electrical pulses in the shunt clock signal line, thereby independently biasing each flip-flop in the second plurality of flip-flops to one of a third state and a forth state;
the programmable switch controller further comprises a plurality of multiplexers, wherein each multiplexer in the plurality of multiplexers includes a first input line, a second input line, a select line, and an output line, wherein
the first input line of each respective multiplexer in the plurality of multiplexers is in electrical communication with the serial output of a first corresponding flip-flop in the first plurality of flip-flops,
the second input line of each respective multiplexer in the plurality of multiplexers is in electrical communication with the serial input of the first corresponding flip-flop in the first plurality of flip-flops,
the select line of each respective multiplexer in the plurality of multiplexers is in electrical communication with the serial output of a first corresponding flip-flop in the second plurality of flip-flops, and
the output line of each respective multiplexer in the plurality of multiplexers is in electrical communication with the serial input of a second corresponding flip-flop in the first plurality of flip-flops; and
a first plurality of AND gates, wherein each AND gate in the first plurality of AND gates comprises an output, a first input and a second input, wherein
the first input of each respective AND gate in the first plurality of AND gates is in electrical communication with the first clock signal line,
the second input of each respective AND gate in the first plurality of AND gates is in electrical communication with the serial output of the first corresponding flip-flop in the second plurality of flip-flops, and
each respective flip-flop in the first plurality of flip-flops is in electrical communication with the first clock signal line through the output of a corresponding AND gate in the first plurality of AND gates, wherein when a respective flip-flop in the second plurality of flip-flops, that is in electrical communication with the second input of the respective AND gate, is in the third state, the first clock signal line is not applied to the respective flip-flop in the first plurality of flip-flops and the select line of the multiplexer in the plurality of multiplexers that is in electrical communication with the output of the respective flip-flop in the second plurality of flip-flops is biased to the second input line of the respective multiplexer, and when the flip-flop in the second plurality of flip-flops, that is in electrical communication with the second input of the respective AND gate, is in the fourth state, the first clock signal line is applied to the respective flip-flop in the first plurality of flip-flops and the select line of the multiplexer in the plurality of multiplexers that is in electrical communication with the output of the respective flip-flop in the second plurality of flip-flops is biased to the first input line of the respective multiplexer.

4. The integrated circuit of claim 3, wherein the output line of each respective multiplexer in the plurality of multiplexers is in electrical communication with the serial input of a second corresponding flip-flop in the first plurality of flip-flops through a corresponding buffer gate in a plurality of buffer gates.

5. The integrated circuit of claim 3, wherein
each flip-flop in the first plurality of flip-flops further comprises a first reset;
each flip-flop in the second plurality of flip-flops further comprises a second reset;
the sector further comprises a shunt signal line; and
the programmable switch controller further comprises a second plurality of AND gates, wherein each AND gate in the second plurality of AND gates has an output, a first input and a second input, wherein
the first input of each respective AND gate in the second plurality of AND gates is in electrical communication with the serial output of a first flip-flop in the first plurality of flip-flops,
the second input of each respective AND gate in the second plurality of AND gates is in electrical communication with the shunt signal line, and
the output of each respective AND gate in the second plurality of AND gates is in electrical communication with the first reset of the corresponding flip-flop in the first plurality of flip-flops and the second reset of a corresponding flip-flop in the second plurality of flip-flops, thereby causing the first corresponding flip-flop to reset to the first state and the second corresponding flip-flop to reset to the third state when the shunt signal line is asserted at the same time that the data input line drives the corresponding flip-flop in the first plurality of flip-flop to the second state.

6. The integrated circuit of claim 2, wherein the data input line is configured to receive instructions that permanently by-pass more than fifty percent of the devices in the plurality of devices in a sector in the plurality of sectors.

7. The integrated circuit of claim 6, wherein the plurality of sectors comprises ten or more sectors and the plurality of nano-electronic measurement devices in each sector in the plurality of sectors comprises one hundred devices.

8. The integrated circuit of claim 2, wherein the integrated circuit is configured to receive signals on the data input line that permanently bypass fifty percent or more of the nano-electronic measurement devices in a sector in the plurality of sectors thereby permanently causing bypassed nano-electronic measurement devices to be in the off state.

9. The integrated circuit of claim 2, wherein the integrated circuit is configured to receive signals on the data input line that permanently bypass eighty percent or more of the nano-electronic measurement devices in a sector in the plurality of sectors thereby permanently causing bypassed nano-electronic measurement devices to be in the off state.

10. The integrated circuit of claim 1, wherein
the programmable switch controller of a sector in the plurality of sectors comprises:
a memory controller,
a memory in electrical communication with the memory controller,
a column decoder in electrical communication with the memory, and
a row decoder in electrical communication with the memory;
and wherein the sector further comprises:
a plurality of AND gates, wherein each AND gate in the plurality of AND gates comprises an output, a first input and a second input, wherein
the first input of each respective AND gate in the plurality of AND gates is in electrical communication with the column decoder,
the second input of each respective AND gate in the plurality of AND gates is in electrical communication with the row decoder, and
each respective switch in the plurality of switches is independently wired to the programmable switch controller through the output of a corresponding AND gate in the plurality of AND gates, thereby causing the respective switch to be in the on state when the row decoder and the column decoder both signal a first state to the respective switch and otherwise causing the respective switch to be in the off state.

11. The integrated circuit of claim 1, wherein
the sector further comprises a first clock line, a data input line, a second clock line, and a restart scan chain line;
the programmable switch controller of a sector in the plurality of sectors comprises:
a row shift register comprising a first plurality of flip-flops, wherein an initial flip-flop in the first plurality of flip-flops is in electrical communication with the data input line and the first clock signal line;
a plurality of AND gates, each AND gate in the plurality of AND gates comprising a first input, a second input and an output, and
a plurality of column shift registers, each column shift register comprising a second plurality of flip-flops, and wherein
the first input of each AND gate in the plurality of AND gates is in electrical communication with an output of a corresponding flip-flop in the first plurality of flip-flops of the row shift register;
the second input of each AND gate in the plurality of AND gates is in electrical communication with the second clock line,
the respective second plurality of flip-flops of each respective column shift register in the plurality of column shift registers comprises an initial flip-flop and a terminal flip-flop,
each flip-flop in the respective second plurality of flip-flops includes a serial data input, a clock pulse input, and a serial data output, the serial data output of each respective flip-flop in the second plurality of flip-flops, other than the terminal flip-flop, is uniquely electrically connected to the serial data input of another flip-flop in the second plurality of flip-flops, thereby electrically coupling the second plurality of flip-flops in series, the clock pulse input of each flip-flop in the second plurality of flip-flops is electrically connected to the output of an AND gate in the first plurality of AND gates, each respective column shift register in the plurality of column shift registers is configured to receive a logical "1" or "0" from the restart scan chain line that is propagated from the initial flip-flop in the second plurality of flip-flops through the second plurality of flip-flops by electrical pulses received at the clock pulse input of each respective flip-flop in the second plurality of flip-flops thereby independently biasing each flip-flop in the second plurality of flip-flops to one of the first state and the second state, each respective switch in the plurality of switches is independently wired to the programmable switch controller through the output of a corresponding flip-flop in the second plurality of flip-flops of a corresponding column shift register, thereby causing the respective switch to:

be in the off state when the corresponding flip-flop in the second plurality of flip-flops of the corresponding column shift register is biased to a first state, and be in the on state when the corresponding flip-flop in the second plurality of flip-flops of the corresponding column shift register is biased to the second state.

12. The integrated circuit of claim 1, wherein the sector further comprises a first clock line, a data input line, a second clock line, a load buffer line, and a restart scan chain line, the programmable switch controller of a sector in the plurality of sectors comprises:
 a row shift register comprising a first plurality of flip-flops, wherein an initial flip-flop in the first plurality of flip-flops is in electrical communication with the data input line and the first clock signal line;
 a plurality of AND gates, each AND gate in the plurality of AND gates comprising a first input, a second input, and an output, and
 a plurality of column shift registers, each column shift register comprising a second plurality of flip-flops and a third plurality of flip-flops, and wherein the first input of each AND gate in the first plurality of AND gates is in electrical communication with an output of a corresponding flip-flop in the first plurality of flip-flops of the row shift register;

the second input of each AND gate in the first plurality of AND gates is in electrical communication with the second clock line, the respective second plurality of flip-flops of each respective column shift register in the plurality of column shift registers comprises an initial flip-flop and a terminal flip-flop, each flip-flop in the respective second plurality of flip-flops includes a serial data input, a clock pulse input, and a serial data output, the serial data output of each respective flip-flop in the second plurality of flip-flops, other than the terminal flip-flop, is uniquely electrically connected to the serial data input of another flip-flop in the second plurality of flip-flops, thereby electrically coupling the second plurality of flip-flops in series, the clock pulse input of each flip-flop in the second plurality of flip-flops is electrically connected to the output of an AND gate in the first plurality of AND gates, each respective column shift register in the plurality of column shift registers is configured to receive a logical "1" or "0" from the restart scan chain line that is propagated from the initial flip-flop in the second plurality of flip-flops through the second plurality of flip-flops by electrical pulses received at the clock pulse input of each respective flip-flop in the second plurality of flip-flops thereby independently biasing each flip-flop in the second plurality of flip-flops to one of the first state and the second state, each respective flip-flop in the third plurality of flip-flops comprises a data input, a data output and a clock pulse input, and wherein the clock pulse input of each respective flip-flop in the third plurality of flip-flops is electrically connected to the load buffer line, the data input of each respective flip-flop gate in the third plurality of flip-flops is wired to the output of a corresponding flip-flop in the second plurality of flip-flops, thereby causing the state of the corresponding flip-flop in the third plurality of flip-flops to be biased to the first state when the corresponding flip-flip in the second plurality of flip-flops is biased to the first state and the load buffer line is asserted, and the state of the corresponding flip-flop in the third plurality of flip-flops to be biased to the second state when the corresponding flip-flip in the second plurality of flip-flops is biased to the second state and the load buffer line is asserted, each respective switch in the plurality of switches is independently wired to the programmable switch controller through the output of a corresponding flip-flop in the third plurality of flip-flops of a corresponding column shift register, thereby causing the respective switch to be in the off state when the corresponding flip-flop in the third plurality of flip-flops of the corresponding column shift register is biased to the first state, and be in the on state when the corresponding flip-flop in the third plurality of flip-flops of the corresponding column shift register is biased to the second state.

13. The integrated circuit of claim 1, wherein a nano-electronic measurement device in the plurality of nano-electronic measurement devices is a nanoFET that comprises the source, the drain, a gate, and a channel and wherein the input from the counter bias line is applied from the source to the drain across the channel.

14. The integrated circuit of claim 13, wherein the channel is a nanowire, a carbon nanotube, or a graphene nanoribbon.

15. The integrated circuit of claim 13, wherein the channel is a nanopore.

16. The integrated circuit of claim 1, wherein the counter bias line carries a DC voltage and the application of the counter bias line to the nano-electronic measurement device results in a DC current in the channel nano-electronic measurement device.

17. The integrated circuit of claim 1, wherein the counter bias line carries an AC voltage and a frequency of the AC voltage is changed with time during application of the counter bias line to the nano-electronic measurement device.

18. The integrated circuit of claim 1, wherein each charge label in the plurality of charge labels represents a different type of nucleotide analog in a plurality of nucleotide analogs.

19. The integrated circuit of claim 18, wherein a polymerase enzyme is attached to the corresponding nano-electronic measurement device and the particular charge label that forms an electrical interaction with the corresponding nano-electronic measurement device is freed from a corresponding nucleotide analog in the plurality of nucleotide analogs by the polymerase enzyme as part of a polymerase mediated nucleic acid synthesis reaction with a template nucleic acid.

20. The integrated circuit of claim 19, wherein a charge label in the plurality of charge labels comprises a protein.

21. The integrated circuit of claim 20, wherein the protein has a molecular weight that is between 1/10 and 3 times the molecular weight of the polymerase enzyme.

22. The integrated circuit of claim 20, wherein the protein has a molecular weight that is between 1/10 and 3 times the molecular weight of a phi29 polymerase.

23. The integrated circuit of claim 1, wherein at least one of the charge labels in the plurality of charge labels comprises a polymer chain characterized by multiple charges.

24. The integrated circuit of claim 1, wherein each charge label in the plurality of charge labels comprises a polymer chain characterized by a unique net positive or negative charge.

25. The integrated circuit of claim 1, wherein
a first charge label in the plurality of charge labels comprises a first polymer chain having a unique net positive charge, and
a second charge label in the plurality of charge labels comprises a second polymer chain having a unique net negative charge.

26. The integrated circuit of claim 1, wherein the plurality of nano-electronic measurement devices of a sector in the plurality of sectors are arranged as a row or a column on the substrate.

27. The integrated circuit of claim 1, wherein the plurality of nano-electronic measurement devices of a sector in the plurality of sectors are arranged as a plurality of rows or a plurality of columns on the substrate.

28. The integrated circuit of claim 1, further comprising a plurality of amplifiers, wherein each amplifier in the plurality of amplifiers is in electrical communication with the amplifier input line of a corresponding sector in the plurality of sectors.

29. The integrated circuit of claim 28, wherein an amplifier in the plurality of amplifiers is a current-to-voltage amplifier.

30. The integrated circuit of claim 1, wherein the electrical interaction is electrostatic.

31. The integrated circuit of claim 1, wherein the plurality of nano-electronic measurement devices comprises 1,000 nano-electronic measurement devices.

32. The integrated circuit of claim 1, wherein the plurality of nano-electronic measurement devices comprises 10,000 nano-electronic measurement devices.

33. The integrated circuit of claim 1, wherein the plurality of nano-electronic measurement devices consists of between 1,000 nano-electronic measurement devices and 10 million nano-electronic measurement devices.

34. The integrated circuit of claim 1, wherein the plurality of measurement devices consists of between 10,000 nano-electronic measurement devices and 1 million nano-electronic measurement devices.

35. The integrated circuit of claim 1, wherein
only a single nano-electronic measurement device in the plurality of nano-electronic measurement devices in each sector in the plurality of sectors is in the on state at a given point in time, and
the plurality of nano-electronic measurement devices of each sector in the plurality of sectors comprises three hundred devices.

36. The integrated circuit of claim 1, wherein the plurality of sectors comprises one hundred sectors and the plurality of nano-electronic measurement devices in each sector in the plurality of sectors comprises one thousand devices.

* * * * *